US007488737B2

(12) United States Patent
Xie et al.

(10) Patent No.: US 7,488,737 B2
(45) Date of Patent: Feb. 10, 2009

(54) INDOLES, 1H-INDAZOLES, 1,2-BENZISOXAZOLES, 1,2-BENZOISOTHIAZOLES, AND PREPARATION AND USES THEREOF

(75) Inventors: Wenge Xie, Mahwag, NJ (US); Brian Herbert, Stockholm, NJ (US); Jianguo Ma, Montvale, NJ (US); Truc Minh Nguyen, New York, NY (US); Richard Schumacher, Monroe, NY (US); Carla Maria Gauss, New York, NY (US); Ashok Tehim, Ridgewood, NJ (US)

(73) Assignee: Memory Pharmaceutical Corporation, Montvale, NJ (US)

( * ) Notice: Subject to any disclaimer, the term of this patent is extended or adjusted under 35 U.S.C. 154(b) by 373 days.

(21) Appl. No.: 11/111,958

(22) Filed: Apr. 22, 2005

(65) Prior Publication Data

US 2005/0250808 A1    Nov. 10, 2005

Related U.S. Application Data

(60) Provisional application No. 60/619,767, filed on Oct. 19, 2004, provisional application No. 60/564,239, filed on Apr. 22, 2004.

(51) Int. Cl.
*A01N 43/42* (2006.01)
*A61K 31/44* (2006.01)
*A61K 31/47* (2006.01)
*C07D 401/00* (2006.01)
*C07D 405/00* (2006.01)
*C07D 409/00* (2006.01)
*C07D 411/00* (2006.01)
*C07D 211/02* (2006.01)

(52) U.S. Cl. ............ 514/304; 514/309; 546/126; 546/183

(58) Field of Classification Search .......... 546/199, 546/126, 183; 514/322, 304, 309
See application file for complete search history.

(56) References Cited

U.S. PATENT DOCUMENTS

| 4,605,652 | A |   | 8/1986  | Welstead et al. |
|-----------|---|---|---------|-----------------|
| 4,775,668 | A |   | 10/1988 | Jefson et al. |
| 4,789,673 | A |   | 12/1988 | Donatsch et al. |
| 4,798,829 | A |   | 1/1989  | King et al. |
| 4,845,092 | A |   | 7/1989  | Sanger et al. |
| 4,886,808 | A |   | 12/1989 | King |
| 4,895,943 | A |   | 1/1990  | Friedmann |
| 4,910,193 | A |   | 3/1990  | Buchheit |
| 4,910,207 | A |   | 3/1990  | Donatsch et al. |
| 4,937,247 | A | * | 6/1990  | King ............ 514/299 |
| 4,942,160 | A |   | 7/1990  | Sanger et al. |
| 4,975,436 | A |   | 12/1990 | Tyers |
| 4,985,424 | A |   | 1/1991  | van Wijngaarden et al. |
| 5,017,582 | A |   | 5/1991  | Donatsch |
| 5,034,398 | A | * | 7/1991  | King ............ 514/299 |
| 5,063,231 | A |   | 11/1991 | Sanger et al. |
| 5,098,889 | A |   | 3/1992  | Costall et al. |
| 5,098,909 | A |   | 3/1992  | Williams |
| 5,192,770 | A |   | 3/1993  | Clark et al. |
| 5,204,356 | A |   | 4/1993  | Tyers |
| 5,223,625 | A |   | 6/1993  | van Wijingaarden et al. |
| 5,272,154 | A |   | 12/1993 | Dixon et al. |
| 5,273,972 | A |   | 12/1993 | Jagdmann et al. |
| 5,446,050 | A |   | 8/1995  | Rosen |
| 5,543,426 | A |   | 8/1996  | Dixon et al. |
| 5,561,149 | A |   | 10/1996 | Azria et al. |
| 5,641,802 | A |   | 6/1997  | Arcamone et al. |
| 5,679,673 | A |   | 10/1997 | Bowen et al. |
| 5,773,436 | A |   | 6/1998  | Muller et al. |
| 5,985,866 | A |   | 11/1999 | Muller et al. |
| 6,492,385 | B2 |  | 12/2002 | Myers et al. |
| 6,500,840 | B2 |  | 12/2002 | Myers et al. |
| 6,599,916 | B2 |  | 7/2003  | Myers et al. |
| 6,624,173 | B1 |  | 9/2003  | Crooks et al. |
| 6,780,861 | B2 |  | 8/2004  | Nozulak |
| 6,828,330 | B2 |  | 12/2004 | Walker et al. |
| 6,849,620 | B2 |  | 2/2005  | Walker et al. |
| 6,911,543 | B2 |  | 6/2005  | Walker et al. |
| 7,001,900 | B2 |  | 2/2006  | Jacobsen et al. |
| 2002/0086871 | A1 |  | 7/2002 | O'Neill et al. |

(Continued)

FOREIGN PATENT DOCUMENTS

| CA | 2 361 437 | 3/1988 |
| DE | 10 305 922 | 3/2004 |
| EP | 0013138 | 7/1980 |
| EP | 0 200 444 | 11/1986 |
| EP | 0 214 772 | 3/1987 |
| EP | 0 279 512 | 8/1988 |
| EP | 0 377 238 | 7/1990 |
| EP | 0 498 466 | 8/1992 |
| EP | 1 079 828 | 3/2001 |
| EP | 1 219 622 | 7/2002 |

(Continued)

OTHER PUBLICATIONS

Fludzinski et al., Journal of Medicinal Chemistry, 1987, vol. 30, pp. 1535-1537.*

(Continued)

*Primary Examiner*—D. Margaret Seaman
*Assistant Examiner*—Niloofar Rahmani
(74) *Attorney, Agent, or Firm*—Millen, White, Zelano, Branigan, P.C.

(57) ABSTRACT

The present invention relates generally to the field of ligands for nicotinic acetylcholine receptors (nACh receptors), activation of nACh receptors, and the treatment of disease conditions associated with defective or malfunctioning nicotinic acetylcholine receptors, especially of the brain. Further, this invention relates to novel compounds (indazoles and benzothiazoles), which act as ligands for the α7 nACh receptor subtype, methods of preparing such compounds, compositions containing such compounds, and methods of use thereof.

20 Claims, No Drawings

U.S. PATENT DOCUMENTS

| | | |
|---|---|---|
| 2002/0119972 A1 | 8/2002 | Leftheris et al. |
| 2003/0073707 A1 | 4/2003 | Walker et al. |
| 2004/0002513 A1 | 1/2004 | Mazurov et al. |
| 2005/0182062 A1 | 8/2005 | Sanofi |
| 2005/0209236 A1 | 9/2005 | Hendrix et al. |
| 2006/0014750 A1 | 1/2006 | O'Donnell et al. |

FOREIGN PATENT DOCUMENTS

| | | |
|---|---|---|
| EP | 1 235 826 | 9/2002 |
| EP | 0 261 964 | 8/2008 |
| FR | 2 548 666 | 1/1985 |
| FR | 2 845 388 | 4/2004 |
| GB | 2 125 398 | 3/1984 |
| GB | 2 145 416 | 3/1985 |
| JP | 2002-30084 | 1/2002 |
| WO | WO 84/00166 | 1/1984 |
| WO | WO 85/01048 | 3/1985 |
| WO | WO 90/14347 | 11/1990 |
| WO | WO 91/09593 | 7/1991 |
| WO | WO 92/12149 | 7/1992 |
| WO | WO 93/08185 | 4/1993 |
| WO | WO 97/30998 | 8/1997 |
| WO | WO 00/44755 | 8/2000 |
| WO | WO 00/58311 | 10/2000 |
| WO | WO 01/58869 | 8/2001 |
| WO | WO 01/90109 | 11/2001 |
| WO | WO 01/92260 | 12/2001 |
| WO | WO 02/17358 | 2/2002 |
| WO | WO 02/36114 | 5/2002 |
| WO | WO 02/085901 | 10/2002 |
| WO | WO 00/45846 | 12/2002 |
| WO | WO 02/096911 | 12/2002 |
| WO | WO 02/100833 | 12/2002 |
| WO | WO 02/100857 | 12/2002 |
| WO | WO 02/100858 | 12/2002 |
| WO | WO 03/022856 | 3/2003 |
| WO | WO 03/029252 | 4/2003 |
| WO | WO 03/037806 | 5/2003 |
| WO | WO 03/037896 | 5/2003 |
| WO | WO 03/042210 | 5/2003 |
| WO | WO 03/051874 | 6/2003 |
| WO | WO 03/070731 | 8/2003 |
| WO | WO 03/072578 | 9/2003 |
| WO | WO 03/078431 | 9/2003 |
| WO | WO 03/080606 | 10/2003 |
| WO | WO 03/094830 | 11/2003 |
| WO | WO 03/101987 | 11/2003 |
| WO | WO 2004/013137 | 2/2004 |
| WO | WO 2004/014864 | 2/2004 |
| WO | WO 2004/014922 | 2/2004 |
| WO | WO 2004/016617 | 2/2004 |
| WO | WO 2004016616 | 2/2004 |
| WO | WO 2004/029050 | 4/2004 |
| WO | WO 2004/033456 | 4/2004 |
| WO | WO 2005/001299 | 2/2005 |

OTHER PUBLICATIONS

Bermudez et al., Journal of Medicinal Chemistry, 1990, vol. 33, pp. 1924-1929.*

Robertson et al., Journal of Medicinal Chemistry, 1990, vol. 33, pp. 3176-3181.*

Schmidt et al., Molecular Pharmacology, 1990, vol. 38, pp. 511-516.*

Robertson et al., Journal of Medicinal Chemistry, 1992, vol. 35, pp. 310-319.*

Schaus et al., Journal of Medicinal Chemistry, 1998, vol. 41, pp. 1943-1955.*

Int'l. Search Report and the Written Opinion of the Int'l. Searching Authority, issued Nov. 24, 2005 in PCT/US2005/013938.

Sakaguchi et al. Chem Phar Bull., 2001, 49(4) 424-436.

Bermudez et al., J. Med. Chem., 1990, 33, 1924-1929.

Nurhrich et al., Eur. J. Med. Chem., 1996, No. 31, pp. 957-964.

Schaus et al., J. Med. Chem., 1998, No. 41, pp. 1943-1955.

Robertson et al., J. Med. Chem., 1990, No. 33, pp. 3176-3181.

Macor et al., Bioorganic & Medicinal Chem. Letters 11, 2001, pp. 319-321.

Toledana, et al., Journal of Molecular Structure 406, 1997, pp. 223-232.

Romanelli et al., Arzneim-Forsch/Drug Res. 43 (II) Nr. 8 1993, pp. 913-918.

S.M. Evans et al., "Probing the 5-$HT_3$ Receptor Site Using Novel Indole-3-Glyoxylic Acid Derivatives", Med. Chem. Res. (1993), 3:386-406.

D. Flammia, "Lobeline: Structure-Affinity Investigation of Nicotinic Acetylcholinergic Receptor Binding", J. Med. Chem. (1999), 42:3726-2731.

R. Azuma et al. "Metabolism and Disposition of GTS-21, A Novel Drug for Alzheimer's Disease", Xenobiotica (1999), vol. 29, No. 7, pp. 747-762.

K. E. Stevens. et al., "Selective $\alpha_7$-nicotinic agonists normalize inhibition of auditory response in DBA mice", Psychopharmacology (1998), 136:320-327.

R. Azuma et al., "The effect of repeat administration of GTS-21 on mixed-function oxidase activities in rat", Elsevier Science Ireland Ltd., Toxicology Letters 110 (1999) pp. 137-144.

M. Decker, et al., "Neuronal Nicotinic Acetylcholine Receptors: Novel Targets for CNS Therapeutics", 2000, pp. 1-14.

M. W. Holladay et al., "Neuronal Nicotinic Acetylcholine Receptors as Targets for Drug Discovery", Journal of Medicinal Chemistry, vol. 40, No. 26, (1997), pp. 4169-4194.

Astles et al., Current Drug Targets—CNS Neurological Disorders, 2002, 1, pp. 337-348.

Mazurov et al., Biorg. & Med. Chem. Lett., 2005, No. 1 15, pp. 2073-2077.

Nurhrich et al., Eur. J. Med. Chem. 1996, No. 31, pp. 957-964.

Bermudez et al., J. Med. Chem., 1990, 33,1924-1929.

* cited by examiner

INDOLES, 1H-INDAZOLES, 1,2-BENZISOXAZOLES, 1,2-BENZOISOTHIAZOLES, AND PREPARATION AND USES THEREOF

This application claims the benefit of U.S. Provisional application Ser. No. 60/564,239, filed Apr. 22, 2004, and U.S. Provisional application Ser. No. 60/619,767, filed Oct. 19, 2004, the entire disclosures of which are hereby incorporated by reference.

This application is also related to U.S. patent application Ser. No. 11/018,429, filed Dec. 22, 2004, which claims the benefit of U.S. Provisional application Ser. No. 60/530,891, filed Dec. 22, 2003, and U.S. Provisional application Ser. No. 60/606,897, filed Sep. 3, 2004, the entire disclosures of which are hereby incorporated by reference.

FIELD OF THE INVENTION

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds, which act as ligands for the α7 nAChR subtype, methods of preparing such compounds, compositions comprising such compounds, and methods of use thereof.

BACKGROUND OF THE INVENTION

There are two types of receptors for the neurotransmitter, acetylcholine: muscarinic receptors and nicotinic receptors, based on the selectivity of action of muscarine and nicotine, respectively. Muscarinic receptors are G-protein coupled receptors. Nicotinic receptors are members of the ligand-gated ion channel family. When activated, the conductance of ions across the nicotinic ion channels increases.

Nicotinic alpha-7 receptor protein forms a homo-pentameric channel in vitro that is highly permeable to a variety of cations (e.g., $Ca^{++}$). Each nicotinic alpha-7 receptor has four transmembrane domains, named M1, M2, M3, and M4. The M2 domain has been suggested to form the wall lining the channel. Sequence alignment shows that nicotinic alpha-7 is highly conserved during evolution. The M2 domain that lines the channel is identical in protein sequence from chicken to human. For discussions of the alpha-7 receptor, see, e.g., Revah et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The nicotinic alpha-7 receptor channel is expressed in various brain regions and is believed to be involved in many important biological processes in the central nervous system (CNS), including learning and memory. Nicotinic alpha-7 receptors are localized on both presynaptic and postsynaptic terminals and have been suggested to be involved in modulating synaptic transmission. It is therefore of interest to develop novel compounds, which act as ligands for the α7 nAChR subtype, for the treatment of disease conditions associated with defective or malfunctioning nicotinic acetylcholine receptors.

SUMMARY OF THE INVENTION

This invention relates to novel compounds, which act as ligands for the α7 nAChR subtype, methods of preparing such compounds, compositions comprising such compounds, and methods of use thereof.

DETAILED DESCRIPTION OF THE INVENTION

The present invention includes compounds of Formulas I, II, or III:

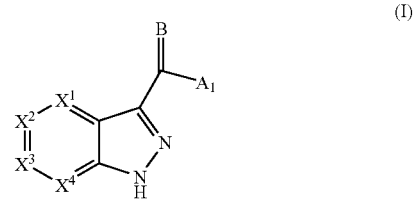

(I)

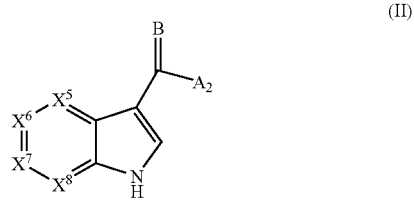

(II)

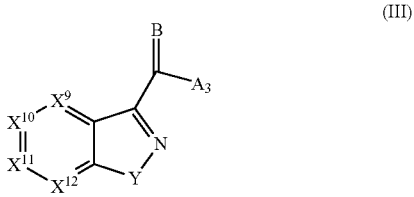

(III)

wherein $X^1$ to $X^4$ are each, independently, CH, $CR^1$, or N, wherein at most one of $X^1$ to $X^4$ is N;

$X^5$ to $X^8$ are each, independently, CH, $CR^2$, or N, wherein at most one of $X^5$ to $X^8$ is N;

$X^9$ to $X^{12}$ are each, independently, CH, $CR^3$, or N, wherein at most one of $X^9$ to $X^{12}$ is N;

B is O, S, or $H_2$;

Y is O or S;

$A_1$ is

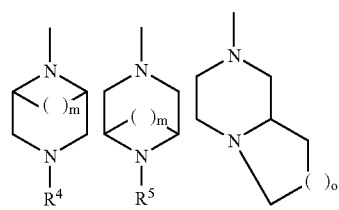

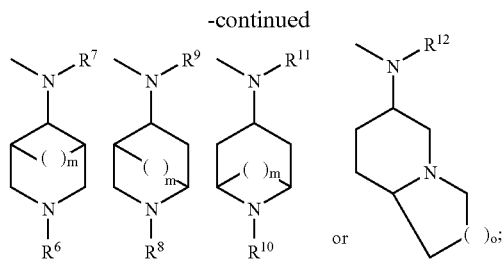

wherein when $A_1$ is of the following formula, m is 2 or 3, and B is O, then $R^1$ is other than H, $CH_3$ or halogen, or $R^{10}$ is other than H, $CH_3$, or $C_2H_5$

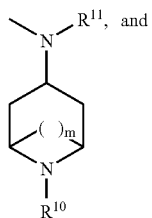

wherein when $A_1$ is of the following formula, m is 1 or 2, and B is O, then $R^1$ is other than H or $CH_3$, or $R^8$ is other than H, $CH_3$, or $C_2H_5$

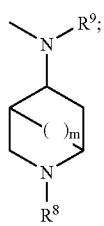

$A_2$ is

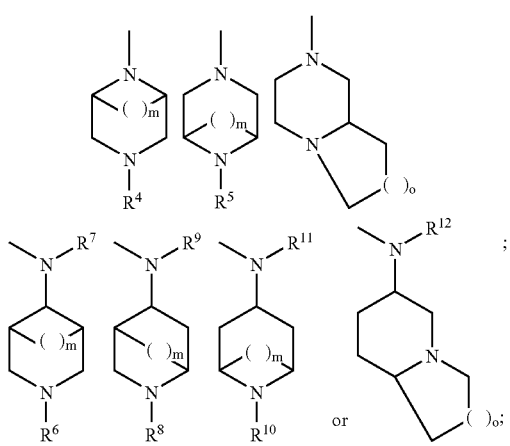

wherein when $A_2$ is of the following formula, m is 2 or 3, and B is O, then $R^2$ is other than H, $CH_3$, or halogen, or $R^{10}$ is other than H, $CH_3$, or $C_2H_5$

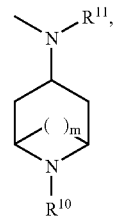

wherein when $A_2$ is of the following formula, m is 2, and B is O, then $R^2$ is other than H or $CH_3$, or $R^8$ is other than H, $CH_3$, or $C_2H_5$

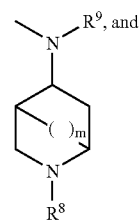

wherein when $A_2$ is of the following formula, m is 2 or 3, and B is O, then $R^2$ is other than H or $CH_3$, or $R^5$ is other than H, $CH_3$, or $C_2H_5$

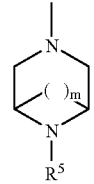

$A_3$ is

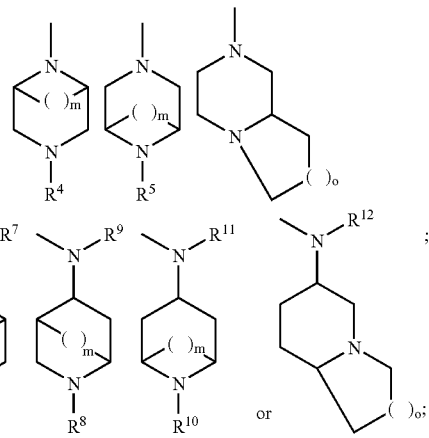

wherein when $A_3$ is of the following formula, m is 2 or 3, Y is O, and B is O, then $R^3$ is other than H, $CH_3$, halogen, $NO_2$ or $NH_2$, or $R^{10}$ is other than H, $CH_3$, or $C_2H_5$

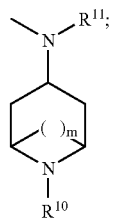

$R^1$, $R^2$ and $R^3$ are each, independently,
H,
$C_{1-6}$alkyl (e.g., $CH_3$) which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^3R^4$, Ar, Het, or combinations thereof,
$C_{2-6}$-alkenyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^4$, Ar, Het, or combinations thereof,
$C_{2-6}$-alkynyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^4$, $Si(R^{15})_3$, Ar, Het, or combinations thereof,
$C_{3-8}$-cycloalkyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, unsubstituted $C_{3-8}$-cycloalkyl, $SO_2R^3$, $SO_2NR^3R^4$, Ar, Het, or combinations thereof,
halogen (e.g., F, Cl, Br, I),
CN, $NO_2$, $NR^{13}R^{14}$, SH, $SR^{13}$, $SOR^{13}$, $SO_2R^{13}$, $SO_2NR^{13}R^{14}$, $NR^{13}SO_2R^{14}$, $CONR^{13}R^{14}$, $CSNR^{13}R^{14}$, $COOR^{13}$, $NR^{13}COR^{14}$, $NR^{13}CSR^{14}$, $NR^{13}CONR^{13}R^{14}$, $NR^{13}CSNR^{13}R^{14}$, $NR^{13}COOR^{14}$, $NR^{13}CSOR^{14}$, $OCONR^{13}R^{14}$, $OCSNR^{13}R^{14}$,
Ar,
Het, or
$R^{16}O-$;
$R^4$ to $R^{12}$ are each, independently,
H,
$C_{1-4}$-alkyl (e.g., $CH_3$) which is unsubstituted or substituted one or more times by F, Cl, Br, I, CN, alkoxy having 1 to 4 carbon atoms (e.g., $OCH_3$), Ar (e.g., phenyl) or combinations thereof,
$C_{3-6}$-alkenyl which is unsubstituted or substituted one or more times by F, Cl, Br, I, CN, alkoxy having 1 to 4 carbon atoms (e.g., $OCH_3$), Ar (e.g., phenyl) or combinations thereof,
$C_{3-6}$-alkynyl which is unsubstituted or substituted one or more times by F, Cl, Br, I, CN, alkoxy having 1 to 4 carbon atoms (e.g., $OCH_3$), or Ar (e.g., phenyl) or combinations thereof,
cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl),
cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof (e.g., cyclopentylmethyl, cyclopropylmethyl, etc.),
Ar-alkyl (e.g., benzyl), or
Het-alkyl (e.g., thienylmethyl);
$R^{13}$ and $R^{14}$ are each independently H,
Ar,
Ar-alkyl (e.g., benzyl, fluorobenzyl, methoxybenzyl, phenethyl, phenpropyl),
Het,
$C_{1-4}$-alkyl (e.g., $CH_3$) which is unsubstituted or substituted one or more times by F, Cl, Br, I, CN, OH, alkoxy having 1 to 4 carbon atoms (e.g., $OCH_3$), monoalkylamino, dialkylamino (e.g., diethylamino), $C_{3-8}$-cycloalkyl, or combinations thereof,
cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl),
$C_{3-6}$-alkenyl which is unsubstituted or substituted one or more times by F, Cl, Br, I, CN, alkoxy having 1 to 4 carbon atoms (e.g., $OCH_3$), Ar (e.g., phenyl) or combinations thereof, or
$C_{3-6}$-alkynyl which is unsubstituted or substituted one or more by F, Cl, Br, I, CN, alkoxy having 1 to 4 carbon atoms (e.g., $OCH_3$), or Ar (e.g., phenyl) or combinations thereof;
$R^{15}$ is $C_{1-6}$-alkyl (e.g., $CH_3$);
$R^{16}$ is H,
$C_{1-6}$-alkyl (e.g., $CH_3$) which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof,
$C_{3-6}$-alkenyl which is unsubstituted or substituted one or more by F, Cl, Br, I, CN, OH, alkoxy having 1 to 4 carbon atoms (e.g., $OCH_3$), $NR^3R^{14}$, SH, $SR^3$, $SOR^{13}$, $C_{3-8}$-cycloalkyl, $SO_2R^{13}$, $SO_2NR^{13}R^{14}$, Ar, Het, or combinations thereof,
$C_{3-6}$-alkynyl which is unsubstituted or substituted one or more by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof,
$C_{3-8}$-cycloalkyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof,
$C_{4-8}$-cycloalkylalkyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof,
Ar, or
Het;
m is 1, 2 or 3;
o is 1 or 2;
Ar is an aryl group containing 6 to 10 carbon atoms which is unsubstituted or substituted one or more times by
alkyl having 1 to 8 carbon atoms,
alkoxy having 1 to 8 carbon atoms,
halogen (F, Cl, Br, or I, preferably F or Cl),
amino,
cyano,
hydroxyl,
nitro, halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
sulfo,
sulfonylamino,
Het,
cycloalkylamino wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
cycloalkyloxy wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, or
combinations thereof;
Ar-alkyl is an aryl-alkylene group (e.g., benzyl, phenethyl, phenpropyl) wherein the alkylene portion contains 1 to 4 carbon atoms and is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, and the aryl portion is Ar as defined above; and Het is a heterocyclic group, which is fully saturated, partially saturated or fully unsaturated, having 5 to 10 ring atoms in which at least 1 ring atom is a N, O or S atom, which is unsubstituted or substituted one or more times by
alkyl having 1 to 8 carbon atoms,
alkoxy having 1 to 8 carbon atoms,
halogen (F, Cl, Br, or I, preferably F or Cl),
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkoxycarbonylmethyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
oxo,
sulfo,
sulfonylamino,
cycloalkylamino wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryl containing 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryl-alkylene group (e.g., benzyl, phenethyl, phenpropyl) wherein the aryl portion contains 6 to 10 carbon atoms and the alkylene portion contains 1 to 4 carbon atoms and is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 C atoms, dialkylamino wherein the alkyl portions each have I to 8 carbon atoms, $COR^{16}$, $CSR^{16}$, cyano, hydroxyl, nitro, oxo, or thio, arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, cycloalkyloxy wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio (e.g., furyl, thienyl, methylthienyl, bithienyl, benzylprazolyl, thiazolyl, imidazolyl, methylimidazolyl, pyrrolidinyl, morpholinyl, thiomorpholinyl), heterocyclic-alkyl group, in which the heterocylic portion is fully saturated, partially saturated or fully unsaturated, having 5 to 10 ring atoms in which at least 1 ring atom is a N, O or S atom, and the alkyl portion is an alkylene group containing 1-4 carbon atoms, wherein said heterocyclic-alkyl group is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio (e.g., piperidinylethyl), or combinations thereof; and pharmaceutically acceptable salts thereof.

According to a further aspect of the invention, in the compounds of Formulas I, II, or III, $R^{13}$ and $R^{14}$ are each independently

H,

Ar,

Het, $C_{1-4}$-alkyl which is unsubstituted or substituted one or more times by F, Cl, Br, I, CN, OH, alkoxy having 1 to 4 carbon atoms, monoalkylamino, dialkylamino, $C_{3-8}$-cycloalkyl, or combinations thereof, cycloalkyl having 3 to 10 carbon atoms, which is unsubstituted or substituted one or more times by halogen, hydroxy, oxo, cyano, alkyl having 1 to 4 carbon atoms, alkoxy having 1 to 4 carbon atoms, or combinations thereof, $C_{3-6}$-alkenyl which is unsubstituted or substituted one or more times by F, Cl, Br, I, CN, alkoxy having 1 to 4 carbon atoms, Ar, or combinations thereof, or $C_{3-6}$-alkynyl which is unsubstituted or substituted one or more times by F, Cl, Br, I, CN, alkoxy having 1 to 4 carbon atoms, Ar or combinations thereof.

According to a further aspect of the invention, in the compounds of Formulas I, II, or III, Het is:

is a heterocyclic group, which is fully saturated, partially saturated or fully unsaturated, having 5 to 10 ring atoms in which at least 1 ring atom is a N, O or S atom, which is unsubstituted or substituted one or more times by alkyl having 1 to 8 carbon atoms, alkoxy having 1 to 8 carbon atoms, halogen (F, Cl, Br, or I, preferably F or Cl), amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, monoalkylamino having 1 to 8 carbon atoms, dialkylamino wherein the alkyl portions each have 1 to 8 carbon atoms, carboxy, alkoxycarbonyl, alkoxycarbonylmethyl, alkylaminocarbonyl, acylamido (e.g., acetamido), acyloxy (e.g., acetoxy), alkylthio having 1 to 8 carbon atoms, alkylsulphinyl having 1 to 8 carbon atoms, alkylsulphonyl having 1 to 8 carbon atoms, sulfo, sulfonylamino, cycloalkylamino wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, aryl containing 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, aryl-alkylene group (e.g., benzyl, phenethyl, phenpropyl) wherein the aryl portion contains 6 to 10 carbon atoms and the alkylene portion contains 1 to 4 carbon atoms and is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 C atoms, dialkylamino wherein the alkyl portions each have 1 to 8 carbon atoms, $COR^{16}$, $CSR^{16}$, cyano, hydroxyl, nitro, oxo, or thio, arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, cycloalkyloxy wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio (e.g., furyl, thienyl, methylthienyl, bithienyl, benzylprazolyl, thiazolyl, imidazolyl, methylimidazolyl, pyrrolidinyl, morpholinyl, thiomorpholinyl), heterocyclic-alkyl group, in which the heterocylic portion is fully saturated, partially saturated or fully unsaturated, having 5 to 10 ring atoms in which at least 1 ring atom is a N, O or S atom, and the alkyl portion is an alkylene group containing 1-4 carbon atoms, wherein said heterocyclic-alkyl group is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio (e.g., piperidinylethyl), or combinations thereof.

According to a further aspect of the invention, in the compounds of Formulas I, II, or III, Het is:

a heterocyclic group, which is fully saturated, partially saturated or fully unsaturated, having 5 to 10 ring atoms in which at least 1 ring atom is a N, O or S atom, which is unsubstituted or substituted one or more times by alkyl having 1 to 8 carbon atoms, alkoxy having 1 to 8 carbon atoms,
halogen (F, Cl, Br, or I, preferably F or Cl),
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
sulfo,
sulfonylamino,
cycloalkylamino wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, aryl containing 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, aryl-alkylene group (e.g., benzyl, phenethyl, phenpropyl) wherein the aryl portion contains 6 to 10 carbon atoms and the alkylene portion contains 1 to 4 carbon atoms and is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 C carbon atoms, $COR^{16}$, $CSR^{16}$, cyano, hydroxyl, nitro, oxo, or thio, aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 C atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, cycloalkyloxy wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 C atoms, $COR^{16}$, $CSR^{16}$, cyano, hydroxyl, nitro, oxo, or thio (e.g., furyl, thienyl, methylthienyl, bithienyl, benzylprazolyl, thiazolyl, imidazolyl, methylimidazolyl, pyrrolidinyl, morpholinyl, thiomorpholinyl), or combinations thereof.

According to a further aspect, the present invention includes compounds of Formula I(a):

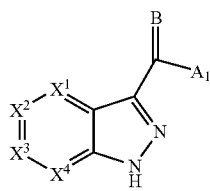

(Ia)

wherein
$X^1$ to $X^4$, and B are as defined previously;
$A_1$ is

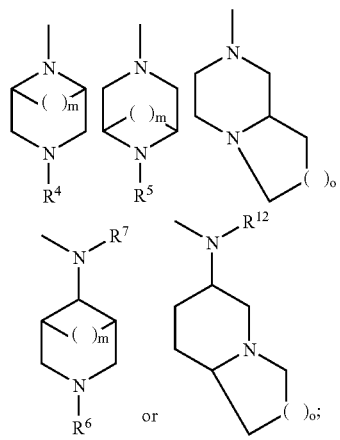

and $R^4$-$R^7$, $R^{12}$, m and o are as previously defined;
and pharmaceutically acceptable salts thereof.

According to a further aspect, the present invention includes compounds of Formula I(b):

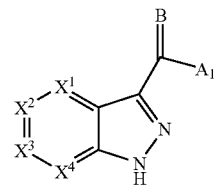

(Ib)

wherein
$X^1$ to $X^4$, and B are as defined previously;
$A_1$ is

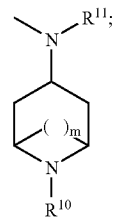

$R^{10}$ and $R^{11}$ are as defined previously; and
m is 1; and pharmaceutically acceptable salts thereof.

According to a further aspect, the present invention includes compounds of Formula I(c):

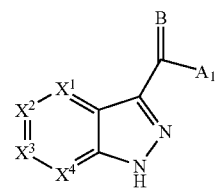

(Ic)

wherein
$X^1$ to $X^4$, and B are as defined previously;
$A_1$ is

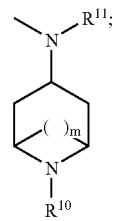

$R^{10}$, $R^{11}$ and m are as defined previously; and
$R^1$ is $C_{2-6}$-alkyl (e.g., $C_2H_5$) which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, C$_{2-6}$-alkenyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Ar, Het, or combinations thereof, C$_{2-6}$-alkynyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Si(R$^{15}$)$_3$, Ar, Het, or combinations thereof, C$_{3-8}$-cycloalkyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, unsubstituted C$_{3-8}$-cycloalkyl, SO$_2$R$^{13}$, SO$_2$NR$^{13}$R$^{14}$, Ar, Het, or combinations thereof, CN, NO$_2$, NR$^{13}$R$^{14}$, SH, SR$^{13}$, SOR$^{13}$, SO$_2$R$^{13}$, SO$_2$NR$^{13}$R$^{14}$, NR$^{13}$SO$_2$R$^{14}$, CONR$^{13}$R$^{14}$, CSNR$^{13}$R$^{14}$, COOR$^{13}$, NR$^{13}$COR$^{14}$, NR$^{13}$CSR$^{14}$, NR$^{13}$CONR$^{13}$R$^{14}$, NR$^{13}$CSNR$^{13}$R$^{14}$, NR$^{13}$COOR$^{14}$, NR$^{13}$CSOR$^{14}$, OCONR$^{13}$R$^{14}$, OCSNR$^{13}$R$^{14}$, Ar,
Het, or
R$^{16}$O—; and pharmaceutically acceptable salts thereof.

According to a further aspect, the present invention includes compounds of Formula I(d):

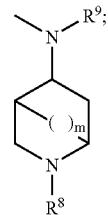

(Id)

wherein
X$^1$ to X$^4$, and B are as defined previously;
A$_1$ is

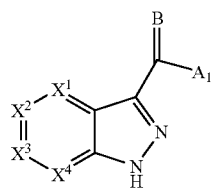

R$^8$ and R$^9$ are as defined previously; and
m is 3; and pharmaceutically acceptable salts thereof.

According to a further aspect, the present invention includes compounds of Formula I(e):

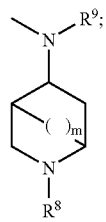

(Ie)

wherein
X$^1$ to X$^4$, and B are as defined previously;
A$_1$ is

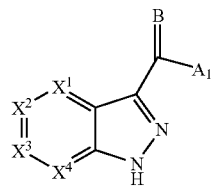

R$^8$ and R$^9$ are as defined previously; and

R$^1$ is C$_{2-6}$-alkyl (e.g., C$_2$H$_5$) which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Ar, Het, or combinations thereof, C$_{2-6}$-alkenyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Ar, Het, or combinations thereof, C$_{2-6}$-alkynyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Si(R$^{15}$)$_3$, Ar, Het, or combinations thereof, C$_{3-8}$-cycloalkyl which is unsubstituted or substituted one or more times by F, Cl, Br, I, CN, OH, alkoxy having 1 to 4 carbon atoms (e.g., OCH$_3$), NR$^3$R$^{14}$, SH, SR$^{13}$, SOR$^{13}$, unsubstituted C$_{3-8}$-cycloalkyl, SO$_2$R$^{13}$, SO$_2$NR$^{13}$R$^{14}$, Ar, Het, or combinations thereof, halogen (e.g., F, Cl, Br, I), CN, NO$_2$, NR$^{13}$R$^{14}$, SH, SR$^{13}$, SOR$^{13}$, SO$_2$R$^{13}$, SO$_2$NR$^{13}$R$^{14}$, NR$^{13}$SO$_2$R$^{14}$, CONR$^{13}$R$^{14}$, CSNR$^{13}$R$^{14}$, COOR$^{13}$, NR$^{13}$COR$^{14}$, NR$^{13}$CSR$^{14}$, NR$^{13}$CONR$^{13}$R$^{14}$, NR$^{13}$CSNR$^{13}$R$^{14}$, NR$^{13}$COOR$^{14}$, NR$^{13}$CSOR$^{14}$, OCONR$^{13}$R$^{14}$, OCSNR$^{13}$R$^{14}$, Ar,
Het, or
R$^{16}$O—; and pharmaceutically acceptable salts thereof.

According to a further aspect, the present invention includes compounds of Formula I(f):

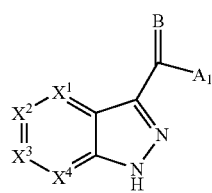

(If)

wherein
X$^1$ to X$^4$, and A$_1$ are as defined previously; and
B is S; and pharmaceutically acceptable salts thereof.

According to a further aspect, the present invention includes compounds of Formula I(g):

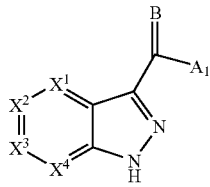
(Ig)

wherein
$X^1$ to $X^4$, and $A_1$ are as defined previously; and
B is $H_2$; and pharmaceutically acceptable salts thereof.

According to a further aspect, the present invention includes compounds of Formula II(a):

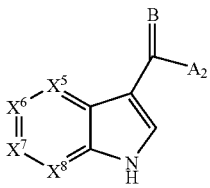
(IIa)

wherein
$X^5$ to $X^8$, and B are as defined previously; and
$A_2$ is

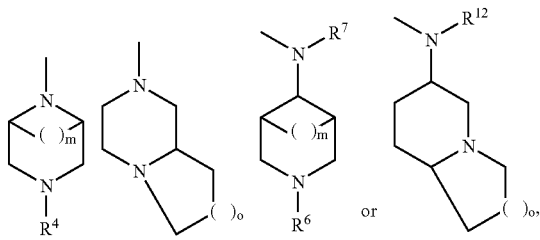

and $R^4$, $R^6$, $R^7$, $R^{12}$, m and o are as previously defined;

and pharmaceutically acceptable salts thereof.

According to a further aspect, the present invention includes compounds of Formula II(b):

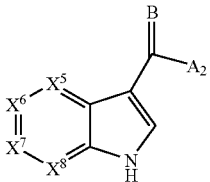
(IIb)

wherein
$X^5$ to $X^8$, and B are as defined previously;
$A_2$ is

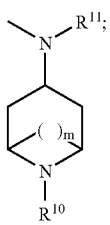

$R^{10}$ and $R^{11}$ are as defined previously; and
m is 1;

and pharmaceutically acceptable salts thereof.

According to a further aspect, the present invention includes compounds of Formula II(c):

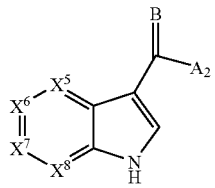
(IIc)

wherein
$X^5$ to $X^8$, and B are as defined previously;
$A_2$ is

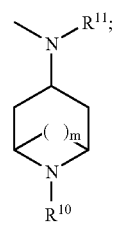

$R^{10}$, $R^{11}$ and m are as defined previously; and
$R^2$ is $C_{2-6}$-alkyl (e.g., $C_2H_5$) which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkenyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkynyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, $Si(R^{15})_3$, Ar, Het, or combinations thereof, $C_{3-8}$-cycloalkyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof, CN, $NO_2$, $NR^{13}R^{14}$, SH, $SR^{13}$, $SOR^{13}$, $SO_2R^{13}$, $SO_2NR^{13}R^{14}$, $NR^{13}SO_2R^{14}$, $CONR^{13}R^{14}$, $CSNR^{13}R^{14}$, $COOR^{13}$, $NR^{13}COR^{14}$, $NR^{13}CSR^{14}$, $NR^{13}CONR^{13}R^{14}$, $NR^{13}CSNR^{13}R^{14}$, $NR^{13}COOR^{14}$, $NR^{13}CSOR^{14}$, $OCONR^{13}R^{14}$, $OCSNR^{13}R^{14}$,
Ar,
Het, or
$R^{16}O$—; and pharmaceutically acceptable salts thereof.

According to a further aspect, the present invention includes compounds of Formula II(d):

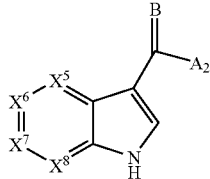
(IId)

wherein
$X^5$ to $X^8$ and B are as defined previously;
$A_2$ is

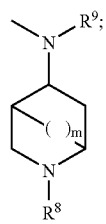

$R^8$ and $R^9$ are as defined previously; and
m is 1 or 3;

and pharmaceutically acceptable salts thereof.

According to a further aspect, the present invention includes compounds of Formula II(e):

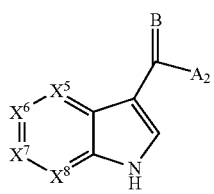
(IIe)

wherein
$X^5$ to $X^8$ and B are as defined previously;
$A_2$ is

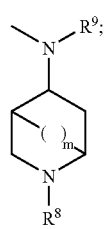

$R^8$, $R^9$ and m are as defined previously; and
$R^1$ is $C_{2-6}$-alkyl (e.g., $C_2H_5$) which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^3R^{14}$, Ar, Het, or combinations thereof, $C_{2-6}$-alkenyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, SOR , $C_{3-8}$-cycloalkyl, $SO_2R^{13}$, $SO_2NR^{13}R^{14}$, Ar, Het, or combinations thereof, $C_{2-6}$-alkynyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, $Si(R^{15})_3$, Ar, Het, or combinations thereof, $C_{3-8}$-cycloalkyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof, halogen (e.g., F, Cl, Br, I), CN, $NO_2$, $NR^{13}R^{14}$, SH, $SR^{13}$, $SOR^{13}$, $SO_2R^{13}$, $SO_2NR^{13}R^{14}$, $NR^{13}SO_2R^{14}$, $CONR^{13}R^{14}$, $CSNR^{13}R^{14}$, $COOR^{13}$, $NR^{13}COR^{14}$, $NR^{13}CSR^{16}$, $NR^{13}CONR^{13}R^{14}$, $NR^{13}CSNR^{13}R^{14}$, $NR^{13}COOR^{14}$, $NR^{13}CSOR^{14}$, $OCONR^{13}R^{14}$, $OCSNR^{13}R^{14}$, Ar,
Het, or
$R^{16}O$—; and pharmaceutically acceptable salts thereof.

According to a further aspect, the present invention includes compounds of Formula II(f):

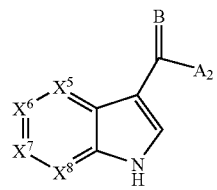
(IIf)

wherein
$X^5$ to $X^8$ and B are as defined previously;
$A_2$ is

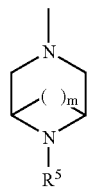

$R^5$ is as defined previously; and
m is 1;

and pharmaceutically acceptable salts thereof.

According to a further aspect, the present invention includes compounds of Formula II(g):

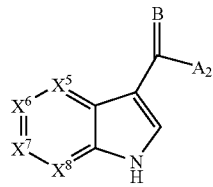
(IIg)

wherein $X^5$ to $X^8$ and B are as defined previously;

$A_2$ is

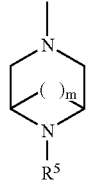

$R^5$ and m are as defined previously; and $R^1$ is $C_{2-6}$-alkyl (e.g., $C_2H_5$) which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkenyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkynyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, $C_{3-8}$-cycloalkyl, $SO_2R^{13}$, $SO_2NR^{13}R^{14}$, $Si(R^{15})_3$, Ar, Het, or combinations thereof, $C_{3-8}$-cycloalkyl which is unsubstituted or substituted one or more times by F, Cl, Br, I, CN, OH, alkoxy having 1 to 4 carbon atoms (e.g., $OCH_3$), $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof, halogen (e.g., F, Cl, Br, I), CN, $NO_2$, $NR^{13}R^{14}$, SH, $SR^{13}$, $SOR^{13}$, $SO_2R^{13}$, $SO_2NR^{13}R^{14}$, $NR^{13}SO_2R^{14}$, $CONR^{13}R^4$, $CSNR^{13}R^{14}$, $COOR^{13}$, $NR^{13}COR^{14}$, $NR^{13}CSR^{14}$, $NR^{13}CONR^{13}R^{14}$, $NR^{13}CSNR^{13}R^{14}$, $NR^{13}COOR^{14}$, $NR^{13}CSOR^{14}$, $OCONR^{13}R^{14}$, $OCSNR^{13}R^{14}$, Ar, Het, or $R^{16}O-$; and and pharmaceutically acceptable salts thereof.

According to a further aspect, the present invention includes compounds of Formula II(h):

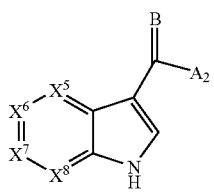

wherein $X^5$ to $X^8$, and $A_2$ are as defined previously; and

B is S; and pharmaceutically acceptable salts thereof.

According to a further aspect, the present invention includes compounds of Formula II(i):

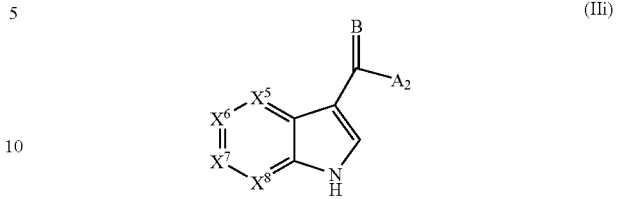

wherein $X^5$ to $X^8$, and $A_2$ are as defined previously; and

B is $H_2$; and pharmaceutically acceptable salts thereof.

According to a further aspect, the present invention includes compounds of Formula III(a):

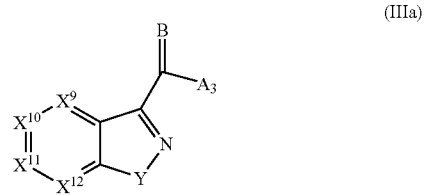

wherein $X^9$ to $X^{12}$, B and $A_3$ are as defined previously; and

Y is S;

and pharmaceutically acceptable salts thereof.

According to a further aspect, the present invention includes compounds of Formula III(b):

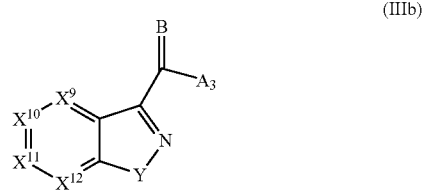

wherein $X^9$ to $X^{12}$, Y and $A_3$ are as defined previously; and

B is S or $H_2$;

and pharmaceutically acceptable salts thereof.

According to a further aspect, the present invention includes compounds of Formula III(c):

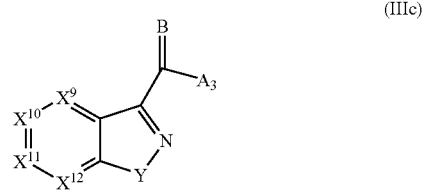

wherein
X$^9$ to X$^{12}$, B and Y are as defined previously; and
A$_3$ is

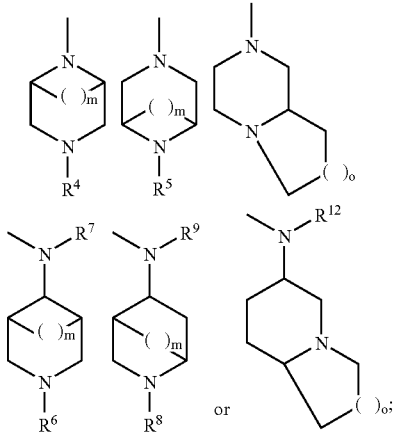

and R$^4$-R$^9$, R$^{12}$, m and o are as previously defined;

and pharmaceutically acceptable salts thereof.

According to a further aspect, the present invention includes compounds of Formula III(d):

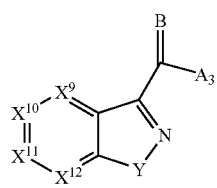
(IIId)

wherein
X$^9$ to X$^{12}$, B and Y are as defined previously; and
A$_3$ is

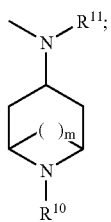

R$^{10}$ and R$^{11}$ are as defined previously; and
m is 1;

and pharmaceutically acceptable salts thereof.

According to a further aspect, the present invention includes compounds of Formula III(e):

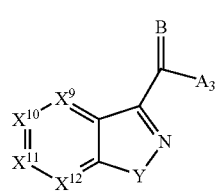
(IIIe)

wherein
X$^9$ to X$^{12}$, B and Y are as defined previously; and
A$_3$ is

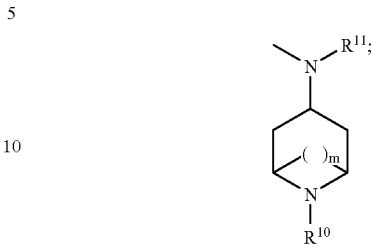

R$^{10}$, R$^{11}$ and m are as defined previously; and
R$^3$ is C$_{2-6}$-alkyl (e.g., C$_2$H$_5$) which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Ar, Het, or combinations thereof, C$_{2-6}$-alkenyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Ar, Het, or combinations thereof, C$_{2-6}$-alkynyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Si(R$^{15}$)$_3$, Ar, Het, or combinations thereof, C$_{3-8}$-cycloalkyl which is unsubstituted or substituted one or more times by F, Cl, Br, I, CN, OH, alkoxy having 1 to 4 carbon atoms (e.g., OCH$_3$), NR$^{13}$R$^{14}$, SH, SR$^{13}$, SOR$^{13}$, unsubstituted C$_{3-8}$-cycloalkyl, SO$_2$R$^{13}$, SO$_2$NR$^{13}$R$^{14}$, Ar, Het, or combinations thereof, CN, NR$^{13}$R$^{14}$ (wherein at least one of R$^{13}$ and R$^{14}$ is other than H), SH, SR$^{13}$, SOR$^{13}$, SO$_2$R$^{13}$, SO$_2$NR$^{13}$R$^{14}$, NR$^{13}$SO$_2$R$^{14}$, CONR$^{13}$R$^{14}$, CSNR$^{13}$R$^{14}$, COOR$^{13}$, NR$^{13}$COR$^{14}$, NR$^{13}$CSR$^{14}$, NR$^{13}$CONR$^{13}$R$^{14}$, NR$^{13}$CSNR$^{13}$R$^{14}$, NR$^{13}$COOR$^{14}$, NR$^{13}$CSOR$^{14}$, OCONR$^{13}$R$^{14}$, OCSNR$^{13}$R$^{14}$, Ar,
Het, or
R$^{16}$O—; and pharmaceutically acceptable salts thereof.

Alkyl throughout means a straight-chain or branched-chain aliphatic hydrocarbon radical having preferably 1 to 4 carbon atoms. Suitable alkyl groups include, but are not limited to, methyl, ethyl, propyl, isopropyl, butyl, sec-butyl, and tert-butyl.

Alkoxy means alkyl-O-groups in which the alkyl portion preferably has 1 to 4 carbon atoms. Suitable alkoxy groups include, but are not limited to, methoxy, ethoxy, propoxy, isopropoxy, isobutoxy, and sec-butoxy.

Cycloalkyl means a cyclic, bicyclic or tricyclic saturated hydrocarbon radical having 3 to 8 carbon atoms. Suitable cycloalkyl groups include, but are not limited to, cyclopropyl, cyclobutyl, cyclopentyl, and cyclohexyl. Other suitable cycloalkyl groups include spiropentyl, bicyclo[2.1.0]pentyl, and bicyclo[3.1.0]hexyl.

The cycloalkyl groups can be substituted by C$_{1-4}$-alkyl, C$_{1-4}$-alkoxy, hydroxyl, amino, monoalkylamino having 1 to 4 carbon atoms, and/or dialklyamino in which each alkyl group has 1 to 4 carbon atoms.

Cycloalkylalkyl refers to cycloalkyl-alkyl radicals in which the cycloalkyl and alkyl portions are in accordance with previous discussions. Suitable examples include, but are not limited to, cyclopropylmethyl and cyclopentylmethyl.

Aryl, as a group or substituent per se or as part of a group or substituent, refers to an aromatic carbocyclic radical containing 6 to 10 carbon atoms, unless indicated otherwise. Suitable aryl groups include, but are not limited to, phenyl, napthyl and biphenyl. Substituted aryl groups include the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Arylalkyl refers to an aryl-alkyl-radical in which the aryl and alkyl portions are in accordance with the previous descriptions. Suitable examples include, but are not limited to, benzyl, 1-phenethyl, 2-phenethyl, phenpropyl, phenbutyl, phenpentyl, and napthylmethyl.

Heterocyclic groups refer to saturated, partially saturated and fully unsaturated heterocyclic groups having one, two or three rings and a total number of 5 to 10 ring atoms wherein at least one of the ring atoms is an N, O or S atom. Preferably, the heterocyclic group contains 1 to 3 hetero-ring atoms selected from N, O and S. Suitable saturated and partially saturated heterocyclic groups include, but are not limited to, tetrahydrofuranyl, tetrahydrothienyl, dihydropyranyl, pyrrolidinyl, piperidinyl, piperazinyl, morpholinyl, isoxazolinyl and the like. Suitable heteroaryl groups include but are not limited to furyl, thienyl, pyrrolyl, pyrazolyl, imidazolyl, pyridyl, pyrimidinyl, benzopyranyl, indolyl, quinolinyl, isoquinolinyl, naphthyridinyl, oxazolyl, triazolyl and the like. Other non-limiting examples of suitable heterocyclic groups include 2-quinolinyl, 1,3-benzodioxyl, 2-thienyl, 2-benzofuranyl, 2-benzothiophenyl, 3-thienyl, 2,3-dihydro-5-benzofuranyl, 4-indoyl, 4-pyridyl, 3-quinolinyl, 4-quinolinyl, 1,4-benzodioxan-6-yl, 3-indoyl, 2-pyrrolyl, benzopyran-6-yl, 5-indolyl, 1,5-benzoxepin-8-yl, 3-pyridyl, 6-coumarinyl, 5-benzofuranyl, 2-isoimidazol-4-yl, 3-pyrazolyl, and 3-carbazolyl.

Substituted heterocyclic groups refer to the heterocyclic groups described above, which are substituted in one or more places by, for example, halogen, aryl, alkyl, alkoxy, cyano, trifluoromethyl, nitro, oxo, amino, alkylamino, and dialkylamino.

Radicals which are substituted one or more times preferably have 1 to 3 substituents, especially 1 or 2 substituents of the exemplified substituents. Halogenated radicals such as halogenated alkyls are preferably fluorinated and include perhalo radicals such as trifluoromethyl.

In the compounds of Formulas I-III, $R^1$, $R^2$ and $R^3$ are each preferably H, alkyl, halogenated alkyl (e.g., $CF_3$), $OR^{16}$ (such as alkoxy (e.g., $OCH_3$) and halogenated alkoxy (e.g., $OCF_3$, $OCHF_2$)), halogen (such as Br), Ar such as, but not limited to, substituted or unsubstituted phenyl (e.g., fluorophenyl methoxyphenyl, and trifluorophenyl) or Het, such as, but not limited to, substituted or unsubstituted thienyl, substituted or unsubstituted furyl, substituted or unsubstituted pyrazolyl, substituted or unsubstituted thiazolyl, substituted or unsubstituted dihydropyranyl, substituted or unsubstituted oxazolyl, substituted or unsubstituted triazolyl, substituted or unsubstituted imidazolyl, and substituted or unsubstituted isoxazolyl. Suitable examples of Het include, but are not limited to, 2-thienyl, 3-thienyl, 2-(4-methyl)thienyl, 2-(5-methyl)thienyl), 2-oxazolyl, (trifluoromethylphenyl)thienyl, 2-(4-methyl)thiazolyl, (3,6-dihydro-2H-pyran-4-yl), (1-benzyl-1H-1,2,3-triazol-4-yl), 2-oxo-3-propylimidazolidin-1-yl), dimethylisoxazolyl, 1-benzyl-1H-pyrazol-4-yl, 2-furyl, 3-furyl, and 2-(5-methyl)furyl).

$X^1$ to $X^4$ are each preferably CH or $CR^1$. $X^5$ to $X^8$ are each preferably CH or $CR^2$. $X^9$ to $X^{12}$ are each preferably CH or $CR^3$. $X^1$, $X^5$, and $X^9$ are each preferably CH. $X^4$ is preferably CH or $CR^1$ wherein $R^1$ is alkyl, halogenated alkyl, alkoxy, halogenated alkoxy, or halogen. $X^8$ is preferably CH or $CR^2$ wherein $R^2$ is alkyl, halogenated alkyl, alkoxy, halogenated alkoxy, or halogen. $X^{12}$ is preferably CH or $CR^3$ wherein $R^3$ is alkyl, halogenated alkyl, alkoxy, halogenated alkoxy, or halogen. $X^2$ and $X^3$ are each preferably CH or $CR^1$ wherein $R^1$ is alkyl, halogenated alkyl, alkoxy, halogenated alkoxy, halogen, cyano, alkynyl, cycloalkyl, cycloalkyloxy, cycloalkylalkoxy, Ar or Het. $X^6$ and $X^7$ are each preferably CH or $CR^2$ wherein $R^2$ is alkyl, halogenated alkyl, alkoxy, halogenated alkoxy, halogen, cyano, alkynyl, cycloalkyl, cycloalkyloxy, cycloalkylalkoxy, Ar or Het. $X^{10}$ and $X^{11}$ are each preferably CH or $CR^3$ wherein $R^3$ is alkyl, halogenated alkyl, alkoxy, halogenated alkoxy, halogen, cyano, alkynyl, cycloalkyl, cycloalkyloxy, cycloalkylalkoxy, Ar or Het.

$R^7$, $R^9$, $R^{11}$, and $R^{12}$ are each preferably H or alkyl (e.g., $CH_3$).

$R^4$, $R^5$, $R^6$, $R^8$, and $R^{10}$ are each preferably H, alkyl (e.g., $CH_3$ or $C_2H_5$), cycloalkylalkyl (e.g., cyclopropylmethyl) or Ar-alkyl (e.g., benzyl).

In the compounds of formula I, $A_1$ is preferably selected from 8-methyl-8-azabicyclo[3.2.1]octan-3-amino (endo and/or exo), octahydropyrrolo[1,2-a]pyrazinyl, 3-methyl-3,8-diazabicyclo[3.2.1]octan-8-amino, 8-methyl-3,8-diazabicyclo[3.2.1]oct-3-yl, 9-methyl-9-azabicyclo[3.3.1]nonan-3-amino (endo and/or exo), 2-methyl-2-azabicyclo[2.2.2]octan-5-amino, (rel 6R,8aS)-octahydroindolizin-6-amino, (rel 6S,8aS)-octahydroindolizin-6-amino, 2-azabicyclo[2.2.1]heptan-5-amino, and 8-azabicyclo[3.2.1]octan-3-amino.

In the compounds of formula II, $A_2$ is preferably 8-methyl-8-azabicyclo[3.2.1]octan-3-amino (endo and/or exo).

In the compounds of formula III, $A_3$ is preferably selected from 8-methyl-8-azabicyclo[3.2.1]octan-3-amino (endo and/or exo), 8-methyl-3,8-diazabicyclo[3.2.1]octan-3-amino, 2-methyl-2-azabicyclo[2.2.2]octan-5-amino, and 9-methyl-9-azabicyclo[3.3.1]nonan-3-amino(endo and/or exo).

According to a further aspect of the invention, the compounds are of formula I in which $A_1$ is 8-azabicyclo[3.2.1]octan-3-amino, 8-methyl-8-azabicyclo[3.2.1]octan-3-amino (endo and/or exo), 9-azabicyclo[3.3.1]nonan-3-amino, or 9-methyl-9-azabicyclo[3.3.1]non-3-amino (endo and/or exo); B is O; $R^{11}$ is H or $CH_3$; and $R^1$ is $CF_3$, $CH_3O$, $CF_3O$, cyclopropyl, cyano, ethynyl which is substituted or unsubstituted, phenyl which is substituted or unsubstituted, furyl which is substituted or unsubstituted, thienyl which is substituted or unsubstituted, bithienyl which is substituted or unsubstituted, pyrazolyl which is substituted or unsubstituted, thiazolyl which is substituted or unsubstituted, imidazolyl which is substituted or unsubstituted, pyrrolidinyl which is substituted or unsubstituted, morpholinyl which is substituted or unsubstituted, or thiomorpholinyl which is substituted or unsubstituted According to a further aspect of the invention, the compounds are of formula I in which $A_1$ is 2-azabicyclo[2.2.1]heptan-5-amino, 2-methyl-2-azabicyclo[2.2.1]heptan-5-amino, 2-azabicyclo[2.2.2]octan-5-amino, and 2-methyl-2-azabicyclo[2.2.2]octan-5-amino; B is O; and $R^{11}$ is H or $CH_3$.

According to a further aspect of the invention, the compounds are of formula I in which $A_1$ is 3,8-diazabicyclo[3.2.1]

octan-8-amino, 3-methyl-3,8-diazabicyclo[3.2.1]octan-8-amino or 8-methyl-3,8-diazabicyclo[3.2.1]octan-8-amino; and B is O.

According to a further aspect, compounds in accordance with formulas I, II, or III (without the proviso clauses) in which $R^1$-$R^3$ are Br are particularly useful as intermediates for production of other compounds of Formulas I, II, or III. See, e.g., the compounds of Examples 10, 19, and 21.

In addition, preferred inhibitors in accordance with the invention are compounds described by subformulas I'a-I'f, II'a-II'f, and III'a-III'f which correspond, respectively, to Formulas I, II, or III but exhibit the following preferred groups:

I'a $X^1$, $X^2$ and $X^3$ are each CH;
$X^4$ is $CR^1$; and
B is O.

I'b $X^1$, $X^2$ and $X^4$ are each CH;
$X^3$ is $CR^1$; and
B is O.

I'c $X^1$, $X^3$ and $X^4$ are each CH;
$X^2$ is $CR^1$; and
B is O.

I'd $X^1$, $X^2$ and $X^3$ are each CH;
$X^4$ is $CR^1$;
B is O; and
$R^1$ is alkyl, halogenated alkyl, alkoxy, halogenated alkoxy, or halogen.

I'e $X^1$, $X^2$ and $X^4$ are each CH;
$X^3$ is $CR^1$;
B is O; and
$R^1$ is alkyl, halogenated alkyl, alkoxy, halogenated alkoxy, halogen, Ar or Het.

I'f $X^1$, $X^3$ and $X^4$ are each CH;
$X^2$ is $CR^1$;
B is O; and
$R^1$ is alkyl, halogenated alkyl, alkoxy, halogenated alkoxy, halogen, Ar or Het.

II'a $X^5$, $X^6$ and $X^7$ are each CH;
$X^8$ is $CR^2$; and
B is O.

II'b $X^5$, $X^6$ and $X^8$ are each CH;
$X^7$ is $CR^2$; and
B is O.

II'c $X^5$, $X^7$ and $X^8$ are each CH;
$X^6$ is $CR^2$; and
B is O.

II'd $X^5$, $X^6$ and $X^7$ are each CH;
$X^8$ is $CR^2$;
B is O; and
$R^2$ is alkyl, halogenated alkyl, alkoxy, halogenated alkoxy, or halogen.

II'e $X^5$, $X^6$ and $X^8$ are each CH;
$X^7$ is $CR^2$;
B is O; and
$R^2$ is alkyl, halogenated alkyl, alkoxy, halogenated alkoxy, halogen, Ar or Het.

II'f $X^5$, $X^7$ and $X^8$ are each CH;
$X^6$ is $CR^2$;
B is O; and
$R^2$ is alkyl, halogenated alkyl, alkoxy, halogenated alkoxy, halogen, Ar or Het.

III'a $X^9$, $X^{10}$ and $X^{11}$ are each CH;
$X^2$ is $CR^3$; and
B is O.

III'b $X^9$, $X^{10}$ and $X^{12}$ are each CH;
$X^{11}$ is $CR^3$; and
B is O.

III'c $X^9$, $X^{11}$ and $X^{12}$ are each CH;
$X^{10}$ is $CR^3$; and
B is O.

III'd $X^9$, $X^{10}$ and $X^{11}$ are each CH;
$X^{12}$ is $CR^3$;
B is O; and
$R^3$ is alkyl, halogenated alkyl, alkoxy, halogenated alkoxy, or halogen.

III'e $X^9$, $X^{11}$ and $X^{12}$ are each CH;
$X^{11}$ is $CR^3$;
B is O; and
$R^3$ is alkyl, halogenated alkyl, alkoxy, halogenated alkoxy, halogen, Ar or Het.

III'f $X^9$, $X^{11}$ and $X^{12}$ are each CH;
$X^{10}$ is $CR^3$;
B is O; and
$R^3$ is alkyl, halogenated alkyl, alkoxy, halogenated alkoxy, halogen, Ar or Het.

According to a compound and/or method aspect of the invention, the compounds are selected from:

(8-Methyl-8-azabicyclo[3.2.1]non-3-yl)-6-(2-thienyl)-1H-indazole-3-carboxamide hydroformate,
(8-Methyl-8-azabicyclo[3.2.1]non-3-yl)-6-(2-thienyl)-1H-indazole-3-carboxamide,
3-(Hexahydropyrrolo[1,2-a]pyrazin-2(1H)-ylcarbonyl)-1H-indazole hydroformate,
3-(Hexahydropyrrolo[1,2-a]pyrazin-2(1H)-ylcarbonyl)-1H-indazole,
3-[(3-Methyl-3,8-diazabicyclo[3.2.1]oct-8-yl)carbonyl]-1H-indazole hydroformate,
3-[(3-Methyl-3,8-diazabicyclo[3.2.1]oct-8-yl)carbonyl]-1H-indazole,
3-[(8-Methyl-3,8-diazabicyclo[3.2.1]oct-3-yl)carbonyl]-1H-indazole hydroformate,
3-[(8-Methyl-3,8-diazabicyclo[3.2.1]oct-3-yl)carbonyl]-1H-indazole,
3-[(8-Methyl-3,8-diazabicyclo[3.2.1]oct-3-yl)carbonyl]-5-(trifluoromethoxy)-1H-indazole hydroformate,
3-[(8-Methyl-3,8-diazabicyclo[3.2.1]oct-3-yl)carbonyl]-5-(trifluoromethoxy)-1H-indazole,
5-(1-Benzyl-1H-pyrazol-4-yl)-N-(9-methyl-9-azabicyclo[3.3.1]non-3-yl)-1H-indazole-3-carboxamide hydroformate,
5-(1-Benzyl-1H-pyrazol-4-yl)-N-(9-methyl-9-azabicyclo[3.3.1]non-3-yl)-1H-indazole-3-carboxamide,
5-(2,3'-Bithien-5-yl)-N-(9-methyl-9-azabicyclo[3.3.1]non-3-yl)-1H-indazole-3-carboxamide hydroformate,
5-(2,3'-Bithien-5-yl)-N-(9-methyl-9-azabicyclo[3.3.1]non-3-yl)-1H-indazole-3-carboxamide,
5-(2-Furyl)-N-(8-methyl-8-azabicyclo[3.2.1]oct-3-yl)-1H-indazole-3-carboxamide,
5-(3,5-Dimethylisoxazol-4-yl)-N-(8-methyl-8-azabicyclo[3.2.1]oct-3-yl)-1H-indazole-3-carboxamide hydroformate,
5-(3,5-Dimethylisoxazol-4-yl)-N-(8-methyl-8-azabicyclo[3.2.1]oct-3-yl)-1H-indazole-3-carboxamide,
5-(3-Furyl)-N-(8-methyl-8-azabicyclo[3.2.1]oct-3-yl)-1H-indazole-3-carboxamide hydroformate,
5-(3-Furyl)-N-(8-methyl-8-azabicyclo[3.2.1]oct-3-yl)-1H-indazole-3-carboxamide,
5-(3-Furyl)-N-(9-methyl-9-azabicyclo[3.3.1]non-3-yl)-1H-indazole-3-carboxamide hydroformate,
5-(3-Furyl)-N-(9-methyl-9-azabicyclo[3.3.1]non-3-yl)-1H-indazole-3-carboxamide,
5-(4-Fluorophenyl)-N-(8-methyl-8-azabicyclo[3.2.1]oct-3-yl)-1H-indazole-3-carboxamide hydroformate, 5-(4-Fluorophenyl)-N-(8-methyl-8-azabicyclo[3.2.1]oct-3-yl)-1H-indazole-3-carboxamide,
5-Bromo-N-(8-methyl-8-azabicyclo[3.2.1]oct-3-yl)-1H-indazole-3-carboxamide,
5-Cyano-N-(8-methyl-8-azabicyclo[3.2.1]oct-3-yl)-1H-indazole-3-carboxamide hydroformate,
5-Cyano-N-(8-methyl-8-azabicyclo[3.2.1]oct-3-yl)-1H-indazole-3-carboxamide,
5-Ethynyl-N-(8-methyl-8-azabicyclo[3.2.1]oct-3-yl)-1H-indazole-3-carboxamide,
5-Methoxy-3-[(8-methyl-3,8-diazabicyclo[3.2.1]oct-3-yl)carbonyl]-1H-indazole hydroformate,
5-Methoxy-3-[(8-methyl-3,8-diazabicyclo[3.2.1]oct-3-yl)carbonyl]-1H-indazole,
5-Methoxy-N-(8-methyl-8-azabicyclo[3.2.1]oct-3-yl)-1H-indazole-3-carboxamide hydroformate,
5-Methoxy-N-(8-methyl-8-azabicyclo[3.2.1]oct-3-yl)-1H-indazole-3-carboxamide,
5-Methoxy-N-(9-methyl-9-azabicyclo[3.3.1]non-3-yl)-1H-indazole-3-carboxamide hydroformate,
5-Methoxy-N-(9-methyl-9-azabicyclo[3.3.1]non-3-yl)-1H-indazole-3-carboxamide,
5-Methoxy-N-methyl-N-(8-methyl-8-azabicyclo[3.2.1]oct-3-yl)-1H-indazole-3-carboxamide hydroformate,
5-Methoxy-N-methyl-N-(8-methyl-8-azabicyclo[3.2.1]oct-3-yl)-1H-indazole-3-carboxamide,
6-(2-Furyl)-N-(8-methyl-8-azabicyclo[3.2.1]oct-3-yl)-1H-indazole-3-carboxamide hydroformate,
6-(2-Furyl)-N-(8-methyl-8-azabicyclo[3.2.1]oct-3-yl)-1H-indazole-3-carboxamide,
6-(3-Furyl)-N-(8-methyl-8-azabicyclo[3.2.1]oct-3-yl)-1H-indazole-3-carboxamide,
6-(4-Fluorophenyl)-N-(8-methyl-8-azabicyclo[3.2.1]oct-3-yl)-1H-indazole-3-carboxamide hydroformate,
6-(4-Fluorophenyl)-N-(8-methyl-8-azabicyclo[3.2.1]oct-3-yl)-1H-indazole-3-carboxamide,
6-Bromo-N-(8-methyl-8-azabicyclo[3.2.1]oct-3-yl)-1H-indazole-3-carboxamide,
6-Bromo-N-(9-methyl-9-azabicyclo[3.3.1]non-3-yl)-1H-indazole-3-carboxamide hydroformate,
6-Bromo-N-(9-methyl-9-azabicyclo[3.3.1]non-3-yl)-1H-indazole-3-carboxamide,
6-Cyano-N-(8-methyl-8-azabicyclo[3.2.1]oct-3-yl)-1H-indazole-3-carboxamide hydroformate,
6-Cyano-N-(8-methyl-8-azabicyclo[3.2.1]oct-3-yl)-1H-indazole-3-carboxamide,
6-Cyclopropyl-N-(8-methyl-8-azabicyclo[3.2.1]oct-3-yl)-1,2-benzisothiazole-3-carboxamide hydroformate,
6-Cyclopropyl-N-(8-methyl-8-azabicyclo[3.2.1]oct-3-yl)-1,2-benzisothiazole-3-carboxamide,
6-Ethoxy-N-(8-methyl-8-azabicyclo[3.2.1]oct-3-yl)-1,2-benzisothiazole-3-carboxamide hydroformate,
6-Ethoxy-N-(8-methyl-8-azabicyclo[3.2.1]oct-3-yl)-1,2-benzisothiazole-3-carboxamide,
6-Methoxy-3-[(8-methyl-3,8-diazabicyclo[3.2.1]oct-3-yl)carbonyl]-1,2-benzisothiazole hydroformate,
6-Methoxy-3-[(8-methyl-3,8-diazabicyclo[3.2.1]oct-3-yl)carbonyl]-1,2-benzisothiazole,
6-Methoxy-3-[(8-methyl-3,8-diazabicyclo[3.2.1]oct-3-yl)carbonyl]-1H-indazole hydroformate,
6-Methoxy-3-[(8-methyl-3,8-diazabicyclo[3.2.1]oct-3-yl)carbonyl]-1H-indazole,
6-Methoxy-N-(2-methyl-2-azabicyclo[2.2.2]oct-5-yl)-1,2-benzisothiazole-3-carboxamide,
6-Methoxy-N-(8-methyl-8-azabicyclo[3.2.1]oct-3-yl)-1,2-benzisothiazole-3-carboxamide hydrochloride,
6-Methoxy-N-(8-methyl-8-azabicyclo[3.2.1]oct-3-yl)-1,2-benzisothiazole-3-carboxamide,
6-Methoxy-N-(9-methyl-9-azabicyclo[3.3.1]non-3-yl)-1,2-benzisothiazole-3-carboxamide,
6-Methoxy-N-(9-methyl-9-azabicyclo[3.3.1]non-3-yl)-1H-indazole-3-carboxamide,
6-Methoxy-N-(endo-8-methyl-8-azabicyclo[3.2.1]oct-3-yl)-1H-indazole-3-carboxamide,
7-Methoxy-N-(8-methyl-8-azabicyclo[3.2.1]oct-3-yl)-1,2-benzisothiazole-3-carboxamide hydroformate,
7-Methoxy-N-(8-methyl-8-azabicyclo[3.2.1]oct-3-yl)-1,2-benzisothiazole-3-carboxamide,
7-Methoxy-N-(9-methyl-9-azabicyclo[3.3.1]non-3-yl)-1H-indazole-3-carboxamide hydroformate,
7-Methoxy-N-(9-methyl-9-azabicyclo[3.3.1]non-3-yl)-1H-indazole-3-carboxamide,
8-Methyl-N-{[5-(3-thienyl)-1H-indazol-3-yl]methyl}-8-azabicyclo[3.2.1]octan-3-amine hydroformate,
8-Methyl-N-{[5-(3-thienyl)-1H-indazol-3-yl]methyl}-8-azabicyclo[3.2.1]octan-3-amine,
N-(2-Azabicyclo[2.2.1]hept-5-yl)-1H-indazole-3-carboxamide,
N-(2-Cyclopropylmethyl-2-azabicyclo[2.2.1]hept-5-yl)-1H-indazole-3-carboxamide hydroformate,
N-(2-Cyclopropylmethyl-2-azabicyclo[2.2.1]hept-5-yl)-1H-indazole-3-carboxamide,
N-(2-Ethyl-2-azabicyclo[2.2.1]hept-5-yl)-1H-indazole-3-carboxamide hydroformate,
N-(2-Ethyl-2-azabicyclo[2.2.1]hept-5-yl)-1H-indazole-3-carboxamide,
N-(2-Methyl-2-azabicyclo[2.2.1]hept-5-yl)-1H-indazole-3-carboxamide hydroformate,
N-(2-Methyl-2-azabicyclo[2.2.1]hept-5-yl)-1H-indazole-3-carboxamide,
N-(2-Methyl-2-azabicyclo[2.2.2]oct-5-yl)-1H-indazole-3-carboxamide,
N-(8-Azabicyclo[3.2.1]oct-3-yl)-1H-indazole-3-carboxamide hydrochloride,
N-(8-Azabicyclo[3.2.1]oct-3-yl)-1H-indazole-3-carboxamide,
N-(8-Methyl-8-azabicyclo[3.2.1]oct-3-yl)-1,2-benzisothiazole-3-carboxamide,
N-(8-Methyl-8-azabicyclo[3.2.1]oct-3-yl)-1H-indazole-3-carboxamide hydroformate,
N-(8-Methyl-8-azabicyclo[3.2.1]oct-3-yl)-1H-indazole-3-carboxamide,
N-(8-Methyl-8-azabicyclo[3.2.1]oct-3-yl)-5-(1,3-thiazol-2-yl)-1H-indazole-3-carboxamide hydroformate,
N-(8-Methyl-8-azabicyclo[3.2.1]oct-3-yl)-5-(1,3-thiazol-2-yl)-1H-indazole-3-carboxamide,
N-(8-Methyl-8-azabicyclo[3.2.1]oct-3-yl)-5-(1-methyl-1H-imidazol-2-yl)-1H-indazole-3-carboxamide hydroformate,
N-(8-Methyl-8-azabicyclo[3.2.1]oct-3-yl)-5-(1-methyl-1H-imidazol-2-yl)-1H-indazole-3-carboxamide,
N-(8-Methyl-8-azabicyclo[3.2.1]oct-3-yl)-5-(2-thienyl)-1H-indazole-3-carboxamide,
N-(8-Methyl-8-azabicyclo[3.2.1]oct-3-yl)-5-(2-trimethylsilylethynyl)-1H-indazole-3-carboxamide,
N-(8-Methyl-8-azabicyclo[3.2.1]oct-3-yl)-5-(3-thienyl)-1H-indazole-3-carbothioamide hydroformate,
N-(8-Methyl-8-azabicyclo[3.2.1]oct-3-yl)-5-(3-thienyl)-1H-indazole-3-carbothioamide,
N-(8-Methyl-8-azabicyclo[3.2.1]oct-3-yl)-5-(3-thienyl)-1H-indazole-3-carboxamide hydroformate,
N-(8-Methyl-8-azabicyclo[3.2.1]oct-3-yl)-5-(3-thienyl)-1H-indazole-3-carboxamide, N-(8-Methyl-8-azabicyclo[3.2.1]oct-3-yl)-5-(5-methyl-2-thienyl)-1H-indazole-3-carboxamide hydroformate,
N-(8-Methyl-8-azabicyclo[3.2.1]oct-3-yl)-5-(5-methyl-2-thienyl)-1H-indazole-3-carboxamide,
N-(8-Methyl-8-azabicyclo[3.2.1]oct-3-yl)-5-(morpholin-4-yl)-1H-indazole-3-carboxamide hydroformate,
N-(8-Methyl-8-azabicyclo[3.2.1]oct-3-yl)-5-(morpholin-4-yl)-1H-indazole-3-carboxamide,
N-(8-Methyl-8-azabicyclo[3.2.1]oct-3-yl)-5-(pyrrolidin-1-yl)-1H-indazole-3-carboxamide hydroformate,
N-(8-Methyl-8-azabicyclo[3.2.1]oct-3-yl)-5-(pyrrolidin-1-yl)-1H-indazole-3-carboxamide,
N-(8-Methyl-8-azabicyclo[3.2.1]oct-3-yl)-5-(thiomorpholin-4-yl)-1H-indazole-3-carboxamide hydroformate,
N-(8-Methyl-8-azabicyclo[3.2.1]oct-3-yl)-5-(thiomorpholin-4-yl)-1H-indazole-3-carboxamide,
N-(8-Methyl-8-azabicyclo[3.2.1]oct-3-yl)-5-(trifluoromethoxy)-1H-indazole-3-carboxamide hydroformate,
N-(8-Methyl-8-azabicyclo[3.2.1]oct-3-yl)-5-(trifluoromethoxy)-1H-indazole-3-carboxamide,
N-(8-Methyl-8-azabicyclo[3.2.1]oct-3-yl)-5-[(3-trifluoromethyl)phenyl]-1H-indazole-3-carboxamide hydroformate,
N-(8-Methyl-8-azabicyclo[3.2.1]oct-3-yl)-5-[(3-trifluoromethyl)phenyl]-1H-indazole-3-carboxamide,
N-(8-Methyl-8-azabicyclo[3.2.1]oct-3-yl)-5-[(4-trifluoromethyl)phenyl]-1H-indazole-3-carboxamide hydroformate,
N-(8-Methyl-8-azabicyclo[3.2.1]oct-3-yl)-5-[(4-trifluoromethyl)phenyl]-1H-indazole-3-carboxamide,
N-(8-Methyl-8-azabicyclo[3.2.1]oct-3-yl)-5-{5-[3-(trifluoromethyl)phenyl]-2-thienyl}-1H-indazole-3-carboxamide hydroformate,
N-(8-Methyl-8-azabicyclo[3.2.1]oct-3-yl)-5-{5-[3-(trifluoromethyl)phenyl]-2-thienyl}-1H-indazole-3-carboxamide,
N-(8-Methyl-8-azabicyclo[3.2.1]oct-3-yl)-6-(1,3-thiazol-2-yl)-1H-indazole-3-carboxamide hydroformate,
N-(8-Methyl-8-azabicyclo[3.2.1]oct-3-yl)-6-(1,3-thiazol-2-yl)-1H-indazole-3-carboxamide,
N-(8-Methyl-8-azabicyclo[3.2.1]oct-3-yl)-6-(1-methyl-1H-imidazol-2-yl)-1H-indazole-3-carboxamide dihydrochloride,
N-(8-Methyl-8-azabicyclo[3.2.1]oct-3-yl)-6-(1-methyl-1H-imidazol-2-yl)-1H-indazole-3-carboxamide,
N-(8-Methyl-8-azabicyclo[3.2.1]oct-3-yl)-6-(2-trimethylsilyethynyl)-1H-indazole-3-carboxamide hydroformate,
N-(8-Methyl-8-azabicyclo[3.2.1]oct-3-yl)-6-(2-trimethylsilyethynyl)-1H-indazole-3-carboxamide,
N-(8-Methyl-8-azabicyclo[3.2.1]oct-3-yl)-6-(3-thienyl)-1H-indazole-3-carboxamide,
N-(8-Methyl-8-azabicyclo[3.2.1]oct-3-yl)-6-(5-methyl-2-thienyl)-1H-indazole-3-carboxamide hydroformate,
N-(8-Methyl-8-azabicyclo[3.2.1]oct-3-yl)-6-(5-methyl-2-thienyl)-1H-indazole-3-carboxamide,
N-(8-Methyl-8-azabicyclo[3.2.1]oct-3-yl)-6-(trifluoromethoxy)-1H-indazole-3-carboxamide hydroformate,
N-(8-Methyl-8-azabicyclo[3.2.1]oct-3-yl)-6-(trifluoromethoxy)-1H-indazole-3-carboxamide,
N-(8-Methyl-8-azabicyclo[3.2.1]oct-3-yl)-6-[(3-trifluoromethyl)phenyl]-1H-indazole-3-carboxamide hydroformate,
N-(8-Methyl-8-azabicyclo[3.2.1]oct-3-yl)-6-[(3-trifluoromethyl)phenyl]-1H-indazole-3-carboxamide,
N-(8-Methyl-8-azabicyclo[3.2.1]oct-3-yl)-6-[(4-trifluoromethyl)phenyl]-1H-indazole-3-carboxamide hydroformate,
N-(8-Methyl-8-azabicyclo[3.2.1]oct-3-yl)-6-[(4-trifluoromethyl)phenyl]-1H-indazole-3-carboxamide,
N-(8-Methyl-8-azabicyclo[3.2.1]oct-3-yl)-7-(trifluoromethoxy)-1H-indazole-3-carboxamide hydroformate,
N-(8-Methyl-8-azabicyclo[3.2.1]oct-3-yl)-7-(trifluoromethoxy)-1H-indazole-3-carboxamide,
N-(9-Methyl-9-azabicyclo[3.3.1]non-3-yl)-1H-indazole-3-carboxamide hydroformate,
N-(9-Methyl-9-azabicyclo[3.3.1]non-3-yl)-1H-indazole-3-carboxamide,
N-(9-Methyl-9-azabicyclo[3.3.1]non-3-yl)-5-(1,3-thiazol-2-yl)-1H-indazole-3-carboxamide hydroformate,
N-(9-Methyl-9-azabicyclo[3.3.1]non-3-yl)-5-(1,3-thiazol-2-yl)-1H-indazole-3-carboxamide,
N-(9-Methyl-9-azabicyclo[3.3.1]non-3-yl)-5-(1-methyl-1H-imidazol-2-yl)-1H-indazole-3-carboxamide dihydroformate,
N-(9-Methyl-9-azabicyclo[3.3.1]non-3-yl)-5-(1-methyl-1H-imidazol-2-yl)-1H-indazole-3-carboxamide,
N-(9-Methyl-9-azabicyclo[3.3.1]non-3-yl)-5-(2-trimethylsilyethynyl)-1H-indazole-3-carboxamide
N-(9-Methyl-9-azabicyclo[3.3.1]non-3-yl)-5-(3-thienyl)-1H-indazole-3-carboxamide hydroformate,
N-(9-Methyl-9-azabicyclo[3.3.1]non-3-yl)-5-(3-thienyl)-1H-indazole-3-carboxamide,
N-(9-Methyl-9-azabicyclo[3.3.1]non-3-yl)-5-(4-methyl-2-thienyl)-1H-indazole-3-carboxamide hydroformate,
N-(9-Methyl-9-azabicyclo[3.3.1]non-3-yl)-5-(4-methyl-2-thienyl)-1H-indazole-3-carboxamide,
N-(9-Methyl-9-azabicyclo[3.3.1]non-3-yl)-5-(morpholin-4-yl)-1H-indazole-3-carboxamide hydroformate,
N-(9-Methyl-9-azabicyclo[3.3.1]non-3-yl)-5-(morpholin-4-yl)-1H-indazole-3-carboxamide,
N-(9-Methyl-9-azabicyclo[3.3.1]non-3-yl)-5-(pyrrolidin-1-yl)-1H-indazole-3-carboxamide hydroformate,
N-(9-Methyl-9-azabicyclo[3.3.1]non-3-yl)-5-(pyrrolidin-1-yl)-1H-indazole-3-carboxamide,
N-(9-Methyl-9-azabicyclo[3.3.1]non-3-yl)-5-(thiomorpholin-4-yl)-1H-indazole-3-carboxamide hydroformate,
N-(9-Methyl-9-azabicyclo[3.3.1]non-3-yl)-5-(thiomorpholin-4-yl)-1H-indazole-3-carboxamide,
N-(9-Methyl-9-azabicyclo[3.3.1]non-3-yl)-5-(trifluoromethoxy)-1H-indazole-3-carboxamide hydroformate,
N-(9-Methyl-9-azabicyclo[3.3.1]non-3-yl)-5-(trifluoromethoxy)-1H-indazole-3-carboxamide,
N-(9-Methyl-9-azabicyclo[3.3.1]non-3-yl)-6-(1,3-thiazol-2-yl)-1H-indazole-3-carboxamide hydroformate,
N-(9-Methyl-9-azabicyclo[3.3.1]non-3-yl)-6-(1,3-thiazol-2-yl)-1H-indazole-3-carboxamide,
N-(9-Methyl-9-azabicyclo[3.3.1]non-3-yl)-6-(2-thienyl)-1H-indazole-3-carboxamide hydroformate,
N-(9-Methyl-9-azabicyclo[3.3.1]non-3-yl)-6-(2-thienyl)-1H-indazole-3-carboxamide,
N-(9-Methyl-9-azabicyclo[3.3.1]non-3-yl)-6-(4-methyl-2-thienyl)-1H-indazole-3-carboxamide hydroformate,
N-(9-Methyl-9-azabicyclo[3.3.1]non-3-yl)-6-(4-methyl-2-thienyl)-1H-indazole-3-carboxamide,
N-(exo-8-Methyl-8-azabicyclo[3.2.1]oct-3-yl)-6-(trifluoromethoxy)-1H-indazole-3-carboxamide hydroformate,
N-(exo-8-Methyl-8-azabicyclo[3.2.1]oct-3-yl)-6-(trifluoromethoxy)-1H-indazole-3-carboxamide,
N-[(rel-6R,8aS)-Octahydroindolizin-6-yl]-1H-indazole-3-carboxamide hydroformate,
N-[(rel-6R,8aS)-Octahydroindolizin-6-yl]-1H-indazole-3-carboxamide,
N-[(rel-6S,8aS)-Octahydroindolizin-6-yl]-1H-indazole-3-carboxamide hydroformate,
N-[(rel-6S,8aS)-Octahydroindolizin-6-yl]-1H-indazole-3-carboxamide,
N-Methyl-N-(8-methyl-8-azabicyclo[3.2.1]oct-3-yl)-1H-indazole-3-carboxamide, N-Methyl-N-(8-methyl-8-azabicyclo[3.2.1]oct-3-yl)-1H-indazole-3-carboxamide hydroformate,
6-Methoxy-N-(endo-8-methyl-8-azabicyclo[3.2.1]oct-3-yl)-1,2-benzisothiazole-3-carboxamide hydrochloride,
6-Methoxy-N-(endo-8-methyl-8-azabicyclo[3.2.1]oct-3-yl)-1,2-benzisothiazole-3-carboxamide,
7-Methoxy-N-(endo-8-methyl-8-azabicyclo[3.2.1]oct-3-yl)-1,2-benzisothiazole-3-carboxamide hydroformate,
7-Methoxy-N-(endo-8-methyl-8-azabicyclo[3.2.1]oct-3-yl)-1,2-benzisothiazole-3-carboxamide,
6-Methoxy-N-(8-methyl-8-azabicyclo[3.2.1]oct-3-yl)-1H-indazole-3-carboxamide,
6-Methoxy-N-(exo-8-methyl-8-azabicyclo[3.2.1]oct-3-yl)-1H-indazole-3-carboxamide,
6-Methoxy-N-(9-methyl-9-azabicyclo[3.3.1]non-3-yl)-1H-indazole-3-carboxamide,
N-(8-Methyl-8-azabicyclo[3.2.1]oct-3-yl)-5-(2-trimethylsilylethyn-1-yl)-1H-indazole-3-carboxamide,
N-(9-Methyl-9-azabicyclo[3.3.1]non-3-yl)-5-(2-trimethylsilylethyn-1-yl)-1H-indazole-3-carboxamide,
5-Methoxy-N-methyl-N-(endo-8-methyl-8-azabicyclo[3.2.1]oct-3-yl)-1H-indazole-3-carboxamide hydroformate,
5-Methoxy-N-methyl-N-(endo-8-methyl-8-azabicyclo[3.2.1]oct-3-yl)-1H-indazole-3-carboxamide,
6-Methoxy-N-(endo-8-methyl-8-azabicyclo[3.2.1]oct-3-yl)-1H-indazole-3-carboxamide hydroformate,
N-(8-Methyl-8-azabicyclo[3.2.1]oct-3-yl)-6-(2-trimethylsilylethyn-1-yl)-1H-indazole-3-carboxamide hydroformate,
N-(8-Methyl-8-azabicyclo[3.2.1]oct-3-yl)-6-(2-trimethylsilylethyn-1-yl)-1H-indazole-3-carboxamide,
N-(8-Methyl-8-azabicyclo[3.2.1]oct-3-yl)-6-(1,3-thiazol-2-yl)-1H-indazole-3-carboxamide
N-(1H-Indazol-3-ylmethyl)-N,8-dimethyl-8-azabicyclo[3.2.1]octan-3-amine dihydroformate,
N-(1H-Indazol-3-ylmethyl)-N,8-dimethyl-8-azabicyclo[3.2.1]octan-3-amine,
5-Fluoro-N-(8-methyl-8-azabicyclo[3.2.1]oct-3-yl)-1H-indazole-3-carboxamide hydroformate,
5-Fluoro-N-(8-methyl-8-azabicyclo[3.2.1]oct-3-yl)-1H-indazole-3-carboxamide,
3-(Hexahydropyrrolo[1,2-a]pyrazin-2(1H)-ylcarbonyl)-6-methoxy-1H-indazole hydroformate,
3-(Hexahydropyrrolo[1,2-a]pyrazin-2(1H)-ylcarbonyl)-6-methoxy-1H-indazole,
2-(1H-Indazol-3-ylcarbonyl)octahydro-2H-pyrido[1,2-a]pyrazine hydroformate,
2-(1H-Indazol-3-ylcarbonyl)octahydro-2H-pyrido[1,2-a]pyrazine,
N-(8-Methyl-8-azabicyclo[3.2.1]oct-3-yl)-5-(phenylthio)-1H-indazole-3-carboxamide hydroformate,
N-(8-Methyl-8-azabicyclo[3.2.1]oct-3-yl)-5-(phenylthio)-1H-indazole-3-carboxamide,
N-(8-Methyl-8-azabicyclo[3.2.1]oct-3-yl)-6-(1,3-oxazol-2-yl)-1H-indazole-3-carboxamide hydroformate,
N-(8-Methyl-8-azabicyclo[3.2.1]oct-3-yl)-6-(1,3-oxazol-2-yl)-1H-indazole-3-carboxamide,
N-(exo-8-Methyl-8-azabicyclo[3.2.1]oct-3-yl)-6-(1,3-oxazol-2-yl)-1H-indazole-3-carboxamide hydroformate,
N-(exo-8-Methyl-8-azabicyclo[3.2.1]oct-3-yl)-6-(1,3-oxazol-2-yl)-1H-indazole-3-carboxamide,
N-(endo-8-Methyl-8-azabicyclo[3.2.1]oct-3-yl)-6-(1,3-oxazol-2-yl)-1H-indazole-3-carboxamide hydroformate,
N-(endo-8-Methyl-8-azabicyclo[3.2.1]oct-3-yl)-6-(1,3-oxazol-2-yl)-1H-indazole-3-carboxamide,
N-(8-Methyl-8-azabicyclo[3.2.1]oct-3-yl)-5-nitro-1H-indazole-3-carboxamide hydroformate,
N-(8-Methyl-8-azabicyclo[3.2.1]oct-3-yl)-5-nitro-1H-indazole-3-carboxamide,
N-(9-Methyl-9-azabicyclo[3.3.1]non-3-yl)-5-nitro-1H-indazole-3-carboxamide hydroformate,
N-(9-Methyl-9-azabicyclo[3.3.1]non-3-yl)-5-nitro-1H-indazole-3-carboxamide,
5-Methoxy-N-(exo-8-methyl-8-azabicyclo[3.2.1]oct-3-yl)-1H-indazole-3-carboxamide hydroformate,
5-Methoxy-N-(exo-8-methyl-8-azabicyclo[3.2.1]oct-3-yl)-1H-indazole-3-carboxamide,
5-(3,6-Dihydro-2H-pyran-4-yl)-N-(8-methyl-8-azabicyclo[3.2.1]oct-3-yl)-1H-indazole-3-carboxamide hydroformate,
5-(3,6-Dihydro-2H-pyran-4-yl)-N-(8-methyl-8-azabicyclo[3.2.1]oct-3-yl)-1H-indazole-3-carboxamide,
5-(3,6-Dihydro-2H-pyran-4-yl)-N-(9-methyl-9-azabicyclo[3.3.1]non-3-yl)-1H-indazole-3-carboxamide hydroformnate,
5-(3,6-Dihydro-2H-pyran-4-yl)-N-(9-methyl-9-azabicyclo[3.3.1]non-3-yl)-1H-indazole-3-carboxamide,
N-(9-Methyl-9-azabicyclo[3.3.1]non-3-yl)-5-(1,3-oxazol-2-yl)-1H-indazole-3-carboxamide hydroformate,
N-(9-Methyl-9-azabicyclo[3.3.1]non-3-yl)-5-(1,3-oxazol-2-yl)-1H-indazole-3-carboxamide,
and pharmaceutically acceptable salts thereof.

According to a further compound and/or method aspect of the invention, the compounds of Formulas I, II and III are selected from:
(8-Methyl-8-azabicyclo[3.2.1]non-3-yl)-6-(2-thienyl)-1H-indazole-3-carboxamide hydroformate,
(8-Methyl-8-azabicyclo[3.2.1]non-3-yl)-6-(2-thienyl)-1H-indazole-3-carboxamide,
3-(Hexahydropyrrolo[1,2-a]pyrazin-2(1H)-ylcarbonyl)-1H-indazole hydroformate,
3-(Hexahydropyrrolo[1,2-a]pyrazin-2(1H)-ylcarbonyl)-1H-indazole,
3-[(3-Methyl-3,8-diazabicyclo[3.2.1]oct-8-yl)carbonyl]-1H-indazole hydroformate,
3-[(3-Methyl-3,8-diazabicyclo[3.2.1]oct-8-yl)carbonyl]-1H-indazole,
3-[(8-Methyl-3,8-diazabicyclo[3.2.1]oct-3-yl)carbonyl]-1H-indazole hydroformate,
3-[(8-Methyl-3,8-diazabicyclo[3.2.1]oct-3-yl)carbonyl]-1H-indazole,
3-[(8-Methyl-3,8-diazabicyclo[3.2.1]oct-3-yl)carbonyl]-5-(trifluoromethoxy)-1H-indazole hydroformate,
3-[(8-Methyl-3,8-diazabicyclo[3.2.1]oct-3-yl)carbonyl]-5-(trifluoromethoxy)-1H-indazole,
5-(1-Benzyl-1H-pyrazol-4-yl)-N-(9-methyl-9-azabicyclo[3.3.1]non-3-yl)-1H-indazole-3-carboxamide hydroformate,
5-(1-Benzyl-1H-pyrazol-4-yl)-N-(9-methyl-9-azabicyclo[3.3.1]non-3-yl)-1H-indazole-3-carboxamide,
5-(2,3'-Bithien-5-yl)-N-(9-methyl-9-azabicyclo[3.3.1]non-3-yl)-1H-indazole-3-carboxamide hydroformate,
5-(2,3'-Bithien-5-yl)-N-(9-methyl-9-azabicyclo[3.3.1]non-3-yl)-1H-indazole-3-carboxamide,
5-(2-Furyl)-N-(8-methyl-8-azabicyclo[3.2.1]oct-3-yl)-1H-indazole-3-carboxamide,
5-(3,5-Dimethylisoxazol-4-yl)-N-(8-methyl-8-azabicyclo[3.2.1]oct-3-yl)-1H-indazole-3-carboxamide hydroformate,
5-(3,5-Dimethylisoxazol-4-yl)-N-(8-methyl-8-azabicyclo[3.2.1]oct-3-yl)-1H-indazole-3-carboxamide,
5-(3-Furyl)-N-(8-methyl-8-azabicyclo[3.2.1]oct-3-yl)-1H-indazole-3-carboxamide hydroformate, 5-(3-Furyl)-N-(8-methyl-8-azabicyclo[3.2.1]oct-3-yl)-1H-indazole-3-carboxamide,
5-(3-Furyl)-N-(9-methyl-9-azabicyclo[3.3.1]non-3-yl)-1H-indazole-3-carboxamide hydroformate,
5-(3-Furyl)-N-(9-methyl-9-azabicyclo[3.3.1]non-3-yl)-1H-indazole-3-carboxamide,
5-(4-Fluorophenyl)-N-(8-methyl-8-azabicyclo[3.2.1]oct-3-yl)-1H-indazole-3-carboxamide hydroformate,
5-(4-Fluorophenyl)-N-(8-methyl-8-azabicyclo[3.2.1]oct-3-yl)-1H-indazole-3-carboxamide,
5-Cyano-N-(8-methyl-8-azabicyclo[3.2.1]oct-3-yl)-1H-indazole-3-carboxamide hydroformate,
5-Cyano-N-(8-methyl-8-azabicyclo[3.2.1]oct-3-yl)-1H-indazole-3-carboxamide,
5-Ethynyl-N-(8-methyl-8-azabicyclo[3.2.1]oct-3-yl)-1H-indazole-3-carboxamide,
5-Methoxy-3-[(8-methyl-3,8-diazabicyclo[3.2.1]oct-3-yl)carbonyl]-1H-indazole hydroformate,
5-Methoxy-3-[(8-methyl-3,8-diazabicyclo[3.2.1]oct-3-yl)carbonyl]-1H-indazole,
5-Methoxy-N-(8-methyl-8-azabicyclo[3.2.1]oct-3-yl)-1H-indazole-3-carboxamide hydroformate,
5-Methoxy-N-(8-methyl-8-azabicyclo[3.2.1]oct-3-yl)-1H-indazole-3-carboxamide,
5-Methoxy-N-(9-methyl-9-azabicyclo[3.3.1]non-3-yl)-1H-indazole-3-carboxamide hydroformate,
5-Methoxy-N-(9-methyl-9-azabicyclo[3.3.1]non-3-yl)-1H-indazole-3-carboxamide,
5-Methoxy-N-methyl-N-(8-methyl-8-azabicyclo[3.2.1]oct-3-yl)-1H-indazole-3-carboxamide hydroformate,
5-Methoxy-N-methyl-N-(8-methyl-8-azabicyclo[3.2.1]oct-3-yl)-1H-indazole-3-carboxamide,
6-(2-Furyl)-N-(8-methyl-8-azabicyclo[3.2.1]oct-3-yl)-1H-indazole-3-carboxamide hydroformate,
6-(2-Furyl)-N-(8-methyl-8-azabicyclo[3.2.1]oct-3-yl)-1H-indazole-3-carboxamide,
6-(3-Furyl)-N-(8-methyl-8-azabicyclo[3.2.1]oct-3-yl)-1H-indazole-3-carboxamide,
6-(4-Fluorophenyl)-N-(8-methyl-8-azabicyclo[3.2.1]oct-3-yl)-1H-indazole-3-carboxamide hydroformate,
6-(4-Fluorophenyl)-N-(8-methyl-8-azabicyclo[3.2.1]oct-3-yl)-1H-indazole-3-carboxamide,
6-Cyano-N-(8-methyl-8-azabicyclo[3.2.1]oct-3-yl)-1H-indazole-3-carboxamide hydroformate,
6-Cyano-N-(8-methyl-8-azabicyclo[3.2.1]oct-3-yl)-1H-indazole-3-carboxamide,
6-Cyclopropyl-N-(8-methyl-8-azabicyclo[3.2.1]oct-3-yl)-1,2-benzisothiazole-3-carboxamide hydroformate,
6-Cyclopropyl-N-(8-methyl-8-azabicyclo[3.2.1]oct-3-yl)-1,2-benzisothiazole-3-carboxamide,
6-Ethoxy-N-(8-methyl-8-azabicyclo[3.2.1]oct-3-yl)-1,2-benzisothiazole-3-carboxamide hydroformate,
6-Ethoxy-N-(8-methyl-8-azabicyclo[3.2.1]oct-3-yl)-1,2-benzisothiazole-3-carboxamide,
6-Methoxy-3-[(8-methyl-3,8-diazabicyclo[3.2.1]oct-3-yl)carbonyl]-1,2-benzisothiazole hydroformate,
6-Methoxy-3-[(8-methyl-3,8-diazabicyclo[3.2.1]oct-3-yl)carbonyl]-1,2-benzisothiazole,
6-Methoxy-3-[(8-methyl-3,8-diazabicyclo[3.2.1]oct-3-yl)carbonyl]-1H-indazole hydroformate,
6-Methoxy-3-[(8-methyl-3,8-diazabicyclo[3.2.1]oct-3-yl)carbonyl]-1H-indazole,
6-Methoxy-N-(2-methyl-2-azabicyclo[2.2.2]oct-5-yl)-1,2-benzisothiazole-3-carboxamide,
6-Methoxy-N-(8-methyl-8-azabicyclo[3.2.1]oct-3-yl)-1,2-benzisothiazole-3-carboxamide hydrochloride,
6-Methoxy-N-(8-methyl-8-azabicyclo[3.2.1]oct-3-yl)-1,2-benzisothiazole-3-carboxamide,
6-Methoxy-N-(9-methyl-9-azabicyclo[3.3.1]non-3-yl)-1,2-benzisothiazole-3-carboxamide,
6-Methoxy-N-(9-methyl-9-azabicyclo[3.3.1]non-3-yl)-1H-indazole-3-carboxamide,
6-Methoxy-N-(endo-8-methyl-8-azabicyclo[3.2.1]oct-3-yl)-1H-indazole-3-carboxamide,
7-Methoxy-N-(8-methyl-8-azabicyclo[3.2.1]oct-3-yl)-1,2-benzisothiazole-3-carboxamide hydroformate,
7-Methoxy-N-(8-methyl-8-azabicyclo[3.2.1]oct-3-yl)-1,2-benzisothiazole-3-carboxamide,
7-Methoxy-N-(9-methyl-9-azabicyclo[3.3.1]non-3-yl)-1H-indazole-3-carboxamide hydroformate,
7-Methoxy-N-(9-methyl-9-azabicyclo[3.3.1]non-3-yl)-1H-indazole-3-carboxamide,
8-Methyl-N-{[5-(3-thienyl)-1H-indazol-3-yl]methyl}-8-azabicyclo[3.2.1]octan-3-amine hydroformate,
8-Methyl-N-{[5-(3-thienyl)-1H-indazol-3-yl]methyl}-8-azabicyclo[3.2.1]octan-3-amine,
N-(2-Cyclopropylmethyl-2-azabicyclo[2.2.1]hept-5-yl)-1H-indazole-3-carboxamide hydroformate,
N-(2-Cyclopropylmethyl-2-azabicyclo[2.2.1]hept-5-yl)-1H-indazole-3-carboxamide,
N-(2-Ethyl-2-azabicyclo[2.2.1]hept-5-yl)-1H-indazole-3-carboxamide hydroformate,
N-(2-Ethyl-2-azabicyclo[2.2.1]hept-5-yl)-1H-indazole-3-carboxamide,
N-(2-Methyl-2-azabicyclo[2.2.1]hept-5-yl)-1H-indazole-3-carboxamide hydroformate,
N-(2-Methyl-2-azabicyclo[2.2.1]hept-5-yl)-1H-indazole-3-carboxamide,
N-(8-Methyl-8-azabicyclo[3.2.1]oct-3-yl)-1,2-benzisothiazole-3-carboxamide,
N-(8-Methyl-8-azabicyclo[3.2.1]oct-3-yl)-5-(1,3-thiazol-2-yl)-1H-indazole-3-carboxamide hydroformate,
N-(8-Methyl-8-azabicyclo[3.2.1]oct-3-yl)-5-(1,3-thiazol-2-yl)-1H-indazole-3-carboxamide,
N-(8-Methyl-8-azabicyclo[3.2.1]oct-3-yl)-5-(1-methyl-1H-imidazol-2-yl)-1H-indazole-3-carboxamide hydroformate,
N-(8-Methyl-8-azabicyclo[3.2.1]oct-3-yl)-5-(1-methyl-1H-imidazol-2-yl)-1H-indazole-3-carboxamide,
N-(8-Methyl-8-azabicyclo[3.2.1]oct-3-yl)-5-(2-thienyl)-1H-indazole-3-carboxamide,
N-(8-Methyl-8-azabicyclo[3.2.1]oct-3-yl)-5-(2-trimethylsilylethynyl)-1H-indazole-3-carboxamide,
N-(8-Methyl-8-azabicyclo[3.2.1]oct-3-yl)-5-(3-thienyl)-1H-indazole-3-carbothioamide hydroformate,
N-(8-Methyl-8-azabicyclo[3.2.1]oct-3-yl)-5-(3-thienyl)-1H-indazole-3-carbothioamide,
N-(8-Methyl-8-azabicyclo[3.2.1]oct-3-yl)-5-(3-thienyl)-1H-indazole-3-carboxamide hydroformate,
N-(8-Methyl-8-azabicyclo[3.2.1]oct-3-yl)-5-(3-thienyl)-1H-indazole-3-carboxamide,
N-(8-Methyl-8-azabicyclo[3.2.1]oct-3-yl)-5-(5-methyl-2-thienyl)-1H-indazole-3-carboxamide hydroformate,
N-(8-Methyl-8-azabicyclo[3.2.1]oct-3-yl)-5-(5-methyl-2-thienyl)-1H-indazole-3-carboxamide,
N-(8-Methyl-8-azabicyclo[3.2.1]oct-3-yl)-5-(morpholin-4-yl)-1H-indazole-3-carboxamide hydroformate,
N-(8-Methyl-8-azabicyclo[3.2.1]oct-3-yl)-5-(morpholin-4-yl)-1H-indazole-3-carboxamide,
N-(8-Methyl-8-azabicyclo[3.2.1]oct-3-yl)-5-(pyrrolidin-1-yl)-1H-indazole-3-carboxamide hydroformate,
N-(8-Methyl-8-azabicyclo[3.2.1]oct-3-yl)-5-(pyrrolidin-1-yl)-1H-indazole-3-carboxamide, N-(8-Methyl-8-azabicyclo[3.2.1]oct-3-yl)-5-(thiomorpholin-4-yl)-1H-indazole-3-carboxamide hydroformate,
N-(8-Methyl-8-azabicyclo[3.2.1]oct-3-yl)-5-(thiomorpholin-4-yl)-1H-indazole-3-carboxamide,
N-(8-Methyl-8-azabicyclo[3.2.1]oct-3-yl)-5-(trifluoromethoxy)-1H-indazole-3-carboxamide hydroformate,
N-(8-Methyl-8-azabicyclo[3.2.1]oct-3-yl)-5-(trifluoromethoxy)-1H-indazole-3-carboxamide,
N-(8-Methyl-8-azabicyclo[3.2.1]oct-3-yl)-5-[(3-trifluoromethyl)phenyl]-1H-indazole-3-carboxamide hydroformate,
N-(8-Methyl-8-azabicyclo[3.2.1]oct-3-yl)-5-[(3-trifluoromethyl)phenyl]-1H-indazole-3-carboxamide,
N-(8-Methyl-8-azabicyclo[3.2.1]oct-3-yl)-5-[(4-trifluoromethyl)phenyl]-1H-indazole-3-carboxamide hydroformate,
N-(8-Methyl-8-azabicyclo[3.2.1]oct-3-yl)-5-[(4-trifluoromethyl)phenyl]-1H-indazole-3-carboxamide,
N-(8-Methyl-8-azabicyclo[3.2.1]oct-3-yl)-5-{5-[3-(trifluoromethyl)phenyl]-2-thienyl}-1H-indazole-3-carboxamide hydroformate,
N-(8-Methyl-8-azabicyclo[3.2.1]oct-3-yl)-5-{5-[3-(trifluoromethyl)phenyl]-2-thienyl}-1H-indazole-3-carboxamide,
N-(8-Methyl-8-azabicyclo[3.2.1]oct-3-yl)-6-(1,3-thiazol-2-yl)-1H-indazole-3-carboxamide hydroformate,
N-(8-Methyl-8-azabicyclo[3.2.1]oct-3-yl)-6-(1,3-thiazol-2-yl)-1H-indazole-3-carboxamide,
N-(8-Methyl-8-azabicyclo[3.2.1]oct-3-yl)-6-(1-methyl-1H-imidazol-2-yl)-1H-indazole-3-carboxamide dihydrochloride,
N-(8-Methyl-8-azabicyclo[3.2.1]oct-3-yl)-6-(1-methyl-1H-imidazol-2-yl)-1H-indazole-3-carboxamide,
N-(8-Methyl-8-azabicyclo[3.2.1]oct-3-yl)-6-(2-trimethylsilylethynyl)-1H-indazole-3-carboxamide hydroformate,
N-(8-Methyl-8-azabicyclo[3.2.1]oct-3-yl)-6-(2-trimethylsilylethynyl)-1H-indazole-3-carboxamide,
N-(8-Methyl-8-azabicyclo[3.2.1]oct-3-yl)-6-(3-thienyl)-1H-indazole-3-carboxamide,
N-(8-Methyl-8-azabicyclo[3.2.1]oct-3-yl)-6-(5-methyl-2-thienyl)-1H-indazole-3-carboxamide hydroformate,
N-(8-Methyl-8-azabicyclo[3.2.1]oct-3-yl)-6-(5-methyl-2-thienyl)-1H-indazole-3-carboxamide,
N-(8-Methyl-8-azabicyclo[3.2.1]oct-3-yl)-6-(trifluoromethoxy)-1H-indazole-3-carboxamide hydroformate,
N-(8-Methyl-8-azabicyclo[3.2.1]oct-3-yl)-6-(trifluoromethoxy)-1H-indazole-3-carboxamide,
N-(8-Methyl-8-azabicyclo[3.2.1]oct-3-yl)-6-[(3-trifluoromethyl)phenyl]-1H-indazole-3-carboxamide hydroformate,
N-(8-Methyl-8-azabicyclo[3.2.1]oct-3-yl)-6-[(3-trifluoromethyl)phenyl]-1H-indazole-3-carboxamide,
N-(8-Methyl-8-azabicyclo[3.2.1]oct-3-yl)-6-[(4-trifluoromethyl)phenyl]-1H-indazole-3-carboxamide hydroformate,
N-(8-Methyl-8-azabicyclo[3.2.1]oct-3-yl)-6-[(4-trifluoromethyl)phenyl]-1H-indazole-3-carboxamide,
N-(8-Methyl-8-azabicyclo[3.2.1]oct-3-yl)-7-(trifluoromethoxy)-1H-indazole-3-carboxamide hydroformate,
N-(8-Methyl-8-azabicyclo[3.2.1]oct-3-yl)-7-(trifluoromethoxy)-1H-indazole-3-carboxamide,
N-(9-Methyl-9-azabicyclo[3.3.1]non-3-yl)-5-(1,3-thiazol-2-yl)-1H-indazole-3-carboxamide hydroformate,
N-(9-Methyl-9-azabicyclo[3.3.1]non-3-yl)-5-(1,3-thiazol-2-yl)-1H-indazole-3-carboxamide,
N-(9-Methyl-9-azabicyclo[3.3.1]non-3-yl)-5-(1-methyl-1H-imidazol-2-yl)-1H-indazole-3-carboxamide dihydroformate,
N-(9-Methyl-9-azabicyclo[3.3.1]non-3-yl)-5-(1-methyl-1H-imidazol-2-yl)-1H-indazole-3-carboxamide,
N-(9-Methyl-9-azabicyclo[3.3.1]non-3-yl)-5-(2-trimethylsilylethynyl)-1H-indazole-3-carboxamide
N-(9-Methyl-9-azabicyclo[3.3.1]non-3-yl)-5-(3-thienyl)-1H-indazole-3-carboxamide hydroformate,
N-(9-Methyl-9-azabicyclo[3.3.1]non-3-yl)-5-(3-thienyl)-1H-indazole-3-carboxamide,
N-(9-Methyl-9-azabicyclo[3.3.1]non-3-yl)-5-(4-methyl-2-thienyl)-1H-indazole-3-carboxamide hydroformate,
N-(9-Methyl-9-azabicyclo[3.3.1]non-3-yl)-5-(4-methyl-2-thienyl)-1H-indazole-3-carboxamide,
N-(9-Methyl-9-azabicyclo[3.3.1]non-3-yl)-5-(morpholin-4-yl)-1H-indazole-3-carboxamide hydroformate,
N-(9-Methyl-9-azabicyclo[3.3.1]non-3-yl)-5-(morpholin-4-yl)-1H-indazole-3-carboxamide,
N-(9-Methyl-9-azabicyclo[3.3.1]non-3-yl)-5-(pyrrolidin-1-yl)-1H-indazole-3-carboxamide hydroformate,
N-(9-Methyl-9-azabicyclo[3.3.1]non-3-yl)-5-(pyrrolidin-1-yl)-1H-indazole-3-carboxamide,
N-(9-Methyl-9-azabicyclo[3.3.1]non-3-yl)-5-(thiomorpholin-4-yl)-1H-indazole-3-carboxamide hydroformate,
N-(9-Methyl-9-azabicyclo[3.3.1]non-3-yl)-5-(thiomorpholin-4-yl)-1H-indazole-3-carboxamide,
N-(9-Methyl-9-azabicyclo[3.3.1]non-3-yl)-5-(trifluoromethoxy)-1H-indazole-3-carboxamide hydroformate,
N-(9-Methyl-9-azabicyclo[3.3.1]non-3-yl)-5-(trifluoromethoxy)-1H-indazole-3-carboxamide,
N-(9-Methyl-9-azabicyclo[3.3.1]non-3-yl)-6-(1,3-thiazol-2-yl)-1H-indazole-3-carboxamide hydroformate,
N-(9-Methyl-9-azabicyclo[3.3.1]non-3-yl)-6-(1,3-thiazol-2-yl)-1H-indazole-3-carboxamide,
N-(9-Methyl-9-azabicyclo[3.3.1]non-3-yl)-6-(2-thienyl)-1H-indazole-3-carboxamide hydroformate,
N-(9-Methyl-9-azabicyclo[3.3.1]non-3-yl)-6-(2-thienyl)-1H-indazole-3-carboxamide,
N-(9-Methyl-9-azabicyclo[3.3.1]non-3-yl)-6-(4-methyl-2-thienyl)-1H-indazole-3-carboxamide hydroformate,
N-(9-Methyl-9-azabicyclo[3.3.1]non-3-yl)-6-(4-methyl-2-thienyl)-1H-indazole-3-carboxamide,
N-(exo-8-Methyl-8-azabicyclo[3.2.1]oct-3-yl)-6-(trifluoromethoxy)-1H-indazole-3-carboxamide hydroformate,
N-(exo-8-Methyl-8-azabicyclo[3.2.1]oct-3-yl)-6-(trifluoromethoxy)-1H-indazole-3-carboxamide,
N-[(rel-6R,8aS)-Octahydroindolizin-6-yl]-1H-indazole-3-carboxamide hydroformate,
N-[(rel-6R,8aS)-Octahydroindolizin-6-yl]-1H-indazole-3-carboxamide,
N-[(rel-6S,8aS)-Octahydroindolizin-6-yl]-1H-indazole-3-carboxamide hydroformate,
N-[(rel-6S,8aS)-Octahydroindolizin-6-yl]-1H-indazole-3-carboxamide,
6-Methoxy-N-(endo-8-methyl-8-azabicyclo[3.2.1]oct-3-yl)-1,2-benzisothiazole-3-carboxamide hydrochloride,
6-Methoxy-N-(endo-8-methyl-8-azabicyclo[3.2.1]oct-3-yl)-1,2-benzisothiazole-3-carboxamide,
7-Methoxy-N-(endo-8-methyl-8-azabicyclo[3.2.1]oct-3-yl)-1,2-benzisothiazole-3-carboxamide hydroformate,
7-Methoxy-N-(endo-8-methyl-8-azabicyclo[3.2.1]oct-3-yl)-1,2-benzisothiazole-3-carboxamide,
6-Methoxy-N-(8-methyl-8-azabicyclo[3.2.1]oct-3-yl)-1H-indazole-3-carboxamide
6-Methoxy-N-(exo-8-methyl-8-azabicyclo[3.2.1]oct-3-yl)-1H-indazole-3-carboxamide
6-Methoxy-N-(9-methyl-9-azabicyclo[3.3.1]non-3-yl)-1H-indazole-3-carboxamide
N-(8-Methyl-8-azabicyclo[3.2.1]oct-3-yl)-5-(2-trimethylsilylethyn-1-yl)-1H-indazole-3-carboxamide, N-(9-Methyl-9-azabicyclo[3.3.1]non-3-yl)-5-(2-trimethylsilylethyn-1-yl)-1H-indazole-3-carboxamide,
5-Methoxy-N-methyl-N-(endo-8-methyl-8-azabicyclo[3.2.1]oct-3-yl)-1H-indazole-3-carboxamide hydroformate,
5-Methoxy-N-methyl-N-(endo-8-methyl-8-azabicyclo[3.2.1]oct-3-yl)-1H-indazole-3-carboxamide,
6-Methoxy-N-(endo-8-methyl-8-azabicyclo[3.2.1]oct-3-yl)-1H-indazole-3-carboxamide hydroformate,
N-(8-Methyl-8-azabicyclo[3.2.1]oct-3-yl)-6-(2-trimethylsilylethyn-1-yl)-1H-indazole-3-carboxamide hydroformate,
N-(8-Methyl-8-azabicyclo[3.2.1]oct-3-yl)-6-(2-trimethylsilylethyn-1-yl)-1H-indazole-3-carboxamide,
N-(8-Methyl-8-azabicyclo[3.2.1]oct-3-yl)-6-(1,3-thiazol-2-yl)-1H-indazole-3-carboxamide
N-(1H-Indazol-3-ylmethyl)-N,8-dimethyl-8-azabicyclo[3.2.1]octan-3-amine dihydroformate,
N-(1H-Indazol-3-ylmethyl)-N,8-dimethyl-8-azabicyclo[3.2.1]octan-3-amine,
5-Fluoro-N-(8-methyl-8-azabicyclo[3.2.1]oct-3-yl)-1H-indazole-3-carboxamide hydroformate,
5-Fluoro-N-(8-methyl-8-azabicyclo[3.2.1]oct-3-yl)-1H-indazole-3-carboxamide,
3-(Hexahydropyrrolo[1,2-a]pyrazin-2(1H)-ylcarbonyl)-6-methoxy-1H-indazole hydroformate,
3-(Hexahydropyrrolo[1,2-a]pyrazin-2(1H)-ylcarbonyl)-6-methoxy-1H-indazole,
2-(1H-Indazol-3-ylcarbonyl)octahydro-2H-pyrido[1,2-a]pyrazine hydroformate,
2-(1H-Indazol-3-ylcarbonyl)octahydro-2H-pyrido[1,2-a]pyrazine,
N-(8-Methyl-8-azabicyclo[3.2.1]oct-3-yl)-5-(phenylthio)-1H-indazole-3-carboxamide hydroformate,
N-(8-Methyl-8-azabicyclo[3.2.1]oct-3-yl)-5-(phenylthio)-1H-indazole-3-carboxamide,
N-(8-Methyl-8-azabicyclo[3.2.1]oct-3-yl)-6-(1,3-oxazol-2-yl)-1H-indazole-3-carboxamide hydroformate,
N-(8-Methyl-8-azabicyclo[3.2.1]oct-3-yl)-6-(1,3-oxazol-2-yl)-1H-indazole-3-carboxamide,
N-(exo-8-Methyl-8-azabicyclo[3.2.1]oct-3-yl)-6-(1,3-oxazol-2-yl)-1H-indazole-3-carboxamide hydroformate,
N-(exo-8-Methyl-8-azabicyclo[3.2.1]oct-3-yl)-6-(1,3-oxazol-2-yl)-1H-indazole-3-carboxamide,
N-(endo-8-Methyl-8-azabicyclo[3.2.1]oct-3-yl)-6-(1,3-oxazol-2-yl)-1H-indazole-3-carboxamide hydroformate,
N-(endo-8-Methyl-8-azabicyclo[3.2.1]oct-3-yl)-6-(1,3-oxazol-2-yl)-1H-indazole-3-carboxamide,
N-(8-Methyl-8-azabicyclo[3.2.1]oct-3-yl)-5-nitro-1H-indazole-3-carboxamide hydroformate,
N-(8-Methyl-8-azabicyclo[3.2.1]oct-3-yl)-5-nitro-1H-indazole-3-carboxamide,
N-(9-Methyl-9-azabicyclo[3.3.1]non-3-yl)-5-nitro-1H-indazole-3-carboxamide hydroformate,
N-(9-Methyl-9-azabicyclo[3.3.1]non-3-yl)-5-nitro-1H-indazole-3-carboxamide,
5-Methoxy-N-(exo-8-methyl-8-azabicyclo[3.2.1]oct-3-yl)-1H-indazole-3-carboxamide hydroformate,
5-Methoxy-N-(exo-8-methyl-8-azabicyclo[3.2.1]oct-3-yl)-1H-indazole-3-carboxamide,
5-(3,6-Dihydro-2H-pyran-4-yl)-N-(8-methyl-8-azabicyclo[3.2.1]oct-3-yl)-1H-indazole-3-carboxamide hydroformate,
5-(3,6-Dihydro-2H-pyran-4-yl)-N-(8-methyl-8-azabicyclo[3.2.1]oct-3-yl)-1H-indazole-3-carboxamide,
5-(3,6-Dihydro-2H-pyran-4-yl)-N-(9-methyl-9-azabicyclo[3.3.1]non-3-yl)-1H-indazole-3-carboxamide hydroformate,
5-(3,6-Dihydro-2H-pyran-4-yl)-N-(9-methyl-9-azabicyclo[3.3.1]non-3-yl)-1H-indazole-3-carboxamide,
N-(9-Methyl-9-azabicyclo[3.3.1]non-3-yl)-5-(1,3-oxazol-2-yl)-1H-indazole-3-carboxamide hydroformate,
N-(9-Methyl-9-azabicyclo[3.3.1]non-3-yl)-5-(1,3-oxazol-2-yl)-1H-indazole-3-carboxamide,
and pharmaceutically acceptable salts thereof.

According to a further compound and/or method aspect of the invention, the compounds are selected from:

5-{[(Cyclopentylamino)carbonyl]amino}-N-(endo-8-methyl-8-azabicyclo[3.2.1]oct-3-yl)-1H-indazole-3-carboxamide hydroformate,
5-{[(Cyclopentylamino)carbonyl]amino}-N-(endo-8-methyl-8-azabicyclo[3.2.1]oct-3-yl)-1H-indazole-3-carboxamide,
5-Amino-N-(8-methyl-8-azabicyclo[3.2.1]oct-3-yl)-1H-indazole-3-carboxamide hydroformate,
5-Amino-N-(8-methyl-8-azabicyclo[3.2.1]oct-3-yl)-1H-indazole-3-carboxamide,
5-Amino-N-(9-methyl-9-azabicyclo[3.3.1]non-3-yl)-1H-indazole-3-carboxamide hydroformate,
5-Amino-N-(9-methyl-9-azabicyclo[3.3.1]non-3-yl)-1H-indazole-3-carboxamide,
6-(1-Benzyl-1H-1,2,3-triazol-4-yl)-N-(endo-8-methyl-8-azabicyclo[3.2.1]oct-3-yl)-1H-indazole-3-carboxamide dihydroformate,
6-(1-Benzyl-1H-1,2,3-triazol-4-yl)-N-(endo-8-methyl-8-azabicyclo[3.2.1]oct-3-yl)-1H-indazole-3-carboxamide,
6-(3,6-Dihydro-2H-pyran-4-yl)-N-(8-methyl-8-azabicyclo[3.2.1]oct-3-yl)-1H-indazole-3-carboxamide hydroformate,
6-(3,6-Dihydro-2H-pyran-4-yl)-N-(8-methyl-8-azabicyclo[3.2.1]oct-3-yl)-1H-indazole-3-carboxamide,
6-Methoxy-N-(8-methyl-8-azabicyclo[3.2.1]oct-3-yl)-1H-indazole-3-carboxamide hydroformate,
6-Methoxy-N-(8-methyl-8-azabicyclo[3.2.1]oct-3-yl)-1H-indazole-3-carboxamide,
6-Methoxy-N-(9-methyl-9-azabicyclo[3.3.1]non-3-yl)-1H-indazole-3-carboxamide hydroformate,
6-Methoxy-N-(exo-8-methyl-8-azabicyclo[3.2.1]oct-3-yl)-1H-indazole-3-carboxamide hydroformate,
Ethyl [4-(3-{[(8-methyl-8-azabicyclo[3.2.1]oct-3-yl)amino]carbonyl}-1H-indazol-6-yl)-1H-1,2,3-triazol-1-yl]acetate dihydroformate,
Ethyl [4-(3-{[(8-methyl-8-azabicyclo[3.2.1]oct-3-yl)amino]carbonyl}-1H-indazol-6-yl)-1H-1,2,3-triazol-1-yl]acetate,
N-(8-Methyl-8-azabicyclo[3.2.1]oct-3-yl)-1,2-benzisoxazole-3-carboxamide hydroformate,
N-(8-Methyl-8-azabicyclo[3.2.1]oct-3-yl)-1,2-benzisoxazole-3-carboxamide,
N-(8-Methyl-8-azabicyclo[3.2.1]oct-3-yl)-5-(phenylsulfonyl)-1H-indazole-3-carboxamide hydroformate,
N-(8-Methyl-8-azabicyclo[3.2.1]oct-3-yl)-5-(phenylsulfonyl)-1H-indazole-3-carboxamide,
N-(8-Methyl-8-azabicyclo[3.2.1]oct-3-yl)-6-(4-methyl-1,3-thiazol-2-yl)-1H-indazole-3-carboxamide hydroformate,
N-(8-Methyl-8-azabicyclo[3.2.1]oct-3-yl)-6-(4-methyl-1,3-thiazol-2-yl)-1H-indazole-3-carboxamide,
N-(8-Methyl-8-azabicyclo[3.2.1]oct-3-yl)-6-(5-methyl-1,3-thiazol-2-yl)-1H-indazole-3-carboxamide hydroformate,
N-(8-Methyl-8-azabicyclo[3.2.1]oct-3-yl)-6-(5-methyl-1,3-thiazol-2-yl)-1H-indazole-3-carboxamide,
N-(8-Methyl-8-azabicyclo[3.2.1]oct-3-yl)-6-(nitro)-1H-indazole-3-carboxamide hydroformate,
N-(8-Methyl-8-azabicyclo[3.2.1]oct-3-yl)-6-(nitro)-1H-indazole-3-carboxamide, N-(endo-8-Methyl-8-azabicyclo[3.2.1]oct-3-yl)-5-(1,3-thiazol-2-yl)-1H-indazole-3-carboxamide hydroformate,
N-(endo-8-Methyl-8-azabicyclo[3.2.1]oct-3-yl)-5-(1,3-thiazol-2-yl)-1H-indazole-3-carboxamide,
N-(endo-8-Methyl-8-azabicyclo[3.2.1]oct-3-yl)-5-(nitro)-1H-indazole-3-carboxamide hydroformate,
N-(endo-8-Methyl-8-azabicyclo[3.2.1]oct-3-yl)-5-(nitro)-1H-indazole-3-carboxamide,
N-(endo-8-Methyl-8-azabicyclo[3.2.1]oct-3-yl)-5-(trifluoromethoxy)-1H-indazole-3-carboxamide hydroformate,
N-(endo-8-Methyl-8-azabicyclo[3.2.1]oct-3-yl)-5-(trifluoromethoxy)-1H-indazole-3-carboxamide,
N-(endo-8-Methyl-8-azabicyclo[3.2.1]oct-3-yl)-5-{[(propylamino)carbonyl]amino}-1H-indazole-3-carboxamide hydroformate,
N-(endo-8-Methyl-8-azabicyclo[3.2.1]oct-3-yl)-5-{[(propylamino)carbonyl]amino}-1H-indazole-3-carboxamide,
N-(endo-8-Methyl-8-azabicyclo[3.2.1]oct-3-yl)-6-(4-methyl-1,3-thiazol-2-yl)-1H-indazole-3-carboxamide hydroformate,
N-(endo-8-Methyl-8-azabicyclo[3.2.1]oct-3-yl)-6-(4-methyl-1,3-thiazol-2-yl)-1H-indazole-3-carboxamide,
N-(endo-8-Methyl-8-azabicyclo[3.2.1]oct-3-yl)-6-(5-methyl-1,3-thiazol-2-yl)-1H-indazole-3-carboxamide hydroformate,
N-(endo-8-Methyl-8-azabicyclo[3.2.1]oct-3-yl)-6-(5-methyl-1,3-thiazol-2-yl)-1H-indazole-3-carboxamide,
N-(endo-8-Methyl-8-azabicyclo[3.2.1]oct-3-yl)-6-(nitro)-1H-indazole-3-carboxamide hydroformate,
N-(endo-8-Methyl-8-azabicyclo[3.2.1]oct-3-yl)-6-(nitro)-1H-indazole-3-carboxamide,
N-(endo-8-Methyl-8-azabicyclo[3.2.1]oct-3-yl)-6-(trifluoromethoxy)-1H-indazole-3-carboxamide hydroformate,
N-(endo-8-Methyl-8-azabicyclo[3.2.1]oct-3-yl)-6-(trifluoromethoxy)-1H-indazole-3-carboxamide,
N-(endo-8-Methyl-8-azabicyclo[3.2.1]oct-3-yl)-6-[1-(2-piperidin-1-ylethyl)-1H-1,2,3-triazol-4-yl]-1H-indazole-3-carboxamide trihydroformate,
N-(endo-8-Methyl-8-azabicyclo[3.2.1]oct-3-yl)-6-[1-(2-piperidin-1-ylethyl)-1H-1,2,3-triazol-4-yl]-1H-indazole-3-carboxamide,
N-(exo-8-Methyl-8-azabicyclo[3.2.1]oct-3-yl)-5-(1,3-thiazol-2-yl)-1H-indazole-3-carboxamide hydroformate,
N-(exo-8-Methyl-8-azabicyclo[3.2.1]oct-3-yl)-5-(1,3-thiazol-2-yl)-1H-indazole-3-carboxamide,
N-(exo-8-Methyl-8-azabicyclo[3.2.1]oct-3-yl)-5-(nitro)-1H-indazole-3-carboxamide hydroformate,
N-(exo-8-Methyl-8-azabicyclo[3.2.1]oct-3-yl)-5-(nitro)-1H-indazole-3-carboxamide,
N-(exo-8-Methyl-8-azabicyclo[3.2.1]oct-3-yl)-5-(trifluoromethoxy)-1H-indazole-3-carboxamide hydroformate,
N-(exo-8-Methyl-8-azabicyclo[3.2.1]oct-3-yl)-5-(trifluoromethoxy)-1H-indazole-3-carboxamide,
N-(exo-8-Methyl-8-azabicyclo[3.2.1]oct-3-yl)-6-(4-methyl-1,3-thiazol-2-yl)-1H-indazole-3-carboxamide hydroformate,
N-(exo-8-Methyl-8-azabicyclo[3.2.1]oct-3-yl)-6-(4-methyl-1,3-thiazol-2-yl)-1H-indazole-3-carboxamide,
N-(exo-8-Methyl-8-azabicyclo[3.2.1]oct-3-yl)-6-(5-methyl-1,3-thiazol-2-yl)-1H-indazole-3-carboxamide hydroformate,
N-(exo-8-Methyl-8-azabicyclo[3.2.1]oct-3-yl)-6-(5-methyl-1,3-thiazol-2-yl)-1H-indazole-3-carboxamide,
N-(exo-8-Methyl-8-azabicyclo[3.2.1]oct-3-yl)-6-(nitro)-1H-indazole-3-carboxamide hydroformate,
N-(exo-8-Methyl-8-azabicyclo[3.2.1]oct-3-yl)-6-(nitro)-1H-indazole-3-carboxamide,
and pharmaceutically acceptable salts thereof.

According to a further compound and/or method aspect of the invention, the compounds of Formulas I, II and III are selected from:

5-{[(Cyclopentylamino)carbonyl]amino}-N-(endo-8-methyl-8-azabicyclo[3.2.1]oct-3-yl)-1H-indazole-3-carboxamide hydroformate,
5-{[(Cyclopentylamino)carbonyl]amino}-N-(endo-8-methyl-8-azabicyclo[3.2.1]oct-3-yl)-1H-indazole-3-carboxamide,
5-Amino-N-(8-methyl-8-azabicyclo[3.2.1]oct-3-yl)-1H-indazole-3-carboxamide hydroformate,
5-Amino-N-(8-methyl-8-azabicyclo[3.2.1]oct-3-yl)-1H-indazole-3-carboxamide,
5-Amino-N-(9-methyl-9-azabicyclo[3.3.1]non-3-yl)-1H-indazole-3-carboxamide hydroformate,
5-Amino-N-(9-methyl-9-azabicyclo[3.3.1]non-3-yl)-1H-indazole-3-carboxamide,
6-(1-Benzyl-1H-1,2,3-triazol-4-yl)-N-(endo-8-methyl-8-azabicyclo[3.2.1]oct-3-yl)-1H-indazole-3-carboxamide dihydroformate,
6-(1-Benzyl-1H-1,2,3-triazol-4-yl)-N-(endo-8-methyl-8-azabicyclo[3.2.1]oct-3-yl)-1H-indazole-3-carboxamide,
6-(3,6-Dihydro-2H-pyran-4-yl)-N-(8-methyl-8-azabicyclo[3.2.1]oct-3-yl)-1H-indazole-3-carboxamide hydroformate,
6-(3,6-Dihydro-2H-pyran-4-yl)-N-(8-methyl-8-azabicyclo[3.2.1]oct-3-yl)-1H-indazole-3-carboxamide,
6-Methoxy-N-(8-methyl-8-azabicyclo[3.2.1]oct-3-yl)-1H-indazole-3-carboxamide hydroformate,
6-Methoxy-N-(8-methyl-8-azabicyclo[3.2.1]oct-3-yl)-1H-indazole-3-carboxamide,
6-Methoxy-N-(9-methyl-9-azabicyclo[3.3.1]non-3-yl)-1H-indazole-3-carboxamide hydroformate,
6-Methoxy-N-(exo-8-methyl-8-azabicyclo[3.2.1]oct-3-yl)-1H-indazole-3-carboxamide hydroformate,
Ethyl [4-(3-{[(8-methyl-8-azabicyclo[3.2.1]oct-3-yl)amino]carbonyl}-1H-1H-1,2,3-triazol-1-yl]acetate dihydroformate,
Ethyl [4-(3-{[(8-methyl-8-azabicyclo[3.2.1]oct-3-yl)amino]carbonyl}-1H-indazol-1H-1,2,3-triazol-1-yl]acetate,
N-(8-Methyl-8-azabicyclo[3.2.1]oct-3-yl)-5-(phenylsulfonyl)-1H-indazole-3-carboxamide hydroformate,
N-(8-Methyl-8-azabicyclo[3.2.1]oct-3-yl)-5-(phenylsulfonyl)-1H-indazole-3-carboxamide,
N-(8-Methyl-8-azabicyclo[3.2.1]oct-3-yl)-6-(4-methyl-1,3-thiazol-2-yl)-1H-indazole-3-carboxamide hydroformate,
N-(8-Methyl-8-azabicyclo[3.2.1]oct-3-yl)-6-(4-methyl-1,3-thiazol-2-yl)-1H-indazole-3-carboxamide,
N-(8-Methyl-8-azabicyclo[3.2.1]oct-3-yl)-6-(5-methyl-1,3-thiazol-2-yl)-1H-indazole-3-carboxamide hydroformate,
N-(8-Methyl-8-azabicyclo[3.2.1]oct-3-yl)-6-(5-methyl-1,3-thiazol-2-yl)-1H-indazole-3-carboxamide,
N-(8-Methyl-8-azabicyclo[3.2.1]oct-3-yl)-6-(nitro)-1H-indazole-3-carboxamide hydroformate,
N-(8-Methyl-8-azabicyclo[3.2.1]oct-3-yl)-6-(nitro)-1H-indazole-3-carboxamide,
N-(endo-8-Methyl-8-azabicyclo[3.2.1]oct-3-yl)-5-(1,3-thiazol-2-yl)-1H-indazole-3-carboxamide hydroformate,
N-(endo-8-Methyl-8-azabicyclo[3.2.1]oct-3-yl)-5-(1,3-thiazol-2-yl)-1H-indazole-3-carboxamide,
N-(endo-8-Methyl-8-azabicyclo[3.2.1]oct-3-yl)-5-(nitro)-1H-indazole-3-carboxamide hydroformate,
N-(endo-8-Methyl-8-azabicyclo[3.2.1]oct-3-yl)-5-(nitro)-1H-indazole-3-carboxamide,
N-(endo-8-Methyl-8-azabicyclo[3.2.1]oct-3-yl)-5-(trifluoromethoxy)-1H-indazole-3-carboxamide hydroformate, N-(endo-8-Methyl-8-azabicyclo[3.2.1]oct-3-yl)-5-(trifluoromethoxy)-1H-indazole-3-carboxamide,
N-(endo-8-Methyl-8-azabicyclo[3.2.1]oct-3-yl)-5-{[(propylamino)carbonyl]amino}-1H-indazole-3-carboxamide hydroformate,
N-(endo-8-Methyl-8-azabicyclo[3.2.1]oct-3-yl)-5-{[(propylamino)carbonyl]amino}-1H-indazole-3-carboxamide,
N-(endo-8-Methyl-8-azabicyclo[3.2.1]oct-3-yl)-6-(4-methyl-1,3-thiazol-2-yl)-1H-indazole-3-carboxamide hydroformate,
N-(endo-8-Methyl-8-azabicyclo[3.2.1]oct-3-yl)-6-(4-methyl-1,3-thiazol-2-yl)-1H-indazole-3-carboxamide,
N-(endo-8-Methyl-8-azabicyclo[3.2.1]oct-3-yl)-6-(5-methyl-1,3-thiazol-2-yl)-1H-indazole-3-carboxamide hydroformate,
N-(endo-8-Methyl-8-azabicyclo[3.2.1]oct-3-yl)-6-(5-methyl-1,3-thiazol-2-yl)-1H-indazole-3-carboxamide,
N-(endo-8-Methyl-8-azabicyclo[3.2.1]oct-3-yl)-6-(nitro)-1H-indazole-3-carboxamide hydroformate,
N-(endo-8-Methyl-8-azabicyclo[3.2.1]oct-3-yl)-6-(nitro)-1H-indazole-3-carboxamide,
N-(endo-8-Methyl-8-azabicyclo[3.2.1]oct-3-yl)-6-(trifluoromethoxy)-1H-indazole-3-carboxamide hydroformate,
N-(endo-8-Methyl-8-azabicyclo[3.2.1]oct-3-yl)-6-(trifluoromethoxy)-1H-indazole-3-carboxamide,
N-(endo-8-Methyl-8-azabicyclo[3.2.1]oct-3-yl)-6-[1-(2-piperidin-1-ylethyl)-1H-1,2,3-triazol-4-yl]-1H-indazole-3-carboxamide trihydroformate,
N-(endo-8-Methyl-8-azabicyclo[3.2.1]oct-3-yl)-6-[1-(2-piperidin-1-ylethyl)-1H-1,2,3-triazol-4-yl]-1H-indazole-3-carboxamide,
N-(exo-8-Methyl-8-azabicyclo[3.2.1]oct-3-yl)-5-(1,3-thiazol-2-yl)-1H-indazole-3-carboxamide hydroformate,
N-(exo-8-Methyl-8-azabicyclo[3.2.1]oct-3-yl)-5-(1,3-thiazol-2-yl)-1H-indazole-3-carboxamide,
N-(exo-8-Methyl-8-azabicyclo[3.2.1]oct-3-yl)-5-(nitro)-1H-indazole-3-carboxamide hydroformate,
N-(exo-8-Methyl-8-azabicyclo[3.2.1]oct-3-yl)-5-(nitro)-1H-indazole-3-carboxamide,
N-(exo-8-Methyl-8-azabicyclo[3.2.1]oct-3-yl)-5-(trifluoromethoxy)-1H-indazole-3-carboxamide hydroformate,
N-(exo-8-Methyl-8-azabicyclo[3.2.1]oct-3-yl)-5-(trifluoromethoxy)-1H-indazole-3-carboxamide,
N-(exo-8-Methyl-8-azabicyclo[3.2.1]oct-3-yl)-6-(4-methyl-1,3-thiazol-2-yl)-1H-indazole-3-carboxamide hydroformate,
N-(exo-8-Methyl-8-azabicyclo[3.2.1]oct-3-yl)-6-(4-methyl-1,3-thiazol-2-yl)-1H-indazole-3-carboxamide,
N-(exo-8-Methyl-8-azabicyclo[3.2.1]oct-3-yl)-6-(5-methyl-1,3-thiazol-2-yl)-1H-indazole-3-carboxamide hydroformate,
N-(exo-8-Methyl-8-azabicyclo[3.2.1]oct-3-yl)-6-(5-methyl-1,3-thiazol-2-yl)-1H-indazole-3-carboxamide,
N-(exo-8-Methyl-8-azabicyclo[3.2.1]oct-3-yl)-6-(nitro)-1H-indazole-3-carboxamide hydroformate,
N-(exo-8-Methyl-8-azabicyclo[3.2.1]oct-3-yl)-6-(nitro)-1H-indazole-3-carboxamide,
and pharmaceutically acceptable salts thereof.

According to a further compound and/or method aspect of the invention, the compounds of Formulas I, II and III are selected from:
2-[(6-Methoxy-1H-indazol-3-yl)carbonyl]octahydro-2H-pyrido[1,2-a]pyrazine hydroformate,
7-Methoxy-N-(endo-9-methyl-9-azabicyclo[3.3.1]non-3-yl)-1H-indazole-3-carboxamide hydroformate,
6-Methoxy-N-(endo-8-methyl-8-azabicyclo[3.2.1]oct-3-yl)-1,2-benzisothiazole-3-carboxamide hydroformate,
6-Methoxy-N-(exo-8-methyl-8-azabicyclo[3.2.1]oct-3-yl)-1,2-benzisothiazole-3-carboxamide hydroformate,
N-(2-Methyl-2-azabicyclo[2.2.1]hept-5-yl)-5-(trifluoromethoxy)-1H-indazole-3-carboxamide hydroformate,
6-Methoxy-N-(2-methyl-2-azabicyclo[2.2.1]hept-5-yl)-1H-indazole-3-carboxamide hydroformate,
N-(2-Methyl-2-azabicyclo[2.2.1]hept-5-yl)-6-(4-methyl-1,3-thiazol-2-yl)-1H-indazole-3-carboxamide hydroformate,
5-Difluoromethoxy-N-(endo-8-methyl-8-azabicyclo[3.2.1]oct-3-yl)-1H-indazole-3-carboxamide hydroformate,
5-Difluoromethoxy-N-(exo-8-methyl-8-azabicyclo[3.2.1]oct-3-yl)-1H-indazole-3-carboxamide hydroformate,
5-Difluoromethoxy-N-(8-methyl-8-azabicyclo[3.2.1]oct-3-yl)-1H-indazole-3-carboxamide hydroformate,
6-Difluoromethoxy-N-(endo-8-methyl-8-azabicyclo[3.2.1]oct-3-yl)-1H-indazole-3-carboxamide hydroformate,
6-Difluoromethoxy-N-(8-methyl-8-azabicyclo[3.2.1]oct-3-yl)-1H-indazole-3-carboxamide hydroformate,
N-(8-Methyl-8-azabicyclo[3.2.1]oct-3-yl)-5-(4-methyl-1,3-thiazol-2-yl)-1H-indazole-3-carboxamide,
N-(exo-8-Methyl-8-azabicyclo[3.2.1]oct-3-yl)-5-(4-methyl-1,3-thiazol-2-yl)-1H-indazole-3-carboxamide hydroformate,
N-(2-Methyl-2-azabicyclo[2.2.1]hept-5-yl)-5-(4-methyl-1,3-thiazol-2-yl)-1H-indazole-3-carboxamide hydroformate,
6-(3,6-Dihydro-2H-pyran-4-yl)-N-(2-methyl-2-azabicyclo[2.2.1]hept-5-yl)-1H-indazole-3-carboxamide hydroformate,
N-(2-Methyl-2-azabicyclo[2.2.1]hept-5-yl)-6-(5-methyl-1,3-thiazol-2-yl)-1H-indazole-3-carboxamide hydroformate,
6-Difluoromethoxy-N-(2-methyl-2-azabicyclo[2.2.1]hept-5-yl)-1H-indazole-3-carboxamide hydroformate,
N-(2-Methyl-2-azabicyclo[2.2.1]hept-5-yl)-6-(1,3-thiazol-2-yl)-1H-indazole-3-carboxamide hydroformate,
N-(2-Methyl-2-azabicyclo[2.2.1]hept-5-yl)-5-(5-methyl-1,3-thiazol-2-yl)-1H-indazole-3-carboxamide hydroformate,
N-(2-Methyl-2-azabicyclo[2.2.1]hept-5-yl)-6-(trifluoromethoxy)-1H-indazole-3-carboxamide hydroformate,
N-(endo-8-Methyl-8-azabicyclo[3.2.1]oct-3-yl)-5-(4-methyl-1,3-thiazol-2-yl)-1H-indazole-3-carboxamide hydroformate,
N-(2-Methyl-2-azabicyclo[2.2.1]hept-5-yl)-6-(2-thienyl)-1H-indazole-3-carboxamide hydroformate,
N-(2-Methyl-2-azabicyclo[2.2.1]hept-5-yl)-5-(1,3-oxazol-2-yl)-1H-indazole-3-carboxamide hydroformate,
5-(3,6-Dihydro-2H-pyran-4-yl)-N-(2-methyl-2-azabicyclo[2.2.1]hept-5-yl)-1H-indazole-3-carboxamide hydroformate,
5-Methoxy-N-(2-methyl-2-azabicyclo[2.2.1]hept-5-yl)-1H-indazole-3-carboxamide hydroformate,
N-[(rel-1S,4S,5S)-2-Methyl-2-azabicyclo[2.2.1]hept-5-yl]-6-(4-methyl-1,3-thiazol-2-yl)-1H-indazole-3-carboxamide,
N-[(rel-1S,4S,5R)-2-Methyl-2-azabicyclo[2.2.1]hept-5-yl]-6-(4-methyl-1,3-thiazol-2-yl)-1H-indazole-3-carboxamide,
N-[(rel-1S,4S,5R)-2-Methyl-2-azabicyclo[2.2.1]hept-5-yl]-5-(trifluoromethoxy)-1H-indazole-3-carboxamide,
N-[(rel-1S,4S,5S)-2-Methyl-2-azabicyclo[2.2.1]hept-5-yl]-5-(trifluoromethoxy)-1H-indazole-3-carboxamide,
N-(2-Methyl-2-azabicyclo[2.2.1]hept-5-yl)-5-(1,3-thiazol-2-yl)-1H-indazole-3-carboxamide hydroformate, N-(endo-8-methyl-8-azabicyclo[3.2.1]oct-3-yl)-5-(1,3-ox-azol-2-yl)-1H-indazole-3-carboxamide hydroformate, N-(2-Methyl-2-azabicyclo[2.2.1]hept-5-yl)-6-(5-methyl-1,3-thiazol-2-yl)-1H-indazole-3-carboxamide hydroformate, N-(2-Methyl-2-azabicyclo[2.2.1]hept-5-yl)-5-(trifluoromethoxy)-1H-indazole-3-carboxamide hydroformate, N-(2-Methyl-2-azabicyclo[2.2.1]hept-5-yl)-6-(4-methyl-1,3-thiazol-2-yl)-1H-indazole-3-carboxamide hydroformate, 6-Amino-N-(2-methyl-2-azabicyclo[2.2.1]hept-5-yl)-1H-indazole-3-carboxamide, 5-(1-Benzyl-1H-1,2,3-triazol-4-yl)-N-(8-methyl-8-azabicyclo[3.2.1]oct-3-yl)-1H-indazole-3-carboxamide dihydroformate, 6-{[(Cyclopentylamino)carbonyl]amino}-N-(endo-8-methyl-8-azabicyclo[3.2.1]oct-3-yl)-1H-indazole-3-carboxamide hydroformate, N-(endo-8-Methyl-8-azabicyclo[3.2.1]oct-3-yl)-6-{[(propylamino)carbonyl]amino}-1H-indazole-3-carboxamide hydroformate, 5-({[(4-Fluorophenyl)amino]carbonyl}amino)-N-(endo-8-methyl-8-azabicyclo[3.2.1]oct-3-yl)-1H-indazole-3-carboxamide hydroformate, 6-({[(4-Fluorobenzyl)amino]carbonyl}amino)-N-(endo-8-methyl-8-azabicyclo[3.2.1]oct-3-yl)-1H-indazole-3-carboxamide hydroformate, 5-({[(3-Methoxyphenyl)amino]carbonyl}amino)-N-(endo-8-methyl-8-azabicyclo[3.2.1]oct-3-yl)-1H-indazole-3-carboxamide hydroformate, 6-({[(3-Methoxybenzyl)amino]carbonyl}amino)-N-(endo-8-methyl-8-azabicyclo[3.2.1]oct-3-yl)-1H-indazole-3-carboxamide hydroformate, N-(8-methyl-8-azabicyclo[3.2.1]oct-3-yl)-5-(2-oxo-3-propylimidazolidin-1-yl)-1H-indazole-3-carboxamide hydroformate, and pharmaceutically acceptable salts thereof.

According to a further compound and/or method aspect of the invention, the compounds of Formulas I, II and III are selected from:

5-(3,6-Dihydro-2H-pyran-4-yl)-N-(endo-9-methyl-9-azabicyclo[3.3.1]non-3-yl)-1H-indazole-3-carboxamide hydroformate, 6-Methoxy-N-(endo-9-methyl-9-azabicyclo[3.3.1]non-3-yl)-1,2-benzisothiazole-3-carboxamide, 6-Methoxy-N-(endo-9-methyl-9-azabicyclo[3.3.1]non-3-yl)-1H-indazole-3-carboxamide hydroformate, 6-Methoxy-N-(endo-9-methyl-9-azabicyclo[3.3.1]non-3-yl)-1H-indazole-3-carboxamide, 5-Methoxy-N-(endo-9-methyl-9-azabicyclo[3.3.1]non-3-yl)-1H-indazole-3-carboxamide hydroformate, N-(endo-9-Methyl-9-azabicyclo[3.3.1]non-3-yl)-5-(trifluoromethoxy)-1H-indazole-3-carboxamide hydroformate, N-(endo-9-Methyl-9-azabicyclo[3.3.1]non-3-yl)-5-nitro-1H-indazole-3-carboxamide hydroformate, 5-Amino-N-(endo-9-methyl-9-azabicyclo[3.3.1]non-3-yl)-H-indazole-3-carboxamide hydroformate, N-(8-Methyl-8-azabicyclo[3.2.1]oct-3-yl)-5-(nitro)-1H-indazole-3-carboxamide hydroformate, N-(8-Methyl-8-azabicyclo[3.2.1]oct-3-yl)-5-(nitro)-1H-indazole-3-carboxamide, 6-Methoxy-N-(8-methyl-8-azabicyclo[3.2.1]oct-3-yl)-1,2-benzisothiazole-3-carboxamide hydroformate, N-(8-Methyl-8-azabicyclo[3.2.1]oct-3-yl)-5-(4-methyl-1,3-thiazol-2-yl)-1H-indazole-3-carboxamide hydroformate, N-(8-methyl-8-azabicyclo[3.2.1]oct-3-yl)-5-(1,3-oxazol-2-yl)-1H-indazole-3-carboxamide hydroformate, 5-(1-Benzyl-1H-pyrazol-4-yl)-N-(endo-9-methyl-9-azabicyclo[3.3.1]non-3-yl)-1H-indazole-3-carboxamide hydroformate, 5-(2,3'-Bithien-5-yl)-N-(endo-9-methyl-9-azabicyclo[3.3.1]non-3-yl)-1H-indazole-3-carboxamide hydroformate, 5-(3-Furyl)-N-(endo-9-methyl-9-azabicyclo[3.3.1]non-3-yl)-1H-indazole-3-carboxamide hydroformate, N-(endo-9-Methyl-9-azabicyclo[3.3.1]non-3-yl)-5-(3-thienyl)-1H-indazole-3-carboxamide hydroformate, N-(endo-9-Methyl-9-azabicyclo[3.3.1]non-3-yl)-5-(4-methyl-2-thienyl)-1H-indazole-3-carboxamide hydroformate, N-(endo-9-Methyl-9-azabicyclo[3.3.1]non-3-yl)-6-(2-thienyl)-H-indazole-3-carboxamide hydroformate, N-(endo-9-Methyl-9-azabicyclo[3.3.1]non-3-yl)-6-(4-methyl-2-thienyl)-1H-indazole-3-carboxamide hydroformate, N-(endo-9-Methyl-9-azabicyclo[3.3.1]non-3-yl)-5-(1,3-thiazol-2-yl)-1H-indazole-3-carboxamide hydroformate, N-(endo-9-Methyl-9-azabicyclo[3.3.1]non-3-yl)-5-(1,3-oxazol-2-yl)-1H-indazole-3-carboxamide hydroformate, N-(endo-9-Methyl-9-azabicyclo[3.3.1]non-3-yl)-5-(1-methyl-1H-imidazol-2-yl)-1H-indazole-3-carboxamide dihydroformate, N-(endo-9-Methyl-9-azabicyclo[3.3.1]non-3-yl)-6-(1,3-thiazol-2-yl)-1H-indazole-3-carboxamide hydroformate, N-(endo-9-Methyl-9-azabicyclo[3.3.1]non-3-yl)-5-(2-trimethylsilylethyn-1-yl)-1H-indazole-3-carboxamide, N-(endo-9-Methyl-9-azabicyclo[3.3.1]non-3-yl)-5-(morpholin-4-yl)-1H-indazole-3-carboxamide hydroformate, N-(endo-9-Methyl-9-azabicyclo[3.3.1]non-3-yl)-5-(pyrrolidin-1-yl)-1H-indazole-3-carboxamide hydroformate, N-(endo-9-Methyl-9-azabicyclo[3.3.1]non-3-yl)-5-(thiomorpholin-4-yl)-1H-indazole-3-carboxamide hydroformate, N-(8-Methyl-8-azabicyclo[3.2.1]oct-3-yl)-6-[1-(2-piperidin-1-ylethyl)-1H-1,2,3-triazol-4-yl]-1H-indazole-3-carboxamide trihydroformate, N-(8-Methyl-8-azabicyclo[3.2.1]oct-3-yl)-6-[1-(2-piperidin-1-ylethyl)-1H-1,2,3-triazol-4-yl]-1H-indazole-3-carboxamide, 5-(1-Benzyl-1H-1,2,3-triazol-4-yl)-N-(8-methyl-8-azabicyclo[3.2.1]oct-3-yl)-1H-indazole-3-carboxamide dihydroformate, 5-(1-Benzyl-1H-1,2,3-triazol-4-yl)-N-(endo-8-methyl-8-azabicyclo[3.2.1]oct-3-indazole-3-carboxamide dihydroformate, 5-{[(Cyclopentylamino)carbonyl]amino}-N-(8-methyl-8-azabicyclo[3.2.1]oct-3-yl)-1H-indazole-3-carboxamide hydroformate, 5-{[(Cyclopentylamino)carbonyl]amino}-N-(8-methyl-8-azabicyclo[3.2.1]oct-3-yl)-1H-indazole-3-carboxamide, N-(8-Methyl-8-azabicyclo[3.2.1]oct-3-yl)-5-{[(propylamino)carbonyl]amino}-1H-indazole-3-carboxamide hydroformate, N-(8-Methyl-8-azabicyclo[3.2.1]oct-3-yl)-5-{[(propylamino)carbonyl]amino}-1H-indazole-3-carboxamide, 6-{[(Cyclopentylamino)carbonyl]amino}-N-(8-methyl-8-azabicyclo[3.2.1]oct-3-yl)-1H-indazole-3-carboxamide hydroformate, N-(8-Methyl-8-azabicyclo[3.2.1]oct-3-yl)-6-{[(propylamino)carbonyl]amino}-1H-indazole-3-carboxamide hydroformate, 5-({[(4-Fluorophenyl)amino]carbonyl}amino)-N-(8-methyl-8-azabicyclo[3.2.1]oct-3-yl)-1H-indazole-3-carboxamide hydroformate, 6-({[(4-Fluorobenzyl)amino]carbonyl}amino)-N-(8-methyl-8-azabicyclo[3.2.1]oct-3-yl)-1H-indazole-3-carboxamide hydroformate, 5-({[(3-Methoxyphenyl)amino]carbonyl }amino)-N-(8-methyl-8-azabicyclo[3.2.1]oct-3-yl)-1H-indazole-3-carboxamide hydroformate, 6-({[(3-Methoxybenzyl)amino]carbonyl}amino)-N-(8-methyl-8-azabicyclo[3.2.1]oct-3-yl)-1H-indazole-3-carboxamide hydroformate, N-(endo-8-methyl-8-azabicyclo[3.2.1]oct-3-yl)-5-(2-oxo-3-propylimidazolidin-1-yl)-1H-indazole-3-carboxamide hydroformate, 5-Difluoromethoxy-N-(8-methyl-8-azabicyclo[3.2.1]oct-3-yl)-1H-indazole-3-carboxamide, 5-Difluoromethoxy-N-(endo-8-methyl-8-azabicyclo[3.2.1]oct-3-yl)-1H-indazole-3-carboxamide, 5-Difluoromethoxy-N-(exo-8-methyl-8-azabicyclo[3.2.1]oct-3-yl)-1H-indazole-3-carboxamide, 5-Difluoromethoxy-N-(8-methyl-8-azabicyclo[3.2.1]oct-3-yl)-1H-indazole-3-carboxamide hydrochloride, 5-Difluoromethoxy-N-(endo-8-methyl-8-azabicyclo[3.2.1]oct-3-yl)-1H-indazole-3-carboxamide hydrochloride, 5-Difluoromethoxy-N-(exo-8-methyl-8-azabicyclo[3.2.1]oct-3-yl)-1H-indazole-3-carboxamide hydrochloride, 6-Difluoromethoxy-N-(8-methyl-8-azabicyclo[3.2.1]oct-3-yl)-1H-indazole-3-carboxamide, 6-Difluoromethoxy-N-(endo-8-methyl-8-azabicyclo[3.2.1]oct-3-yl)-1H-indazole-3-carboxamide, 6-Difluoromethoxy-N-(exo-8-methyl-8-azabicyclo[3.2.1]oct-3-yl)-1H-indazole-3-carboxamide, 6-Difluoromethoxy-N-(8-methyl-8-azabicyclo[3.2.1]oct-3-yl)-1H-indazole-3-carboxamide hydrochloride, 6-Difluoromethoxy-N-(endo-8-methyl-8-azabicyclo[3.2.1]oct-3-yl)-1H-indazole-3-carboxamide hydrochloride, 6-Difluoromethoxy-N-(exo-8-methyl-8-azabicyclo[3.2.1]oct-3-yl)-1H-indazole-3-carboxamide hydrochloride, and 6-Difluoromethoxy-N-(exo-8-methyl-8-azabicyclo[3.2.1]oct-3-yl)-1H-indazole-3-carboxamide hydroformate, and pharmaceutically acceptable salts thereof.

Preferred aspects include pharmaceutical compositions comprising a compound of this invention and a pharmaceutically acceptable carrier and, optionally, another active agent as discussed below; a method of stimulating or activating inhibiting alpha-7 nicotinic receptors, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc. method of treating a disease state modulated by nicotinic alpha-7 activity, in a mammal, e.g., a human, e.g., those mentioned herein.

The compounds of the present invention may be prepared conventionally. Some of the known processes that can be used are described below. All starting materials are known or can be conventionally prepared from known starting materials.

The synthesis of similar compounds is disclosed in copending application Ser. No. 11/018,429, filed Dec. 22, 2004, the entire disclosure of which is hereby incorporated by reference.

Acids that were used in the preparation of the bicyclobase amides were commercially available or were prepared by known procedures described in the literature or as described below. For example, indazole-3-carboxylic acid was commercially available. A variety of the simple substituted indazole-3-acids, such as the bromoindazole acids, were prepared from the corresponding isatins by basic hydrolysis, diazotization, and reduction (Snyder, H. R.; et al. *J. Am. Chem. Soc.* 1952, 74, 2009).

Some substituted indazole-3-acids were prepared by modifying existing indazole acids or esters. For example, 5-nitroindazole-3-acid was prepared by nitration of indazole-3-acid (Kamm, O.; Segur, J. B. *Org. Syn. Coll. Vol* 1. 1941, 372). 6-Nitroindazole-3-acid was prepared from 3-iodo-6-nitroindazole using copper (I) cyanide followed by hydrolysis. Some non-aromatic heterocyclic derivatives were prepared from the bromides by metal-halogen exchange, trapping of indazole aryllithiums with ketones, followed by reduction or acid mediated elimination. Aromatic substituted indazole-3-acids were prepared from the bromides via palladium mediated cross-coupling with boronic acids or aryl zinc reagents (Reeder, M. R.; et. al. *Org. Proc. Res. Devel.* 2003, 7, 696).

Some substituted indazole-3-acids were prepared from simple benzene derivatives. For example, 5-difluoromethoxyindazole-3-acid was prepared from 3-bromo-4-nitrophenol by reaction with ethyl difluoroacetate, reaction with diethyl malonate, decarboxylative saponification, esterification, reduction of the nitro group, and diazotization. 6-Difluoromethoxyindazole-3-acid was prepared in a similar manner from 2-bromo-5-difluoromethoxynitrobenzene. The 2-bromo-5-difluoromethoxynitrobenzene used in that preparation was prepared from 4-nitrophenol by ether formation, nitro reduction with concomitant protection as the amide, nitration, amide hydrolysis, and a Sandmeyer reaction with copper (I) bromide.

The benzisoxazole- and benzisoxazolecarboxylic acids were prepared using similar strategies outlined for the indazole acids. For example, ethyl 6-bromobenzisoxazole-3-carboxylate was prepared from 2,5-dibromonitrobenzene by reaction with diethyl malonate, saponification and decarboxylation, and reaction with isoamylnitrite. Ethyl benzisoxazole-3-carboxylate was obtained by hydrogenolysis of the 6-bromo derivative. 3-Benzisothiazolecarboxylic acid was prepared from thiophenol by reaction with oxalyl chloride and aluminum chloride followed by treatment with hydroxylamine, hydrogen peroxide, and sodium hydroxide.

Bicycloamines that can be used in the preparation of the bicyclobase amides are commercially available, can be prepared by known procedures described in the literature, or as described below. For example, 2-Methyl-2-azabicyclo[2.2.2]octan-5-amine was obtained by the reduction of the 2-Boc-2-azabicyclo[2.2.2]octan-5-amine (*J. Med. Chem.* 1973, 16, 853; *Synthesis* 1979, 50; WO97/40016). 2-Methyl-2-azabicyclo[2.2.1]heptan-5-amine (*Tetrahedron* 1998, 54, 8047-8054; *J. Med. Chem.* 1992, 35, 2184-2191), octahydroindolizin-6-amine (U.S. Pat. No. 4,213,983), 2-azabicyclo[2.2.1]heptan-5-amine (*J. Med. Chem.*1990, 33, 1924), 8-azabicyclo[3.2.1]octan-3-amine (WO38680A1; *J. Med. Chem.* 1993, 36, 3707; *J. Med. Chem.* 2001, 44, 1815), and 9-azabicyclo[3.3.1]nonan-3-amine (WO38680A1; *J. Med. Chem.* 1993, 36, 3707; *J. Med. Chem.* 2001, 44, 1815) were prepared according to literature procedures. 8-Methyl-8-azabicyclo[3.2.1]octan-3-amine was obtained from commercial sources as a variable mixture of endo- and exo-isomers whereas pure exo- and pure endo-isomers were prepared according to the literature (*J. Med. Chem.* 1998, 41, 988). 3,8-Dimethyl-8-azabicyclo[3.2.1]octan-3-amine was prepared from 3-aminotropane by exposure to di-tert-butyl dicarbonate followed by lithium aluminum hydride reduction. endo-9-Methyl-9-azabicyclo[3.3.1]nonan-3-amine was obtained by the acid hydrolysis of granisetron. exo-9-Methyl-9-azabicyclo[3.3.1]nonan-3-amine and a mixture of endo- and exo-9-Methyl-9-azabicyclo[3.3. 1]nonan-3-amine may be obtained according to the procedures set forth in European Patent Application No. 0 013 138 A1. 8-Methyl-3,8-diazabicyclo[3.2.1]octane and 3-methyl-3,8-diazabicyclo[3.2.1]octane were prepared from the commercially available 8-Boc protected base by lithium aluminum hydride reduction and reductive alkylation followed by deprotection, respectively.

The bicyclobase amide can be prepared by the coupling reaction of acids with the bicycloamine and HBTU or HOBt and EDCI in DMF, or by converting the acids to the corresponding acid chloride and then reaction with the bicycloamine (Macor, J. E.; Gurley, D.; Lanthom, T.; Loch, J.; Mack, R. A.; Mullen, G.; Tran, O.; Wright, N.; and J. E. Macor et al., "The 5-HT3-Antagonist Tropisetron (ICS 205-930) is a Potent and Selective α-7 Nicotinic Receptor Partial Agonist," Bioorg. Med. Chem. Lett. 2001, 9, 319-321). The couplings are generally performed at room temperatures for 18-24 hours. Thioamide analogs can be prepared from the amides by reaction with Lawesson's reagent (Wipf P.; Kim, Y.; Goldstein, D. M., J. Am. Chem. Soc., 1995,117, 11106). Bicyclobase methylenamine analogs may be prepared from bicyclobase amides by standard reduction procedures as described, for example, below. The resultant adducts can be isolated and purified by standard techniques, such as chromatography or recrystallization, practiced by those skilled in the art.

The nicotinic ligands can, alternatively, be prepared by modification of other nicotinic ligands. For example, the 5-(3-thiophene) ligand was prepared from the corresponding bromide ligand by a palladium-catalyzed cross-coupling reaction. Other halogen-substituted ligands served as precursors for modified ligands where appropriate. As a final example, urea analogs were prepared from aniline substituted analogs.

One of ordinary skill in the art will recognize that compounds of Formulas I, II, or III can exist in different tautomeric and geometrical isomeric forms. For example, compound containing the 8-methyl-8-azabicyclo[3.2.1]octan-3-amino, or 9-methyl-9-azabicyclo[3.3.1]non-3-amino structures can be in the form of the endo isomer, exo isomer, or mixtures thereof. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I, II, or III can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formulas I-III, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their alpha-7 stimulating activity and, preferably their high degree of selectivity, the compounds of the present invention can be administered to anyone needing stimulation of alpha-7 receptors. Administration may be accomplished according to patient needs, for example, orally, nasally, parenterally (subcutaneously, intraveneously, intramuscularly, intrastemally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or memory loss, e.g., other $\alpha$-7 agonists, PDE4 inhibitors, calcium channel blockers, muscarinic m1 and m2 modulators, adenosine receptor modulators, amphakines NMDA-R modulators, mGluR modulators, dopamine modulators, serotonin modulators, canabinoid modulators, and cholinesterase inhibitors (e.g., donepezil, rivastigimine, and glanthanamine). In such combinations, each active ingredient can be administered either in accordance with their usual dosage range or a dose below their usual dosage range.

The compounds of the invention can be used in conjunction with "positive modulators" which enhance the efficacy of nicotinic receptor agonists. See, e.g., the positive modulators disclosed in WO 99/56745, WO 01/32619, and WO 01/32622. Such combinational therapy can be used in treating conditions/diseases associated with reduced nicotinic transmission.

Further the compounds may be used in conjunction with compounds that bind to A$\beta$ peptides and thereby inhibit the binding of the peptides to $\alpha$7nACh receptor subtypes. See, e.g., WO 99/62505.

The present invention further includes methods of treatment that involve activation of $\alpha$-7 nicotinic receptors. Thus, the present invention includes methods of selectively activating/stimulating $\alpha$-7 nicotinic receptors in a patient (e.g., a mammal such as a human) wherein such activation/stimulation has a therapeutic effect, such as where such activation may relieve conditions involving neurological syndromes, such as the loss of memory, especially long-term memory. Such methods comprise administering to a patient (e.g., a mammal such as a human), an effective amount of a compound of Formulas I, II, or III, alone or as part of a formulation, as disclosed herein.

In accordance with a method aspect of the invention, there is provided a method of treating a patient (e.g., a mammal such as a human) suffering from a disease state (e.g., memory impairment) comprising administering to the patient a compound according to Formulas I, II, or III. Preferably, the disease state involves decreased nicotinic acetylcholine receptor activity.

In accordance with a method aspect of the invention there is provided a method for the treatment or prophylaxis of a disease or condition resulting from dysfunction of nicotinic acetylcholine receptor transmission in a patient (e.g., a mammal such as a human) comprising administering an effective amount of a compound according to Formulas I, II, or III.

In accordance with a method aspect of the invention there is provided a method for the treatment or prophylaxis of a disease or condition resulting from defective or malfunctioning nicotinic acetylcholine receptors, particularly $\alpha$7nACh receptors, in a patient (e.g., a mammal such as a human) comprising administering an effective amount of a compound according to Formulas I, II, or III.

In accordance with a method aspect of the invention there is provided a method for the treatment or prophylaxis of a disease or condition resulting from suppressed nicotinic acetylcholine receptor transmission in a patient (e.g., a mammal such as a human) comprising administering an amount of a compound according to Formulas I, II, or III effective to activate $\alpha$7nACh receptors.

In accordance with another method aspect of the invention there is provided a method for the treatment or prophylaxis of a psychotic disorder, a cognition impairment (e.g., memory impairment), or neurodegenerative disease in a patient (e.g., a mammal such as a human) comprising administering an effective amount of a compound according to Formulas I, II, or III.

In accordance with another method aspect of the invention there is provided a method for the treatment or prophylaxis of a disease or condition resulting from loss of cholinergic synapses in a patient (e.g., a mammal such as a human) comprising administering an effective amount of a compound according to Formulas I, II, or III.

In accordance with another method aspect of the invention there is provided a method for the treatment or prophylaxis of a neurodegenerative disorder by activation of α7nACh receptors in a patient (e.g., a mammal such as a human) comprising administering an effective amount of a compound according to Formulas I, II, or III.

In accordance with another method aspect of the invention there is provided a method for protecting neurons in a patient (e.g., a mammal such as a human) from neurotoxicity induced by activation of α7nACh receptors comprising administering an effective amount of a compound according to Formulas I, II, or III.

In accordance with another method aspect of the invention there is provided a method for the treatment or prophylaxis of a neurodegenerative disorder by inhibiting the binding of Aβ peptides to α7nACh receptors in a patient (e.g., a mammal such as a human) comprising administering an effective amount of a compound according to Formulas I, II, or III.

In accordance with another method aspect of the invention there is provided a method for protecting neurons in a patient (e.g., a mammal such as a human) from neurotoxicity induced by Aβ peptides comprising administering an effective amount of a compound according to Formulas I, II, or III.

In accordance with another method aspect of the invention there is provided a method for alleviating inhibition of cholinergic function induced by Aβ peptides in a patient (e.g., a mammal such as a human) comprising administering an effective amount of a compound according to Formulas I, II, or III.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention are nicotinic alpha-7 ligands, preferably agonists, especially partial agonists, for the alpha-7 nicotinic acetylcholine receptor. Assays for determining nicotinic acetylcholine activity are known within the art. See, e.g., Davies, A. R., et al., *Characterisation of the binding of [3H]methyllycaconitine: a new radioligand for labelling alpha 7-type neuronal nicotinic acetylcholine receptors.* Neuropharmacology, 1999. 38(5): p. 679-90. As agonists for α7nACh receptors, the compounds are useful in the prophylaxis and treatment of a variety of diseases and conditions associated with the central nervous system. Nicotinic acetylcholine receptors are ligand-gastrol ion-channel receptors that are composed of five subunit proteins which form a central ion-conducting pore. Presently, there are eleven known neuronal nACh receptor subunits (α2-α9 and β2-β4). There are also five further subunits expressed in the peripheral nervous system (α1, β1, γ, δ, ε).

The nACh receptor subtypes can be homopentameric or heteropentameric. The subtype which has received considerable attention is the homopentameric α7 receptor subtype formed from five α7 subunits. The α7nACh receptors exhibit a high affinity for nicotine (agonist) and for α-bungarotoxin (antagonist). Studies have shown the α7nACh receptor agonists can be useful in the treatment of psychotic diseases, neurodegenerative diseases, and cognitive impairments, among other things. While nicotine is a known agonist, there is a need for the development of other α7nACh receptor agonists, especially selective agonists, which are less toxic or exhibit fewer side effects than nicotine.

The compound anabaseine, i.e., 2-(3-pyridyl)-3,4,5,6-tetrahydropyridine is a naturally occurring toxin in certain marine worms (nemertine worms) and ants. See, e.g., Kem et al., Toxicon, 9:23, 1971. Anabaseine is a potent activator of mammalian nicotinic receptors. See, e.g., Kem, Amer. Zoologist, 25, 99, 1985. Certain anabaseine analogs such as anabasine and DMAB (3-[4-(dimethylamino)benzylidene]-3,4,5,6-tetrahydro-2',3'-bipyridine) are also known nicotinic receptor agonists. See, e.g., U.S. Pat. No. 5,602,257 and WO 92/15306. One particular anabaseine analog, (E-3-[2,4-dimethoxy-benzylidene]-anabaseine, also known as GTS-21 and DMXB (see, e.g., U.S. Pat. No. 5,741,802), is a selective partial α7nACh receptor agonist that has been studied extensively. For example, abnormal sensory inhibition is a sensory processing deficit in schizophrenics and GTS-21 has been found to increase sensory inhibition through interaction with α7nACh receptors. See, e.g., Stevens et al., Psychopharmacology, 136: 320-27 (1998).

Another compound which is known to be a selective α7nACh receptor agonist is Tropisetron, i.e., 1αH, 5αH-tropan-3α-yl indole-3-carboxylate. See J. E. Macor et al., *The 5-HT3-Antaionist Tropisetron (ICS 205-930) is a Potent and Selective A7 Nicotinic Receptor Partial Agonist.* Bioorg. Med. Chem. Lett. 2001, 319-321).

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); Stevens et al., Psychopharmatology, (1998) 136: 320-27; and Shytle et al., Molecular Psychiatry, (2002), 7, pp. 525-535.

Thus, in accordance with the invention, there is provided a method of treating a patient, especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formulas I, II, or III.

Neurodegenerative disorders included within the methods of the present invention include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Sträussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α7nACh receptor agonists, such as the compounds of the present invention can be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. See, e.g., WO 99/62505. Thus, in accordance with the invention, there is provided a method of treating a patient, especially a human, suffering from age-related dementia and other dementias and conditions with memory loss comprising administering to the patient an effective amount of a compound according to Formulas I, II, or III.

Thus, in accordance with a further embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I, II, or III.

Amyloid precursor protein (APP) and Aβ peptides derived therefrom, e.g., $A\beta_{1-40}$, $A\beta_{1-42}$, and other fragments, are known to be involved in the pathology of Alzhemier's disease. The $A\beta_{1-42}$ peptides are not only implicated in neurotoxicity but also are known to inhibit cholinergic transmitter function. Further, it has been determined that Aβ peptides bind to α7nACh receptors. Thus, agents which block the binding of the Aβ peptides to α-7 nAChRs are useful for treating neurodegenerative diseases. See, e.g., WO 99/62505. In addition, stimulation α7nACh receptors can protect neurons against cytotoxicity associated with Aβ peptides. See, e.g., Kihara, T. et al., Ann. Neurol., 1997, 42, 159.

Thus, in accordance with an embodiment of the invention there is provided a method of treating and/or preventing dementia in an Alzheimer's patient which comprises administering to the subject a therapeutically effective amount of a compound according to Formulas I, II, or III to inhibit the binding of an amyloid beta peptide (preferably, $A\beta_{1-42}$) with nACh receptors, preferable α7nACh receptors, most preferably, human α7nACh receptors (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

In addition, nicotinic receptors have been implicated as playing a role in the body's response to alcohol ingestion. Thus, agonists for α7nACh receptors can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formulas I, II, or III.

Agonists for the α7nACh receptor subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formulas I, II, or III.

As noted above, agonists for the α7nACh receptor subtypes can also be used in the treatment of nicotine addiction, inducing smoking cessation, treating pain, and treating jetlag, obesity, diabetes, and inflammation. Thus, in accordance with an embodiment of the invention there is provided a method of treating a patient suffering from nicotine addiction, pain, jetlag, obesity and/or diabetes, or a method of inducing smoking cessation in a patient comprising administering to the patient an effective amount of a compound according to Formulas I, II, or III.

The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds with affinity for the α7nACh receptor on macrophages may be useful for human inflammatory diseases including rheumatoid arthritis, diabetes and sepsis. See, e.g., Czura, C J et al., J. Intern. Med., 2005, 257(2), 156-66.

Thus, in accordance with an embodiment of the invention there is provided a method of treating a patient (e.g., a mammal, such as a human) suffering from an inflammatory disease, such as, but not limited to, rheumatoid arthritis, diabetes or sepsis, comprising administering to the patient an effective amount of a compound according to Formulas I, II, or III.

In addition, due to their affinity to α7nACh receptors, labeled derivatives of the compounds of Formulas I, II, or III (e.g., $C^{11}$ or $F^{18}$ labeled derivatives), can be used in neuroimaging of the receptors within, e.g., the brain. Thus, using such labeled agents in vivo imaging of the receptors can be performed using, e.g., PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) comprising administering to the patient an effective amount of a compound according to Formulas I, II, or III.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention can be administered to patients, e.g., mammals, particularly humans, at typical dosage levels customary for α-7 nicotinic receptor agonists such as the known α-7 nicotinic receptor agonist compounds mentioned above. For example, the compounds can be administered, in single or multiple doses, by oral administration at a dosage level of, for example, 0.0001-10 mg/kg/day, e.g., 0.01-10 mg/kg/day. Unit dosage forms can contain, for example, 1-200 mg of active compound. For intravenous administration, the compounds can be administered in single or multiple dosages.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

Using the following procedures and further procedures described below, the following compounds in Examples 1-191 were prepared.

EXAMPLES

All spectra were recorded at 300 MHz on a Bruker Instruments NMR unless otherwise stated. Coupling constants (J) are in Hertz (Hz) and peaks are listed relative to TMS (δ 0.00 ppm). Microwave reactions were performed using a Personal Chemistry Optimizer™ microwave reactor in 2.5 mL or 5 mL Personal Chemistry microwave reactor vials. All reactions were performed at 200° C. for 600 s with the fixed hold time ON unless otherwise stated. Sulfonic acid ion exchange resins (SCX) were purchased from Varian Technologies. Analytical HPLC was performed on 4.6 mm×100 mm Xterra $RP_{18}$ 3.5μ columns using a gradient of 20/80 to 80/20 water (0.1% formic acid)/acetonitrile (0.1% formic acid) over 6 min. Preparative HPLC was performed on 30 mm×100 mm Xtera Prep $RP_{18}$ 5μ columns using an 8 min gradient of 95/5 to 20/80 water (0.1% formic acid)/acetonitrile (0.1% formic acid). Hydrochloride salts of the bicycle amides were prepared by adding an ethereal solution of hydrochloric acid to a methanolic solution of the bicyclic amide, followed by isolation of the resulting precipitate.

Acid Preparations.

The following procedures (1-9) detail the preparation of the indazole and benzisothiazole acids that were not commercially available.

Procedure 1:

Procedure 1 provides a method for the preparation of 6-nitroindazole-3-acid and the coupling with bicyclobases to form nitro-substituted derivatives.

A 5 mL microwave reaction vessel was charged with 3-iodo-6-nitroindazole (1 mmol), copper (I) cyanide (2 mmol) and N,N-dimethylformamide (3 mL). The vessel was sealed and subjected to microwave irradiation at 185° C. for 600 sec. The reaction mixture was partitioned between ethyl acetate (100 mL) and water (100 mL) and the mixture was filtered through Celite. The organic layer was collected, washed with brine, dried (magnesium sulfate), and concentrated to give 122 mg of a 10/1 mixture of 3-cyano-6-nitroindazole and 6-nitroindazole as a yellow solid. The 10/1 mixture of 3-cyano-6-nitroindazole and 6-nitroindazole was dissolved in 10 N sodium hydroxide and the bright orange solution was heated at 100° C. for 1 h. The mixture was allowed to cool to room temperature and carefully acidified (pH=1) with 3 N hydrochloric acid. The solid was isolated and triturated with EtOAc to provide 51 mg of 6-nitroindazole-3-carboxylic acid as a brown solid. The acid was coupled with the bicyclobase according to procedure A. 3-Iodo-6-nitroindazole was prepared from 6-nitroindazole using the method of Collot, C., et al., *Tetrahedron*, 55, 6917 (1999).

The following acid was prepared using this method:
6-Nitro-1H-indazole-3-carboxylic acid.

Procedure 2:

Procedure 2 provides a method for the nitration of indazole acid and the coupling with bicyclobases to form nitro-substituted derivatives.

Ethyl indazole-3-carboxylate (73.7 mmol) was dissolved in 20 mL concentrated sulfuric acid and the reaction mixture was cooled to 0° C. A mixture of concentrated sulfuric acid (12 mL) and 70% nitric acid (12 mL) was added dropwise over the course of 1 h. The mixture was stirred for an additional 1 h at 0° C. and was poured onto of crushed ice (200 g). The solid was collected by vacuum filtration, washed with several portions of water and dried in vacuo. The dried solid was suspended in 250 mL acetonitrile and the mixture was heated at reflux for 2 h. The mixture was allowed to cool to room temperature and the solid was collected and dried in vacuo to provide ethyl 5-nitroindazole-3-carboxylate (53%) as a colorless solid. The acid, obtained by basic hydrolysis, was coupled with the bicyclobase according to procedure A.

Literature reference: *Org. Synthesis, Coll. Vol.* 1, page 372.

The following acid was prepared using this method:
5-Nitro-1H-indazole-3-carboxylic acid.

Procedure 3:

Procedure 3 provides a method for the preparation of isatins from anilines and the conversion of the isatins to the corresponding indazole-3-carboxylic acids.

A solution of the substituted aniline (565 mL) in 6N hydrochloric acid (106 mL) was added to a suspension of 2,2,2-trichloro-1-ethoxyethanol (678 mL) and sodium sulfate (3.15 mol) in water (1.4 L) and the reaction mixture was stirred vigorously for 1 h. A solution of hydroxylamine hydrochloride (2.08 mol) in water (650 mL) was added in one portion and the reaction mixture was heated at 80° C. for 1.5 h. The reaction mixture was cooled to 10° C. and the precipitated solids were collected by filtration, washed with water, and dried to provide the amide in 91% yield.

The amide was added to sulfuric acid (1.9L) and the reaction mixture was heated at 60° C. for 6 h. The reaction mixture was allowed to cool to room temperature and was cautiously poured onto ice (7 kg). The precipitated solids were collected by filtration, washed with water, and dried to provide the isatin in 61% yield.

The conversion of the substituted isatins to the corresponding indazole-3-carboxylic acids is essentially the same method as described for indazole-3-carboxylic acid: Snyder, H. R., et. al. *J. Am. Chem. Soc.* 1952, 74, 2009. The substituted isatin (22.1 mmol) was diluted with 1 N sodium hydroxide (24 mL) and was heated at 50° C. for 30 min. The burgundy solution was allowed to cool to rt and was maintained for 1 h. The reaction mixture was cooled to 0° C. and was treated with a 0° C. solution of sodium nitrite (22.0 mmol) in water (5.5 mL). This solution was added through a pipet submerged below the surface of a vigorously stirred solution of sulfuric acid (2.3 mL) in water (45 mL) at 0° C. The addition took 15 min and the reaction was maintained for an additional 30 min. A cold (0° C.) solution of tin (II) chloride dihydrate (52.7 mmol) in concentrated hydrochloric acid (20 mL) was added to the reaction mixture over 10 min and the reaction mixture was maintained for 60 min. The precipitated solids were isolated by filtration, washed with water, and dried to give a quantitative mass balance. This material was of sufficient purity ($^1$H NMR and LC/MS) to use in the next step without further purification. Alternatively, the acid was recrystallized from acetic acid to provide pure material.

The following acids were prepared using this method:
5-Fluoro-1H-indazole-3-acid.
5-Bromo-1H-indazole-3-acid.
6-Bromo-1H-indazole-3-acid.
5-Trifluoromethoxy-1H-indazole-3-acid.
5-Methoxy-1H-indazole-3-acid.

Procedure 4:

Procedure 4 provides a preparation of substituted benzisothiazole-3-carboxylic acids from the corresponding thiophenols.

To a solution of 3-methoxythiophenol (26.7 mmol) in ether (20 mL) was added oxalyl chloride (43 mmol) dropwise. The mixture was heated at reflux for 1.5 h, cooled to rt, and concentrated in vacuo. The resulting yellow oil was dissolved in dichloromethane (50 mL), cooled to 0° C., and was treated with aluminum chloride (32.0 mmol) in portions. The mixture was heated at reflux for 30 min, cooled to rt, and poured onto ice water with stirring. The organic layer was separated and successively washed with saturated, aqueous sodium bicarbonate, water, and brine. The organic layer was dried over magnesium sulfate, filtered and concentrated in vacuo. The residue was purified by chromatography (4/1 ethyl acetate/hexane), thus providing 6-methoxy-1-benzothiophene-2,3-dione in 47% yield as an orange solid.

To a mixture of the dione (0.44 mmol) in 30% aqueous solution of ammonium hydroxide (2.0 mL) was added 35% aqueous solution hydrogen peroxide (0.2 mL) and the reaction mixture was maintained for 12 h. The precipitated pink solids were isolated by filtration, washed with water, and dried under high vacuum, thus providing the amide in 42% yield.

To a solution of the amide (5.46 mmol) in methanol (100 mL) was added 10 N sodium hydroxide (12 mL). The mixture was heated at reflux for 12 h, cooled to rt, and was acidified to pH<2 by the slow addition of conc. hydrochloric acid. The organic layer was extracted with dichloromethane (2×) and was dried over sodium sulfate. The crude product was purified by chromatography (300/50/1 dichloromethane/methanol/formic acid), thus providing the acid in 89% as a pink solid.

The following acids were prepared by this method:
Benzisothiazole-3-carboxylic acid.
6-Bromobenzisothiazole-3-carboxylic acid.
5-Bromobenzisothiazole-3-carboxylic acid.
6-Methoxybenzisothiazole-3-carboxylic acid
7-Methoxybenzisothiazole-3-carboxylic acid.
6-Ethoxybenzisothiazole-3-acid.

Procedure 5:

Procedure 5 provides a method for the coupling between brominated benzisothiazole-3-carboxylic esters and brominated indazole-3-carboxylic esters and Grignard reagents to form alkyl- and heterocycle-substituted acids.

A 0.5 M solution of the Grignard reagent (25.0 mmol, 3.7 eq) in tetrahydrofuran was diluted with tetrahydrofuran (60 mL) and treated with a 0.5 M solution of zinc chloride (25.0 mmol, 3.7 eq) in tetrahydrofuran at rt. After 10 min, the brominated ethyl benzisothiazole-3-carboxylate (0.30 mmol) and bis(triphenylphosphine)palladium (II) chloride (0.95 mmol, 0.1 eq) were added to the suspension. The reaction mixture was maintained for 1 h at ambient temperature then at 65° C. for 1 h. The reaction was quenched with saturated ammonium chloride and was extracted with dichloromethane (3×). The extracts were dried over sodium sulfate and concentrated to dryness. The residue was purified by chromatography using a gradient of 100/0 to 90/10 dichloromethane/methanol to provide the cyclopropyl-substituted amide. The amide was dissolved in a mixture of methanol/tetrahydrofuran/water (90/10/20 mL) and was treated with sodium hydroxide (5.8 g). The mixture was heated at reflux for 12 h, cooled to rt, filtered, and was acidified to pH<2 by the slow addition of conc. hydrochloric acid. The aqueous layer was extracted with ethyl acetate (2×) and was dried over sodium sulfate. Concentration of the extracts gave the acid in 38% yield. The acid was coupled to the bicyclobases according to procedure A.

This procedure was used, with slight modifications, to derivatize brominated indazole-3-carboxylic esters and carboxamides with various Grignard reagents. The Grignard reagent of thiazole is commercially available. Alternatively, the aryllithium and the corresponding arylzinc reagent can be generated according to the procedure outlined by Reeder, M. R.; et. al. *Org. Proc. Res. Devel.* 2003, 7, 696. The zinc reagents of oxazole, 4-methylthiazole, and 5-methylthiazole were prepared according to this procedure.

The following acids were prepared using this method:
6-(1,3-Thiazol-2-yl)-1H-indazole-3-carboxylic acid.
5-(1,3-Thiazol-2-yl)-1H-indazole-3-carboxylic acid.
5-(4-Methyl-1,3-thiazol-2-yl)-1H-indazole-3-carboxylic acid.
5-(5-Methyl-1,3-thiazol-2-yl)-1H-indazole-3-carboxylic acid.
6-(4-Methyl-1,3-thiazol-2-yl)-1H-indazole-3-carboxylic acid.
6-(5-Methyl-1,3-thiazol-2-yl)-1H-indazole-3-carboxylic acid.
5-(1,3-Oxazol-2-yl)-1H-indazole-3-carboxylic acid.
6-(1,3-Oxazol-2-yl)-1H-indazole-3-carboxylic acid.

Procedure 6:

Procedure 6 details the preparation of benzisoxazole-3-carboxylic acid from 2,5-dibromonitrobenzene.

Diethyl malonate (12.6 g, 79 mmol) was added to a suspension of sodium hydride (3.16 g, 132 mmol) in dimethylsulfoxide (60 ml) over 30 min. The temperature of the reaction rose to 60° C. and the mixture clarified. 1,4-Dibromo-2-nitrobenzene (10 g, 36.0 mmol) was added and the solution was maintained for 2 h at 100° C. The reaction mixture was allowed to cool to rt and was poured into ice (300 g-400 g). The precipitated solids were isolated by filtration and dried to provide 11.0 g of the product (89%).

The ester (11.0 g, 32.0 mmol) was diluted with a 2 N solution of sodium hydroxide (32 mL, 63 mmol) and the reaction mixture was maintained at room temperature for 16 h. The aqueous layer was extracted with dichloromethane (20 mL) and was acidified. The precipitated solids were isolated by filtration and dried to provide 7.00 g of the acid (89%).

Sulfuric acid (1 mL) was added to a solution of the acid (7.00 g, 27.0 mmol) in ethanol (60 ml). The reaction mixture was warmed to reflux, maintained for 2 h, and was concentrated under reduce pressure. The residue was partitioned between ethyl acetate (250 mL) and saturated sodium carbonate (50 mL) and the organic layer was washed with saturated sodium carbonate (50 mL) and brine (50 mL). The organic layer was dried (sodium sulfate) and concentrated to provide 8.00 g (98%) of the ester as a liquid.

Isoamylnitrite (225 mL) was added to a solution of the ester (420 g, 1.46 mol) in ethanol (3 L) in a 10 L three-necked round bottom flask and the mixture was warmed to 60° C. A solution of sodium ethoxide, prepared from sodium metal (33.5 g, 1.46 mmol) in ethanol (1 L) was added dropwise and the reaction mixture was maintained for 2 h. The reaction mixture was allowed to cool to rt and was neutralized with 2 N hydrochloric acid. The reaction mixture was extracted with ethyl acetate (4×2 L) and the combined organic layers were washed with water (2×1 L) and brine (2×1 L) and dried (sodium sulfate). The residue was purified by chromatography (1/1 to 0/1 hexane/ethyl acetate) to provide 110 g of the product (28%).

10% Palladium on carbon (1.5 g) and triethylamine (7.5 g, 82.4 mmol) were added to a solution of ethyl 6-bromobenzisoxazole-3-carboxylate (20 g, 0.081 mol) in ethanol (300ml) at 0° C. under an atmosphere of nitrogen. The nitrogen atmosphere was removed by evacuation and replaced with hydrogen gas, and the reaction mixture was maintained for 1 hour. The hydrogen atmosphere was removed by evacuation and replaced with nitrogen gas, and the palladium removed by filtration through Celite. The filter cake was washed with ethanol (3×50 mL) and the filtrates were concentrated. The residue was dissolved in dichloromethane (200 mL) and the solution was washed with water (4×50 mL), dried (sodium sulfate) and evaporated to provide 13.0 g of the product as a yellow solid (96%). The ester was saponified using sodium hydroxide to provide the acid. The acid was coupled with the bicyclobase according to procedure A.

Literature reference: Angell, R. M.; Baldwin, I. R.; Bamborough, P.; Deboeck, N. M.; Longstaff, T.; Swanson, S. WO 04/010995 A1

The following acid was prepared using this method:
1,2-Benzisoxazole-3-carboxylic acid.

Procedure 7:

Procedure 7 provides a method for the preparation of 5-difluoromethoxyindazole-3-acid from 3-bromo-4-nitrophenol.

3-Bromo-4-nitrophenol (10.0 mmol) was added to a suspension of sodium hydroxide (29.0 mmol) in N,N-dimethylformamide (15 mL) and the suspension was maintained for 15 min at rt. The reaction mixture was cooled to 0° C. and was treated with ethyl chlorodifluoroacetate (20.0 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 75% yield as a yellow oil.

Diethyl malonate (328 mmol) was added dropwise to a suspension of sodium hydride (328 mmol) in dimethylsulfoxide (40 mL) at 0° C. The reaction mixture was warmed to 60° C. and maintained for 0.5 h. A solution of the difluoromethyl ether (149 mmol) in dimethylsulfoxide (80 mL) was added dropwise and the reaction mixture was heated at 100° C. for 5 h. The cooled solution was poured onto ice water, and the aqueous layer was extracted with dichloromethane (3×100 mL). The combined organic layers were dried (magnesium sulfate) and concentrated to give the crude diester in 112% yield as an oil. The diester (167 mmol), sodium hydroxide (500 mmol), and water (335 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 5° C. and the solids were collected by filtration and dried to provide the acid in 61% yield.

Acetyl chloride (203 mmol) was added dropwise to ethanol (300 mL) at 0° C. After 0.5 h, the acid (101 mmol) was added and the reaction mixture was heated at reflux for 15 h. The reaction mixture was concentrated and the residue was partitioned between dichloromethane (200 mL) and saturated sodium bicarbonate (100 mL). The aqueous layer was further extracted with dichloromethane (2×200 mL) and the combined organic layers were dried (magnesium sulfate) and concentrated to provide the ester in 60% yield as a brown oil.

The ester (60.4 mmol) was dissolved in ethanol (103 mL), diluted with water (71 mL), and was treated with ammonium chloride (243 mmol) and iron powder (301 mmol). The reaction mixture was heated at reflux for 10 minutes and the suspension was filtrated through Celite and the filter cake was washed with ethanol three times. The filtrate was concentrated, the residue was suspended in 2 N hydrochloric acid and was stirred vigorously for 0.5 h. The aqueous layer was washed with ethyl acetate (3×50 mL) and the pH adjusted to 9-10 with 5 M sodium hydroxide. The aqueous layer was extracted with chloroform (3×100 mL) and the combined organic layers were dried (magnesium sulfate). Acetic anhydride (392 mmol), isoamyl nitrite (291 mmol), and potassium acetate (51.0 mmol) were added to the organic layer and the suspension was heated at reflux for 16 h. The solution was evaporated and the residue was partitioned between saturated sodium bicarbonate (50 mL) and dichloromethane (100 mL). The aqueous layer was further extracted with dichloromethane (2×100 mL) and the combined organic layers were dried (magnesium sulfate) and concentrated to provide the N-acetylindazole ester in 79% yield as a brown oil.

The ester (63.8 mmol), sodium hydroxide (193 mmol), and water (65 mL) were combined and the reaction was maintained for 24 h at 60° C. After cooling to rt, the aqueous layer was washed with dichloromethane (3×50 mL). The aqueous layer was adjusted to pH 1 with concentrated hydrochloric acid. The precipitated solids were collected by filtration, washed with water and dichloromethane, and dried to provide the acid in 27% yield.

The following acid was prepared according to this method: 5-(Difluoromethoxy)-1H-indazole-3-carboxylic acid.

Procedure 8:

Procedure 8 provides a method for the preparation of 6-difluoromethoxyindazole-3-acid from 4-nitrophenol.

4-Nitrophenol (162 mmol) was added to a suspension of sodium hydroxide (485 mmol) in N,N-dimethylformamide (150 mL) and the suspension was maintained for 15 min at rt. The reaction mixture was cooled to 0° C. and was treated with ethyl chlorodifluoroacetate (329 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 59% yield as a yellow oil.

The nitro ether (149 mmol) was dissolved in ethanol (37.5 mL), diluted with water (25 mL), and was treated with ammonium chloride (84.7 mmol) and iron powder (105 mmol). The reaction mixture was heated at reflux for 30 minutes and the suspension was filtered through Celite. The filter cake was washed with ethanol three times and the combined filtrates were concentrated. The residue was dissolved in water and the pH adjusted to 9-10 with 5 M sodium hydroxide. The aqueous layer was extracted with ethyl acetate (3×100 mL) and the combined organic layers were dried (magnesium sulfate) and concentrated to a yellow oil. The oil was dissolved in acetic anhydride (23.5 mmol) and the reaction mixture was maintained at rt for 16 h. The reaction mixture was diluted with water (50 mL) and was neutralized with solid sodium bicarbonate. The precipitated solids were isolated by filtration, washed with water, and dried to provide the acetamide in 62% yield as a light yellow solid.

Acetic anhydride (19.6 mmol) was added to a solution of the acetamide (13.2 mmol) in chloroform (20 mL) and the reaction mixture was warmed to reflux. Fuming nitric acid (16.0 mmol) was added dropwise and the reaction mixture was maintained at reflux for 30 min. The cooled solution was diluted with water (20 mL) and the aqueous layer was extracted with dichloromethane (3×10 mL). The combined organic layers were dried (magnesium sulfate) and concentrated to provide the nitro-amide in 83% yield.

The amide (11.0 mmol), sodium hydroxide (43.8 mmol), and water (10 mL) were combined and the reaction mixture was maintained for 1.5 hour at 60° C. the reaction was allowed to cool to rt and the precipitated solids were isolated by filtration, and washed with water, and dried to provide the aniline in 98% yield as a light yellow solid. The aniline (15.7 mmol) was mixed with 40% hydrobromic acid (14.3 g) and water (10 mL) and the reaction mixture was warmed to 80-90° C. in order to completely dissolve the aniline. The reaction mixture was cooled to 0° C. and a solution of sodium nitrite (23.2 mmol) in water (5.3 mL) was added during a 15 min period. The solution was maintained for 40 minutes at 0-5° C. and filtered. Copper (I) bromide (18.8 mmol) was dissolved in 40% hydrobromic acid (21 mL) and was cooled to 0° C. The solution of the diazo salt was added slowly to the copper solution and the mixture was maintained for 30 min at 0-10° C. The reaction mixture was heated at 60° C. for 30 min and then at 100° C. for 10 min to ensure completion. The reaction mixture was allowed to cool to rt and was extracted with dichloromethane (3×40 mL). The combined organic layers were washed with 1 M sodium hydroxide, water, 1 N hydrochloric acid, and water. The organic layer was dried (magnesium sulfate) and concentrated to provide the nitro bromide in 76% yield as a light yellow solid.

Diethyl malonate (25.7 mmol) was added dropwise to a suspension of sodium hydride (25.8 mmol) in dimethylsulfoxide (5 mL) at 0° C. The reaction mixture was warmed to 60° C. and maintained for 30 min. A solution of the nitro bromide (11.7 mmol) in dimethylsulfoxide (7 mL) was added dropwise and the reaction mixture was heated at 100° C. for 5 h. The cooled solution was poured onto ice water and the aqueous layer was extracted with dichloromethane (3×100 mL). The combined organic layers were dried (magnesium sulfate) and concentrated to give the crude diester as an oil. The diester (11.7 mmol), sodium hydroxide (35 mmol), and water (20 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 0° C. and the solids were collected by filtration and dried to provide the acid in 64% yield.

Acetyl chloride (15.3 mmol) was added dropwise to ethanol (50 mL) at 0° C. After 30 min, the acid (7.69 mmol) was added and the reaction mixture was heated at reflux for 15 h. The reaction mixture was concentrated and the residue was partitioned between dichloromethane (20 mL) and saturated sodium bicarbonate (10 mL). The aqueous layer was further extracted with dichloromethane (2×20 mL) and the combined organic layers were dried (magnesium sulfate) and concentrated to provide the ester in 94% yield as a brown oil.

Acetic anhydride (6.0 mL) was added to a suspension of the ester (3.64 mmol), and acetic acid (7.0 mL) at 0° C. Zinc dust (14.6 mmol) was added in portions over 15 min and the reaction mixture was maintained for 30 min at 0° C. and then for 1.5 h at rt. Additional zinc powder (6.15 mmol) was added and the reaction maintained for 3 h. The suspension was filtered through Celite and the filtrate was concentrated. The residue was partitioned between saturated sodium bicarbonate (10 mL) and ethyl acetate (20 mL). The aqueous layer was further extracted with ethyl acetate (3×20 mL) and the combined organic layers were dried (magnesium sulfate) and concentrated to provide the acetamide in 92% yield as a brown oil.

Acetic anhydride (13.7 mmol), isoamyl nitrite (13.7 mmol), and potassium acetate (2.04 mmol) were added to a solution of the acetamide (3.92 mmol) in chloroform (20 mL) and the suspension was heated at reflux for 16 h. The solution was evaporated and the residue was partitioned between saturated sodium bicarbonate (10 mL) and dichloromethane (20 mL). The aqueous layer was further extracted with dichloromethane (2×20 mL) and the combined organic layers were dried (magnesium sulfate) and concentrated to provide the crude N-acetylindazole ester as a brown oil.

The ester (3.36 mmol), sodium hydroxide (10 mmol) and water (5 mL) were combined and the reaction was maintained for 24 h at 60° C. After cooling to rt, the aqueous layer was washed with dichloromethane (3×30mL). The aqueous layer was adjusted to pH 1 with concentrated hydrochloric acid and the precipitated solids were collected by filtration, washed with water and dichloromethane, and dried to provide the acid in 26% yield.

The following acid was prepared according to this method:
6-(Difluoromethoxy)-1H-indazole-3-carboxylic acid.

Procedure 9:

Procedure 9 provides a method for the trapping of indazole aryllithiums with ketones and the coupling with 3-aminoquinuclidine to form heterocyclic derivatives.

tert-Butyl 6-bromoindazole-3-carboxylate was prepared from the acid by reaction with a 2-fold excess of di-tert-butyldicarbonate followed by treatment with sodium hydroxide. To a suspension of sodium hydride (60% mineral oil dispersion) (4.8 mmol) in tetrahydrofuran (40 mL) at 0° C. was slowly added a solution of tert-butyl 6-bromoindazole-3-carboxylate (4.0 mmol) in tetrahydrofuran (4 mL). After stirring for 0.5 h at 0° C., the mixture was cooled to −78° C. and a 1.7 M solution of tert-butyllithium in pentane (5.1 mmol) was added. After 0.5 h at −78° C, a solution of tetrahydropyran-4-one (5 mmol) in tetrahydrofuran (1 mL) was added dropwise. The mixture was stirred at −78° C. for 1 h and warmed to 0° C. The reaction mixture was quenched with saturated aqueous ammonium chloride and the mixture was partitioned between ethyl acetate (100 mL) and water (100 mL). The organic layer was separated, washed with brine (50 mL), dried (magnesium sulfate), and concentrated. The residue was purified by chromatography (70/30 ethyl acetate/hexanes) to yield 6-(4-hydroxytetrahydropyran-4-yl)-1H-indazole-3-carboxylic acid tert-butyl ester (68%) as a colorless solid.

6-(4-Hydroxytetrahydropyran-4-yl)-1H-indazole-3-carboxylic acid tert-butyl ester (0.86 mmol) was dissloved in trifluoroacetic acid (3 mL) and the mixture was maintained at room temperature for 16 h. The solvent was removed in vacuo and the residue was triturated with ethyl acetate to provide 6-(3,6-dihydro-2H-pyran-4-yl)-1H-indazole-3-carboxylic acid (76%). The acids were coupled with the bicyclobase according to procedure A.

The following acids were prepared using this method:
5-(3,6-Dihydro-2H-pyran-4-yl)-1H-indazole-3-carboxylic acid.
6-(3,6-Dihydro-2H-pyran-4-yl)-1H-indazole-3-carboxylic acid.

Representative Procedure A.

Procedure A provides a method for the coupling between bicyclobases and carboxylic acids to form carboxamide derivatives.

Example 1

N-(8-Methyl-8-azabicyclo[3.2.1]oct-3-yl)-1,2-benzisothiazole-3-carboxamide

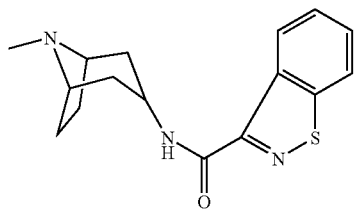

To a solution of benzisothiazole-3-carboxylic acid (0.93 mmol) in tetrahydrofuran (10 mL) and N,N-dimethylformamide (1 mL) was added N,N-diisopropylethylamine (2.87 mmol) and 8-methyl-8-azabicyclo[3.2.1]octan-3-amine dihydrochloride (0.99 mmol).

The reaction mixture was maintained at room temperature for 30 min under nitrogen and then HATU (1.00 mmol) was added. After 18 h, the reaction mixture was partitioned between saturated aqueous potassium carbonate solution and 95/5 dichloromethane/methanol. The aqueous layer was extracted with 95/5 dichloromethane/methanol (2×), and the combined organic layers were washed with brine, dried over sodium sulfate, filtered and concentrated in vacuo. The residue was purified by silica gel flash column chromatography using a mixture of [90/10/1 dichloromethane/methanol/ammonium hydroxide] as the eluent, thus providing the product in 20% yield. Alternatively, the residues were purified by preparative HPLC. $^1$H NMR (CD$_3$OD) δ 8.79 (dd, J=8.3, 1.0, 1H), 8.10-8.06 (m, 1H), 7.63-7.49 (m, 2 H), 4.39-4.32 (m, 0.5 H), 4.17-4.15(m, 0.5 H), 3.33-3.27 (m, 2 H), 2.35 (s, 1.5 H), 2.34 (s, 1.5 H), 2.31-1.75 (m, 8 H); LC/MS (EI) $t_R$ 3.76 min, m/z 302 (M$^+$+1).

Using this general procedure the following compounds were prepared:

Example 2

2-(1H-Indazol-3-ylcarbonyl)octahydro-2H-pyrido[1,2-a]pyrazine hydroformate

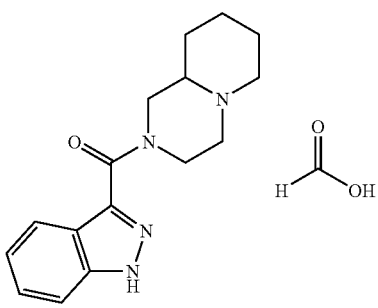

Prepared by Procedure A in 40% yield. LC/MS (EI) $t_R$ 3.2 min, m/z 285 (M$^+$+1).

Example 3

3-(Hexahydropyrrolo[1,2-a]pyrazin-2(1H)-ylcarbonyl)-1H-indazole hydroformate

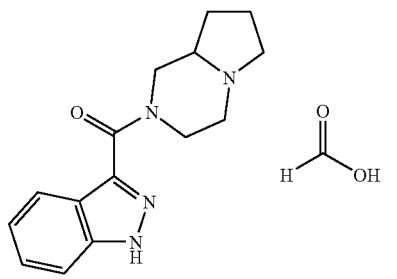

Prepared by Procedure A in 17% yield. LC/MS (EI) $t_R$ 2.60 min, m/z 271 (M$^+$+1).

Example 4

3-(Hexahydropyrrolo[1,2-a]pyrazin-2(1H)-ylcarbonyl)-6-methoxy-1H-indazole hydroformate

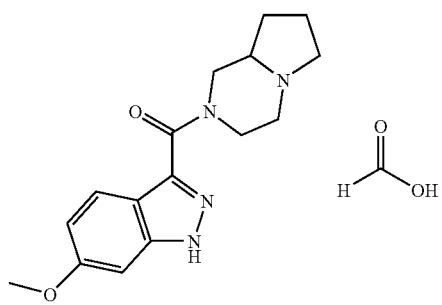

Prepared by Procedure A in 45% yield. LC/MS (EI) $t_R$ 3.1 min, m/z 301 (M$^+$+1).

Example 5

3-[(3-Methyl-3,8-diazabicyclo[3.2.1]oct-8-yl)carbonyl]-1H-indazole hydroformate

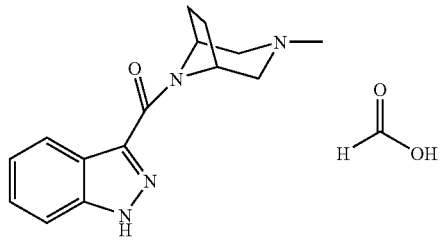

Prepared by Procedure A in 45% yield. LC/MS (EI) $t_R$ 2.60 min, m/z 271 (M$^+$+1).

Example 6

3-[(8-Methyl-3,8-diazabicyclo[3.2.1]oct-3-yl)carbonyl]-1H-indazole hydroformate

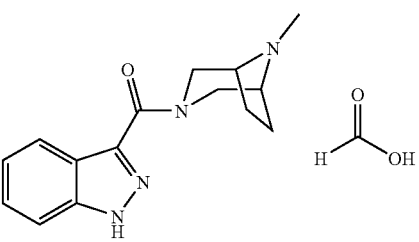

Prepared by Procedure A in 60% yield. LC/MS (EI) $t_R$ 2.60 min, m/z 271 (M$^+$+1).

Example 7

3-[(8-Methyl-3,8-diazabicyclo[3.2.1]oct-3-yl)carbonyl]-5-(trifluoromethoxy)-1H-indazole hydroformate

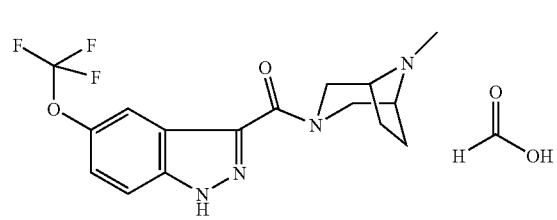

Prepared by Procedure A in 65% yield. LC/MS (EI) $t_R$ 4.90 min, m/z 355 (M$^+$+1).

Example 8

5-(3,6-Dihydro-2H-pyran-4-yl)-N-(8-methyl-8-azabicyclo[3.2.1]oct-3-yl)-1H-indazole-3-carboxamide hydroformate

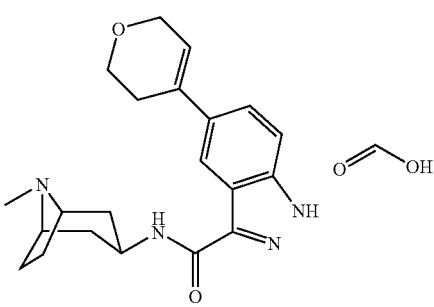

Prepared by Procedure A in 9% yield. LC/MS (EI) $t_R$ 3.44 min, m/z 367 (M$^+$+1).

Example 9

5-(3,6-Dihydro-2H-pyran-4-yl)-N-(endo-9-methyl-9-azabicyclo[3.3.1]non-3-yl)-1H-indazole-3-carboxamide hydroformate

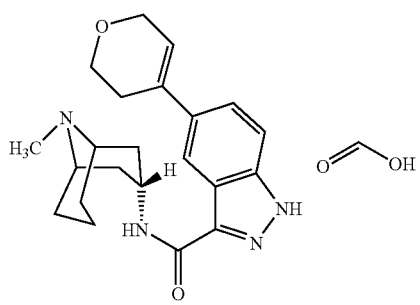

Prepared by Procedure A in 21% yield. LC/MS (EI) $t_R$ 4.71 min, m/z 381 (M$^+$+1).

Example 10

5-Bromo-N-(8-methyl-8-azabicyclo[3.2.1]oct-3-yl)-1H-indazole-3-carboxamide

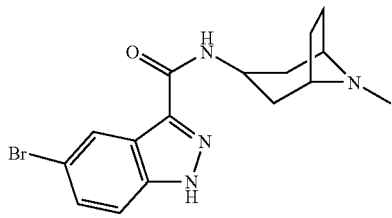

Prepared by Procedure A in 29% yield. LC/MS (EI) $t_R$ 5.40 min, m/z 363/365 (M$^+$/M$^+$+2).

Example 11

5-Fluoro-N-(8-methyl-8-azabicyclo[3.2.1]oct-3-yl)-1H-indazole-3-carboxamide hydroformate

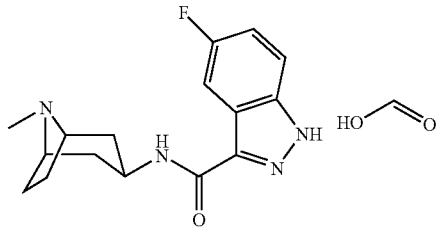

Prepared by Procedure A in 45% yield. LC/MS (EI) $t_R$ 3.03 min, m/z 303 (M$^+$+1).

Example 12

5-Methoxy-3-[(8-methyl-3,8-diazabicyclo[3.2.1]oct-3-yl)carbonyl]-1H-indazole hydroformate

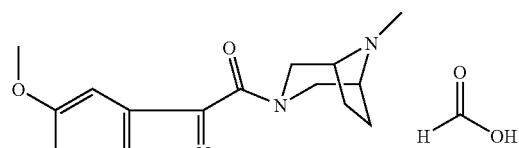

Prepared by Procedure A in 60% yield. LC/MS (EI) $t_R$ 2.60 min, m/z 301 (M$^+$+1).

Example 13

5-Methoxy-N-(8-methyl-8-azabicyclo[3.2.1]oct-3-yl)-1H-indazole-3-carboxamide hydroformate

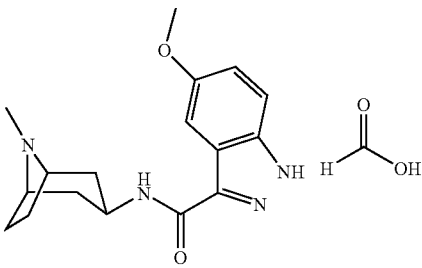

Prepared by Procedure A in 69% yield. LC/MS (EI) $t_R$ 2.85 min, m/z 315.

Example 14

5-Methoxy-N-(8-methyl-8-azabicyclo[3.2.1]oct-3-yl)-1H-indazole-3-carboxamide

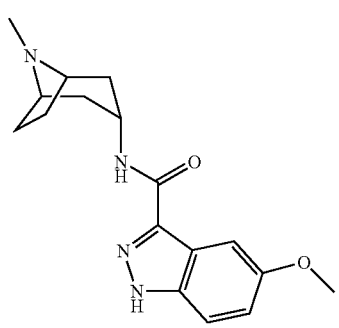

Prepared by Procedure A in 33% yield. LC/MS (EI) $t_R$ 2.47 min, m/z 315 (M$^+$+1).

Example 15

5-Methoxy-N-(exo-8-methyl-8-azabicyclo[3.2.1]oct-3-yl)-1H-indazole-3-carboxamide hydroformate

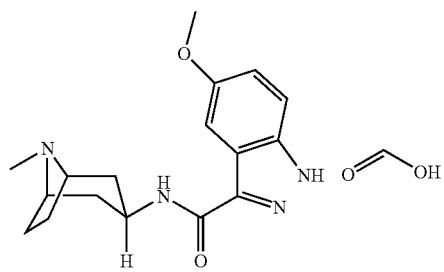

Prepared by Procedure A in 21% yield. LC/MS (EI) $t_R$ 2.12 min, m/z 315 (M$^+$+1).

Example 16

5-Methoxy-N-methyl-N-(8-methyl-8-azabicyclo[3.2.1]oct-3-yl)-1H-indazole-3-carboxamide hydroformate

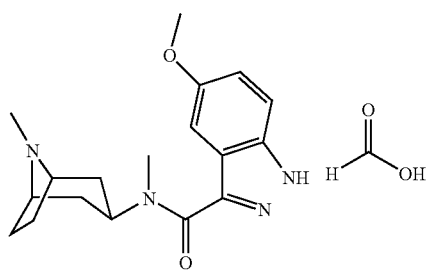

Prepared by Procedure A in 6% yield. LC/MS (EI) $t_R$ 2.55 min, m/z 329 (M$^+$+1).

Example 17

5-Methoxy-N-methyl-N-(endo-8-methyl-8-azabicyclo[3.2.1]oct-3-yl)-1H-indazole-3-carboxamide hydroformate

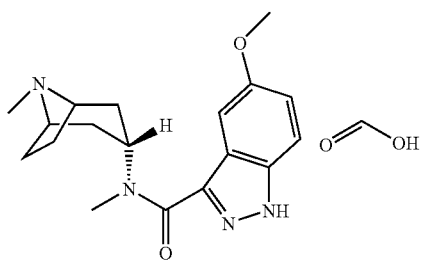

Prepared by Procedure A in 33% yield. LC/MS (EI) $t_R$ 2.47 min, m/z 315 (M$^+$+1).

Example 18

6-(3,6-Dihydro-2H-pyran-4-yl)-N-(8-methyl-8-azabicyclo[3.2.1]oct-3-yl)-1H-indazole-3-carboxamide hydroformate

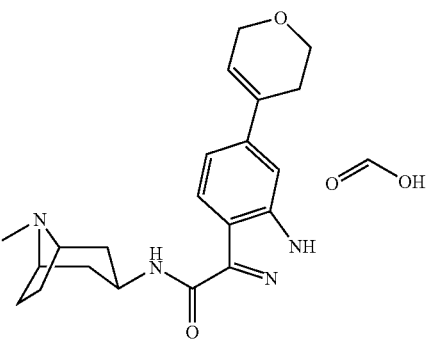

Prepared by Procedure A in 9% yield. LC/MS (EI) $t_R$ 4.34 min, m/z 367 (M$^+$+1).

Example 19

6-Bromo-N-(8-methyl-8-azabicyclo[3.2.1]oct-3-yl)-1H-indazole-3-carboxamide

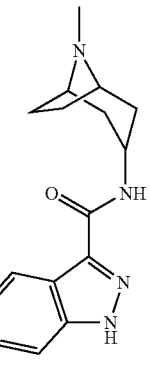

Prepared by Procedure A in 20% yield. LC/MS (EI) $t_R$ 4.28 min, m/z 363/365 (M$^+$/M$^+$+2).

Example 20

6-Bromo-N-(endo-9-methyl-9-azabicyclo[3.3.1]non-3-yl)-1H-indazole-3-carboxamide

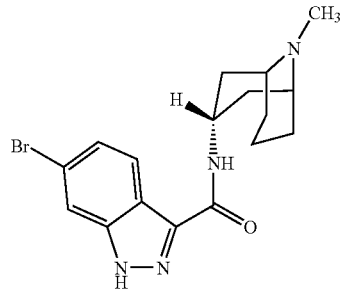

Prepared by Procedure A in 12% yield. LC/MS (EI) $t_R$ 2.26 min, m/z 377 (M$^+$).

Example 21

6-Bromo-N-(endo-9-methyl-9-azabicyclo[3.3.1]non-3-yl)-1H-indazole-3-carboxamide hydroformate

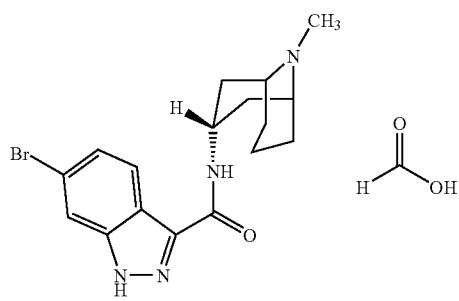

Prepared by Procedure A in 12% yield. LC/MS (EI) $t_R$ 2.37 min, m/z 377/379 (M$^+$+1).

Example 22

6-Ethoxy-N-(8-methyl-8-azabicyclo[3.2.1]oct-3-yl)-1,2-benzisothiazole-3-carboxamide hydroformate

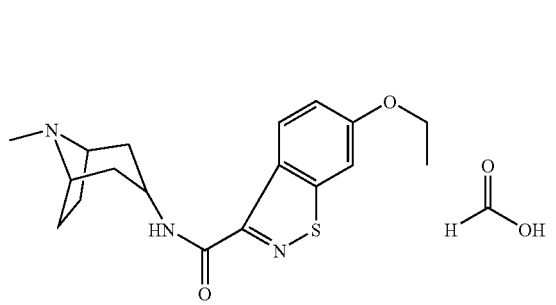

Prepared by Procedure A in 16% yield. LC/MS (EI) $t_R$ 3.96 min, m/z 346 (M$^+$+1).

Example 23

6-Methoxy-3-[(8-methyl-3,8-diazabicyclo[3.2.1]oct-3-yl)carbonyl]-1,2-benzisothiazole hydroformate

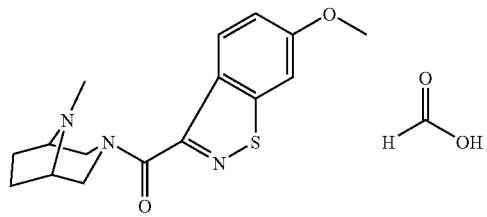

Prepared by Procedure A in 22% yield. LC/MS (EI) $t_R$ 1.69 min, m/z 318 (M$^+$+1).

Example 24

6-Methoxy-3-[(8-methyl-3,8-diazabicyclo[3.2.1]oct-3-yl)carbonyl]-1H-indazole hydroformate

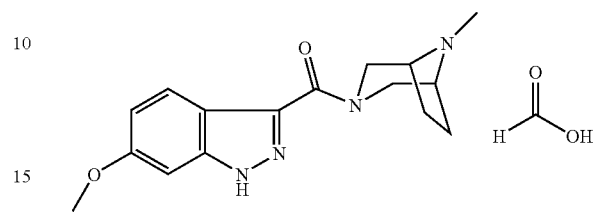

Prepared by Procedure A in 55% yield. LC/MS (EI) $t_R$ 2.40 min, m/z 301 (M$^+$+1).

Example 25

6-Methoxy-N-(2-methyl-2-azabicyclo[2.2.2]oct-5-yl)-1,2-benzisothiazole-3-carboxamide

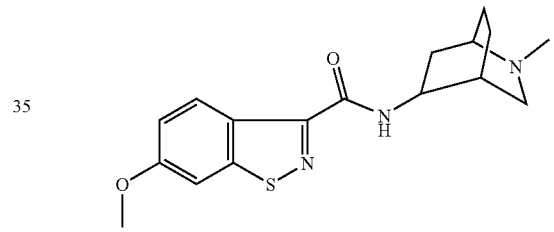

Prepared by Procedure A in 33% yield. LC/MS (EI) $t_R$ 4.10 min, m/z 332 (M$^+$+1).

Example 26

6-Methoxy-N-(8-methyl-8-azabicyclo[3.2.1]oct-3-yl)-1,2-benzisothiazole-3-carboxamide hydrochloride

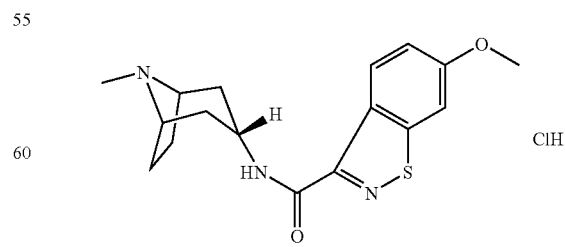

Prepared by Procedure A in 66% yield. LC/MS (EI) $t_R$ 2.56 min, m/z 332 (M$^+$+1).

Example 27

6-Methoxy-N-(8-methyl-8-azabicyclo[3.2.1]oct-3-yl)-1,2-benzisothiazole-3-carboxamide

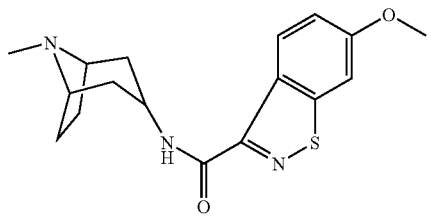

Prepared by Procedure A in 61% yield. LC/MS (EI) $t_R$ 4.96 min, m/z 332 (M$^+$+1).

Example 28

6-Methoxy-N-(8-methyl-8-azabicyclo[3.2.1]oct-3-yl)-1H-indazole-3-carboxamide hydroformate

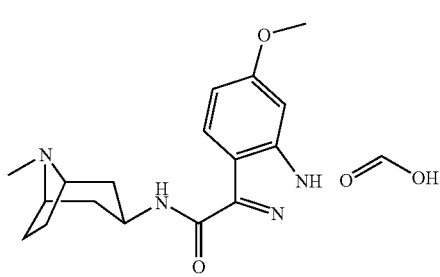

Prepared by Procedure A in 38% yield. LC/MS (EI) $t_R$ 2.52 min, m/z 315 (M$^+$+1).

Example 29

6-Methoxy-N-(endo-9-methyl-9-azabicyclo[3.3.1]non-3-yl)-1,2-benzisothiazole-3-carboxamide

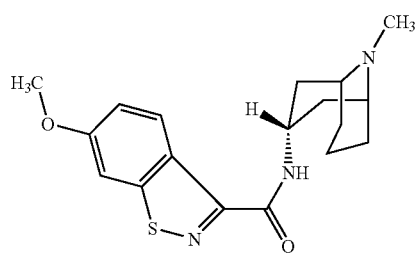

Prepared by Procedure A in 58% yield. LC/MS (EI) $t_R$ 4.09 min, m/z 346 (M$^+$+1).

Example 30

6-Methoxy-N-(endo-9-methyl-9-azabicyclo[3.3.1]non-3-yl)-1H-indazole-3-carboxamide hydroformate

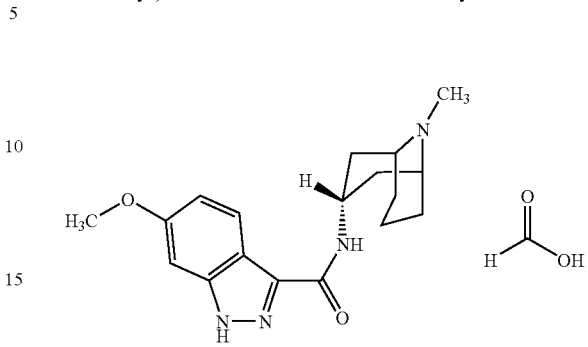

Prepared by Procedure A in 45% yield. LC/MS (EI) $t_R$ 2.68 min, m/z 329 (M$^+$+1).

Example 31

6-Methoxy-N-(endo-9-methyl-9-azabicyclo[3.3.1]non-3-yl)-1H-indazole-3-carboxamide

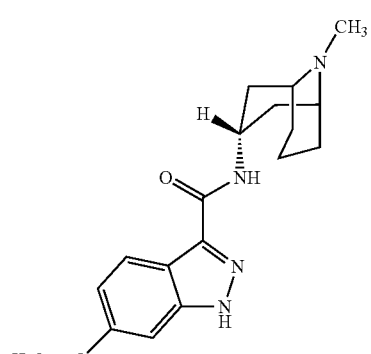

Prepared by Procedure A in 45% yield. LC/MS (EI) $t_R$ 2.68 min, m/z 329 (M$^+$+1).

Example 32

6-Methoxy-N-(endo-8-methyl-8-azabicyclo[3.2.1]oct-3-yl)-1,2-benzisothiazole-3-carboxamide hydrochloride

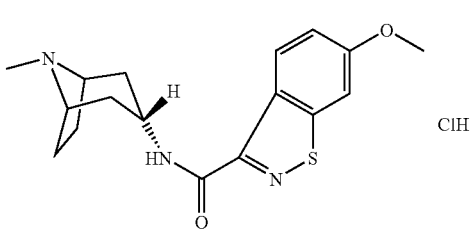

Prepared by Procedure A in 66% yield. LC/MS (EI) $t_R$ 2.56 min, m/z 332 (M$^+$+1).

Example 33

6-Methoxy-N-(endo-8-methyl-8-azabicyclo[3.2.1]oct-3-yl)-1H-indazole-3-carboxamide hydroformate

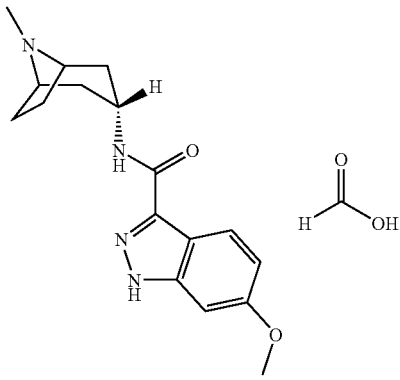

Prepared by Procedure A in 41% yield. LC/MS (EI) $t_R$ 2.51 min, m/z 315 (M$^+$+1).

Example 34

6-Methoxy-N-(endo-8-methyl-8-azabicyclo[3.2.1]oct-3-yl)-1H-indazole-3-carboxamide

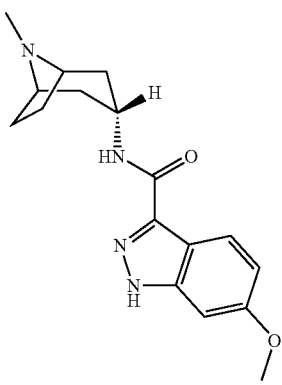

Prepared by Procedure A in 38% yield. LC/MS (EI) $t_R$ 2.52 min, m/z 315 (M$^+$+1).

Example 35

6-Methoxy-N-(exo-8-methyl-8-azabicyclo[3.2.1]oct-3-yl)-1H-indazole-3-carboxamide hydroformate

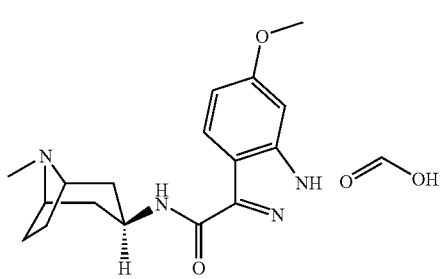

Prepared by Procedure A in 36% yield. LC/MS (EI) $t_R$ 2.57 min, m/z 315 (M$^+$+1).

Example 36

7-Methoxy-N-(8-methyl-8-azabicyclo[3.2.1]oct-3-yl)-1,2-benzisothiazole-3-carboxamide hydroformate

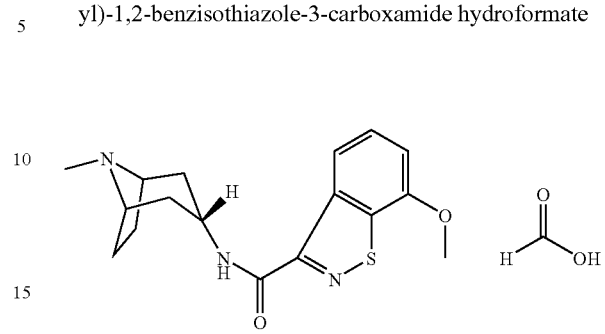

Prepared by Procedure A in 5% yield. LC/MS (EI) $t_R$ 3.96 min, m/z 332 (M$^+$+1).

Example 37

7-Methoxy-N-(8-methyl-8-azabicyclo[3.2.1]oct-3-yl)-1,2-benzisothiazole-3-carboxamide

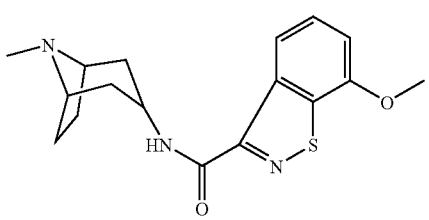

Prepared by Procedure A in 3% yield. LC/MS (EI) $t_R$ 3.81 min, m/z 332 (M$^+$+1).

Example 38

5-Methoxy-N-(endo-9-methyl-9-azabicyclo[3.3.1]non-3-yl)-1H-indazole-3-carboxamide hydroformate

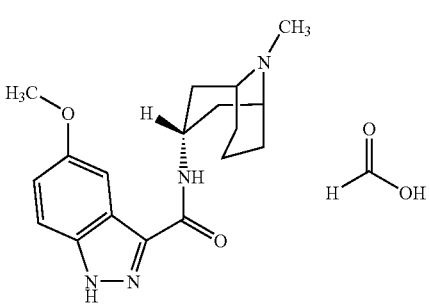

Prepared by Procedure A in 44% yield. LC/MS (EI) $t_R$ 2.56 min, m/z 329 (M$^+$+1).

Example 39

7-Methoxy-N-(endo-8-methyl-8-azabicyclo[3.2.1]oct-3-yl)-1,2-benzisothiazole-3-carboxamide hydroformate

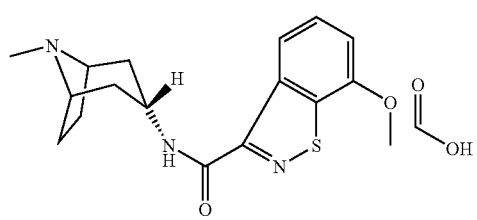

Prepared by Procedure A in 5% yield. LC/MS (EI) $t_R$ 3.96 min, m/z 332 (M$^+$+1).

Example 40

N-(1H-Indazol-3-ylmethyl)-N,8-dimethyl-8-azabicyclo[3.2.1]octan-3-amine dihydroformate

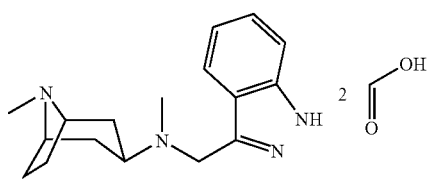

Prepared by Procedure A in 60% yield. LC/MS (EI) $t_R$ 1.34 min, m/z 285 (M$^+$+1).

Example 41

N-(2-Azabicyclo[2.2.1]hept-5-yl)-1H-indazole-3-carboxamide

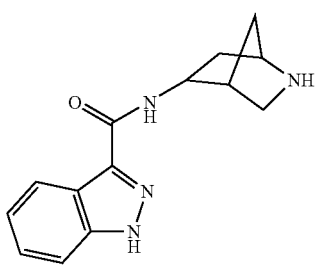

Prepared by Procedure A in 37% yield. LC/MS (EI) $t_R$ 2.73 min, m/z 257 (M$^+$+1).

Example 42

N-(2-Methyl-2-azabicyclo[2.2.2]oct-5-yl)-1H-indazole-3-carboxamide

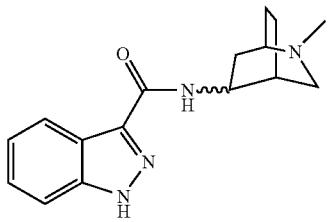

Prepared by Procedure A in 65% yield. LC/MS (EI) $t_R$ 2.92 min, m/z 285 (M$^+$+1).

Example 43

N-(8-Azabicyclo[3.2.1]oct-3-yl)-1H-indazole-3-carboxamide hydrochloride

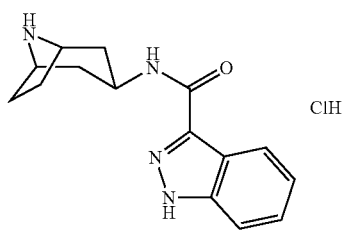

Prepared by Procedure A in 91% yield. LC/MS (EI) $t_R$ 2.70 min, m/z 271 (M$^+$+1).

Example 44

N-(8-Methyl-8-azabicyclo[3.2.1]oct-3-yl)-1,2-benzisoxazole-3-carboxamide hydroformate

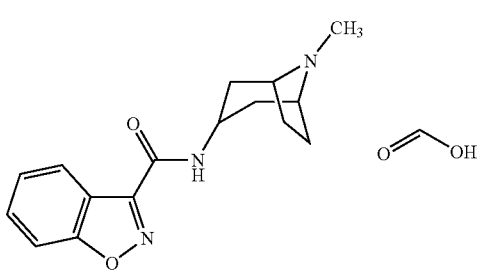

Prepared by Procedure A in 20% yield. LC/MS (EI) $t_R$ 3.53 min, m/z 286 (M$^+$+1).

Example 45

N-(8-Methyl-8-azabicyclo[3.2.1]oct-3-yl)-1H-indazole-3-carboxamide hydroformate

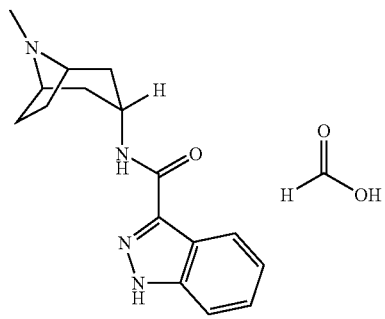

Prepared by Procedure A in 12% yield. LC/MS (EI) $t_R$ 2.55 min, m/z 285 (M$^+$+1).

Example 46

N-(8-Methyl-8-azabicyclo[3.2.1]oct-3-yl)-1H-indazole-3-carboxamide

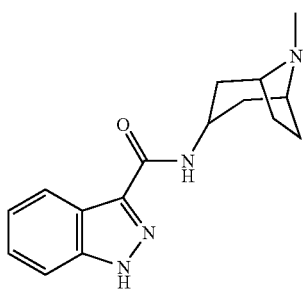

Prepared by Procedure A in 64% yield. LC/MS (EI) $t_R$ 2.85 min, m/z 285 (M$^+$+1).

Example 47

N-(8-Methyl-8-azabicyclo[3.2.1]oct-3-yl)-5-(trifluoromethoxy)-1H-indazole-3-carboxamide hydroformate

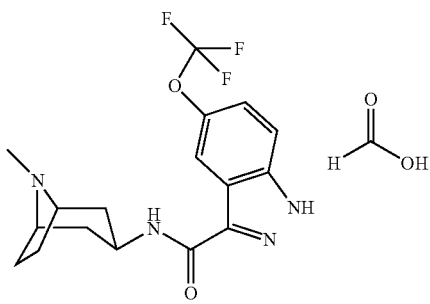

Prepared by Procedure A in 15% yield. LC/MS (EI) $t_R$ 5.19 min, m/z 369 (M$^+$+1).

Example 48

N-(8-Methyl-8-azabicyclo[3.2.1]oct-3-yl)-5-nitro-1H-indazole-3-carboxamide hydroformate

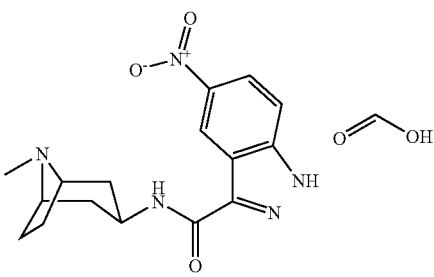

Prepared by Procedure A in 1% yield. LC/MS (EI) $t_R$ 2.89 min, m/z 330 (M$^+$+1).

Example 49

N-(8-Methyl-8-azabicyclo[3.2.1]oct-3-yl)-6-(nitro)-1H-indazole-3-carboxamide hydroformate

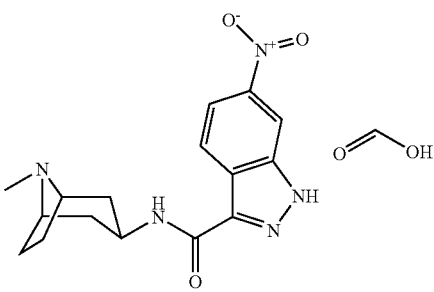

Prepared by Procedure A in 10% yield. LC/MS (EI) $t_R$ 4 min, m/z 330 (M$^+$+1).

Example 50

N-(8-Methyl-8-azabicyclo[3.2.1]oct-3-yl)-6-(trifluoromethoxy)-1H-indazole-3-carboxamide hydroformate

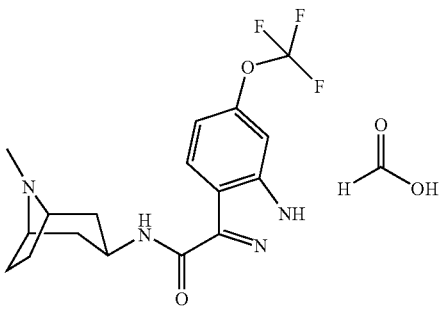

Prepared by Procedure A in 20% yield. LC/MS (EI) $t_R$ 4.93 min, m/z 369 (M$^+$+1).

Example 51

N-(8-Methyl-8-azabicyclo[3.2.1]oct-3-yl)-7-(trifluoromethoxy)-1H-indazole-3-carboxamide hydroformate

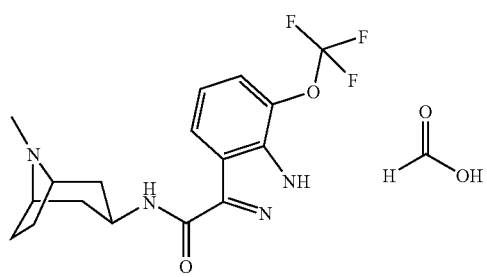

Prepared by Procedure A in 38% yield. LC/MS (EI) $t_R$ 4.73 min, m/z 369 (M$^+$+1).

Example 52

N-(endo-9-Methyl-9-azabicyclo[3.3.1]non-3-yl)-1H-indazole-3-carboxamide hydroformate

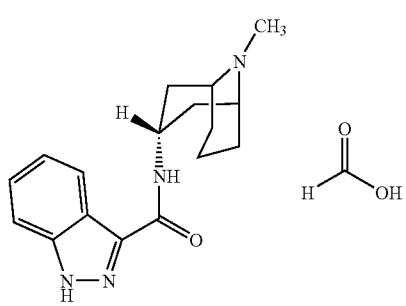

Prepared by Procedure A in 60% yield. LC/MS (EI) $t_R$ 2.95 min, m/z 299 (M$^+$+1).

Example 53

N-(endo-9-Methyl-9-azabicyclo[3.3.1]non-3-yl)-5-(trifluoromethoxy)-1H-indazole-3-carboxamide hydroformate

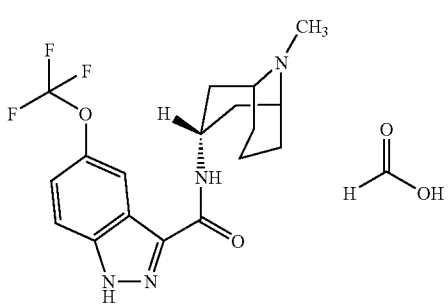

Prepared by Procedure A in 10% yield. LC/MS (EI) $t_R$ 5.29 min, m/z 383 (M$^+$+1).

Example 54

N-(endo-9-Methyl-9-azabicyclo[3.3.1]non-3-yl)-5-nitro-1H-indazole-3-carboxamide hydroformate

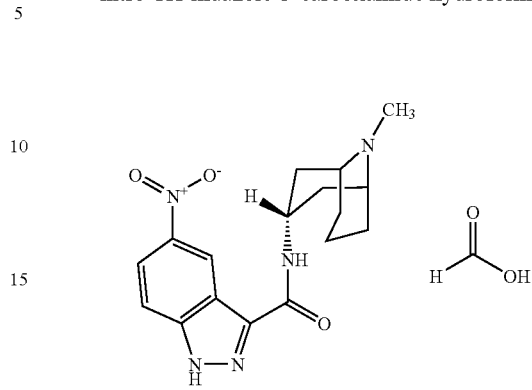

Prepared by Procedure A in 1% yield. LC/MS (EI) $t_R$ 3.89 min, m/z 343 (M$^+$+1).

Example 55

N-(endo-8-Methyl-8-azabicyclo[3.2.1]oct-3-yl)-5-(nitro)-1H-indazole-3-carboxamide hydroformate

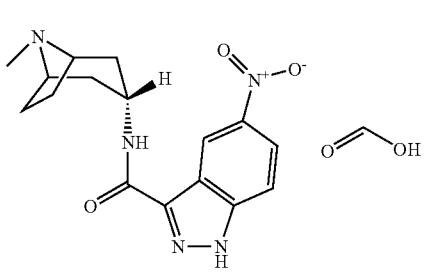

Prepared by Procedure A in 2% yield. LC/MS (EI) $t_R$ 3.87 min, m/z 330 (M$^+$+1).

Example 56

N-(endo-8-Methyl-8-azabicyclo[3.2.1]oct-3-yl)-5-(trifluoromethoxy)-1H-indazole-3-carboxamide hydroformate

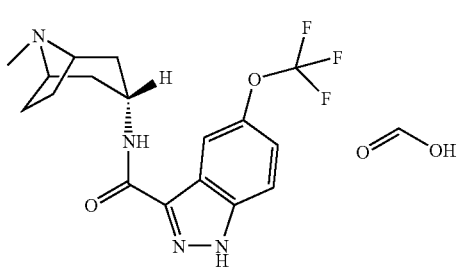

Prepared by Procedure A in 21% yield. LC/MS (EI) $t_R$ 4.73 min, m/z 369 (M$^+$+1).

Example 57

N-(endo-8-Methyl-8-azabicyclo[3.2.1]oct-3-yl)-6-(nitro)-1H-indazole-3-carboxamide hydroformate

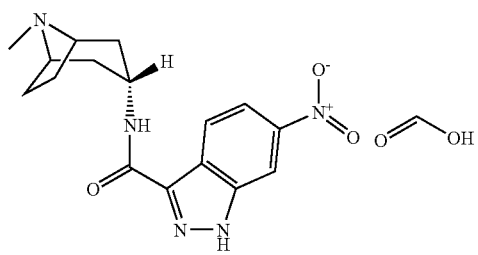

Prepared by Procedure A in 7% yield. LC/MS (EI) $t_R$ 3.96 min, m/z 330 (M$^+$+1).

Example 58

N-(endo-8-Methyl-8-azabicyclo[3.2.1]oct-3-yl)-6-(trifluoromethoxy)-1H-indazole-3-carboxamide hydroformate

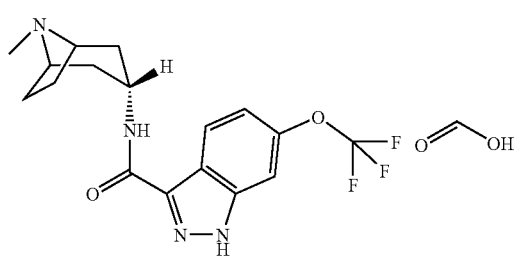

Prepared by Procedure A in 28% yield. LC/MS (EI) $t_R$ 5.01 min, m/z 369 (M$^+$+1).

Example 59

N-(exo-8-Methyl-8-azabicyclo[3.2.1]oct-3-yl)-5-(nitro)-1H-indazole-3-carboxamide hydroformate

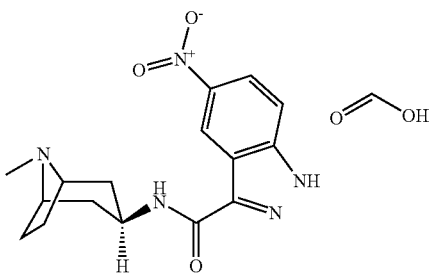

Prepared by Procedure A in 2% yield. LC/MS (EI) $t_R$ 3.69 min, m/z 330 (M$^+$+1).

Example 60

N-(exo-8-Methyl-8-azabicyclo[3.2.1]oct-3-yl)-5-(trifluoromethoxy)-1H-indazole-3-carboxamide hydroformate

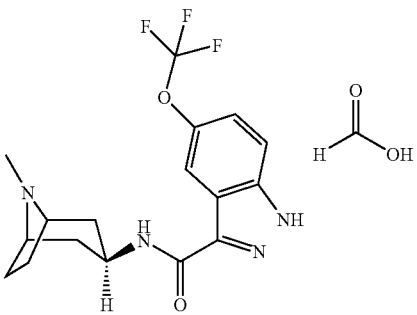

Prepared by Procedure A in 30% yield. LC/MS (EI) $t_R$ 5.09 min, m/z 369 (M$^+$+1).

Example 61

N-(exo-8-Methyl-8-azabicyclo[3.2.1]oct-3-yl)-6-(nitro)-1H-indazole-3-carboxamide hydroformate

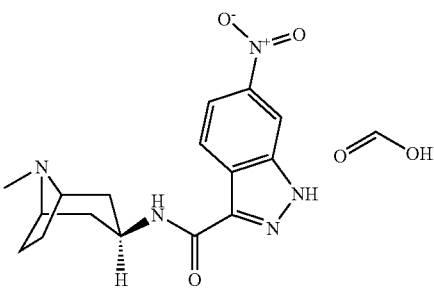

Prepared by Procedure A in 4% yield. LC/MS (EI) $t_R$ 4 min, m/z 330 (M$^+$+1).

Example 62

N-(exo-8-Methyl-8-azabicyclo[3.2.1]oct-3-yl)-6-(trifluoromethoxy)-1H-indazole-3-carboxamide hydroformate

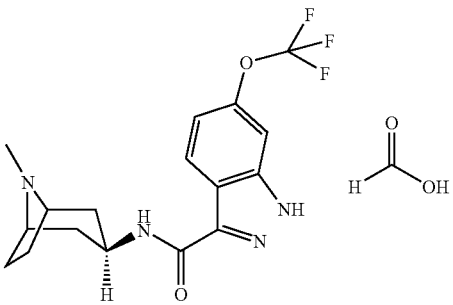

Prepared by Procedure A in 10% yield. LC/MS (EI) $t_R$ 4.89 min, m/z 369 (M$^+$+1).

Example 63

N-[(rel-6R,8aS)-Octahydroindolizin-6-yl]-1H-indazole-3-carboxamide hydroformate

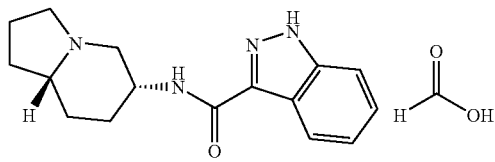

Prepared by Procedure A in 21% yield. LC/MS (EI) $t_R$ 2.93 min, m/z 285 (M$^+$+1).

Example 64

N-[(rel-6S,8aS)-Octahydroindolizin-6-yl]-1H-indazole-3-carboxamide hydroformate

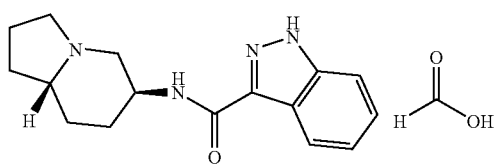

Prepared by Procedure A in 45% yield. LC/MS (EI) $t_R$ 2.94 min, m/z 285 (M$^+$+1).

Example 65

N-Methyl-N-(8-methyl-8-azabicyclo[3.2.1]oct-3-yl)-1H-indazole-3-carboxamide hydroformate

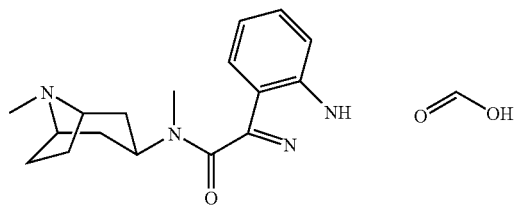

Prepared by Procedure A in 12% yield. LC/MS (EI) $t_R$ 2.56 min, m/z 299 (M$^+$+1).

Example 66

N-Methyl-N-(8-methyl-8-azabicyclo[3.2.1]oct-3-yl)-1H-indazole-3-carboxamide

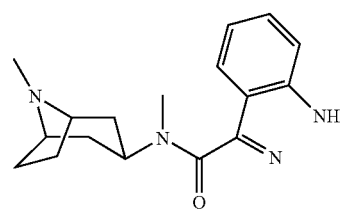

Prepared by Procedure A in 12% yield. LC/MS (EI) $t_R$ 2.52 min, m/z 299 (M$^+$+1).

Example 67

2-[(6-Methoxy-1H-indazol-3-yl)carbonyl]octahydro-2H-pyrido[1,2-a]pyrazine hydroformate

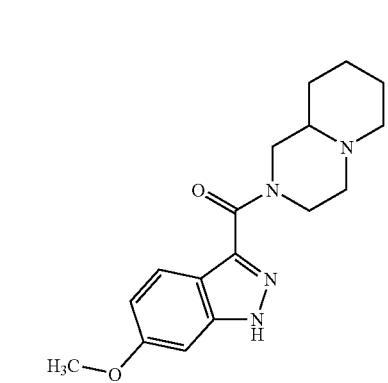

Prepared by Procedure A in 60% yield. LC/MS (EI) $t_R$ 2.65 min, m/z 315 (M$^+$+1).

Example 68

7-Methoxy-N-(endo-9-methyl-9-azabicyclo[3.3.1]non-3-yl)-1H-indazol-3-carboxamide hydroformate Prepared by Procedure A in 45% yield. LC/MS (EI) $t_R$ 2.56 min, m/z 329 (M$^+$+1).

Example 69

6-Methoxy-N-(endo-8-methyl-8-azabicyclo[3.2.1]oct-3-yl)-1,2-benzisothiazole-3-carboxamide hydroformate Prepared by Procedure A in 38% yield. LC/MS (EI) $t_R$ 3.58 min, m/z 332 (M$^+$+1).

Example 70

6-Methoxy-N-(exo-8-methyl-8-azabicyclo[3.2.1]oct-3-yl)-1,2-benzisothiazole-3-carboxamide hydroformate

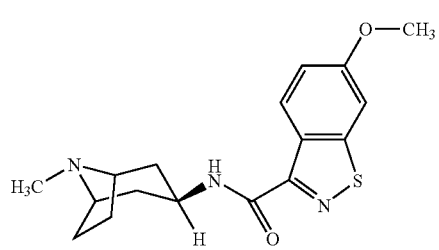

Prepared by Procedure A in 38% yield. LC/MS (EI) $t_R$ 3.54 min, m/z 332 (M$^+$+1).

Example 71

N-(2-Methyl-2-azabicyclo[2.2.1]hept-5-yl)-5-(trifluoromethoxy)-1H-indazole-3-carboxamide hydroformate

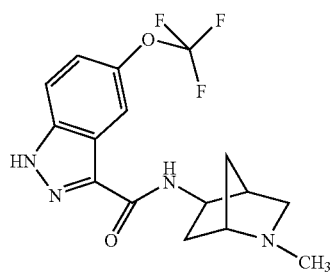

Prepared by Procedure A in 30% yield. LC/MS (EI) $t_R$ 4.15 min, m/z 355 (M$^+$+1).

Example 72

6-Methoxy-N-(2-methyl-2-azabicyclo[2.2.1]hept-5-yl)-1H-indazole-3-carboxamide hydroformate

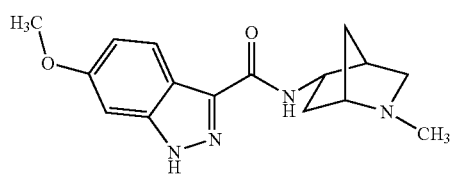

Prepared by Procedure A in 50% yield. LC/MS (EI) $t_R$ 1.7 min, m/z 301 (M$^+$+1).

Example 73

N-(2-Methyl-2-azabicyclo[2.2.1]hept-5-yl)-6-(4-methyl-1,3-thiazol-2-yl)-1H-indazole-3-carboxamide hydroformate

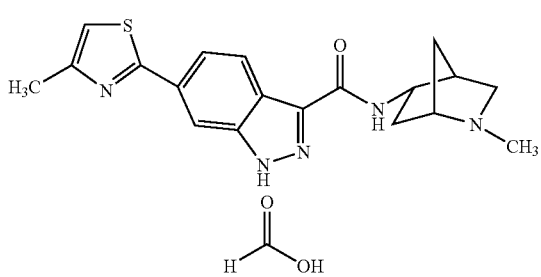

Prepared by Procedure A in 20% yield. LC/MS (EI) $t_R$ 4.78 min, m/z 368 (M$^+$+1).

Example 74

5-Difluoromethoxy-N-(endo-8-methyl-8-azabicyclo[3.2.1]oct-3-yl)-1H-indazole-3-carboxamide hydroformate

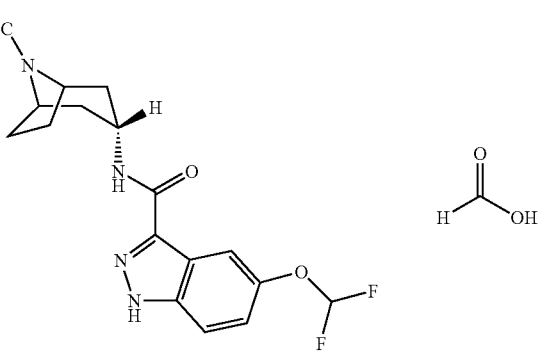

Prepared by Procedure A in 40% yield. LC/MS (EI) $t_R$ 4.27 min, m/z 351 (M$^+$+1).

Example 75

5-Difluoromethoxy-N-(exo-8-methyl-8-azabicyclo[3.2.1]oct-3-yl)-1H-indazole-3-carboxamide hydroformate

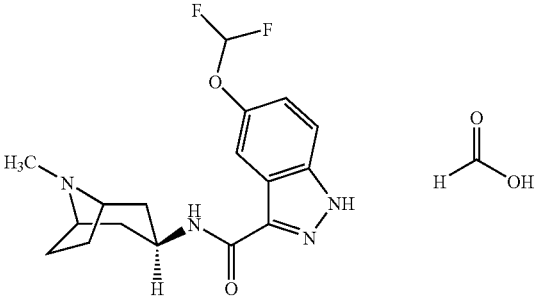

Prepared by Procedure A in 30% yield. LC/MS (EI) $t_R$ 4.25 min, m/z 351 (M$^+$+1).

Example 76

5-Difluoromethoxy-N-(8-methyl-8-azabicyclo[3.2.1]oct-3-yl)-1H-indazole-3-carboxamide hydroformate

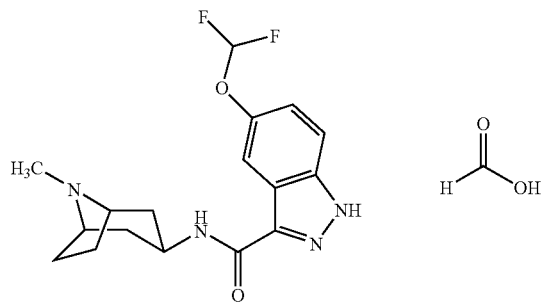

Prepared by Procedure A in 40% yield. LC/MS (EI) $t_R$ 4.33 min, m/z 351 (M$^+$+1).

Example 77

6-Difluoromethoxy-N-(endo-8-methyl-8-azabicyclo[3.2.1]oct-3-yl)-1H-indazole-3-carboxamide hydroformate

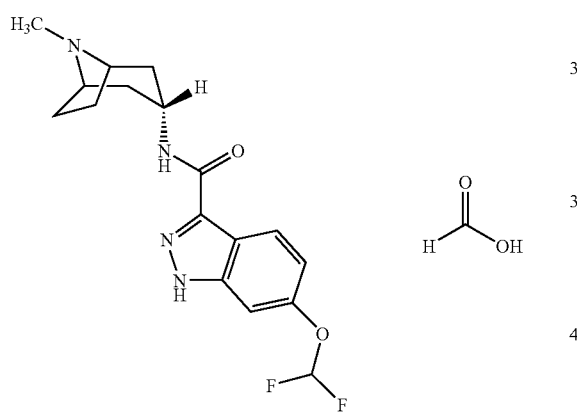

Prepared by Procedure A in 61% yield. LC/MS (EI) $t_R$ 4.15 min, m/z 351 (M$^+$+1).

Example 78

6-Difluoromethoxy-N-(8-methyl-8-azabicyclo[3.2.1]oct-3-yl)-1H-indazole-3-carboxamide hydroformate

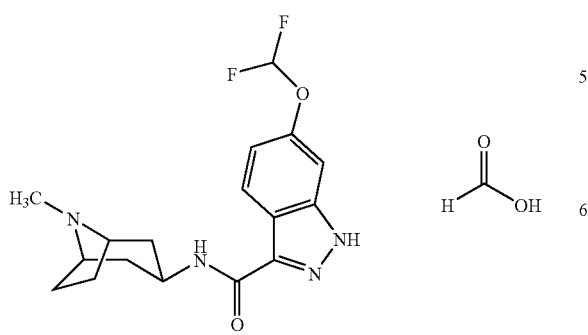

Prepared by Procedure A in 50% yield. LC/MS (EI) $t_R$ 4.18 min, m/z 351 (M$^+$+1).

Example 79

N-(8-Methyl-8-azabicyclo[3.2.1]oct-3-yl)-5-(4-methyl-1,3-thiazol-2-yl)-1H-indazole-3-carboxamide

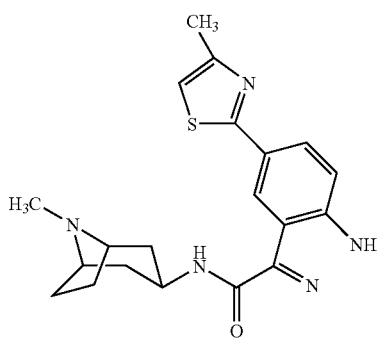

Prepared by Procedure A in 29% yield. LC/MS (EI) $t_R$ 4.27 min, m/z 382 (M$^+$+1).

Example 80

N-(exo-8-Methyl-8-azabicyclo[3.2.1]oct-3-yl)-5-(4-methyl-1,3-thiazol-2-yl)-1H-indazole-3-carboxamide hydroformate

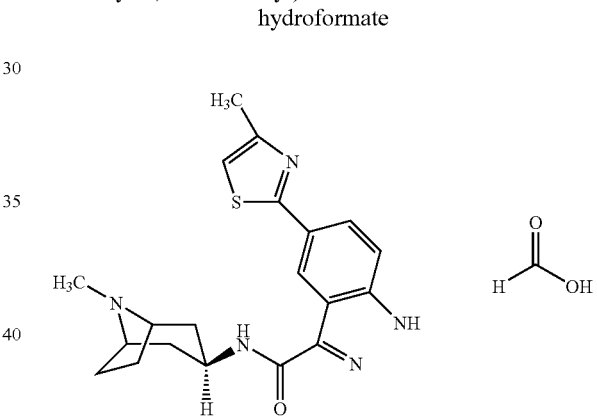

Prepared by Procedure A in 11% yield. LC/MS (EI) $t_R$ 4.32 min, m/z 3 82 (M$^+$+1).

Example 81

N-(2-Methyl-2-azabicyclo[2.2.1]hept-5-yl)-5-(4-methyl-1,3-thiazol-2-yl)-1H-indazole-3-carboxamide hydroformate

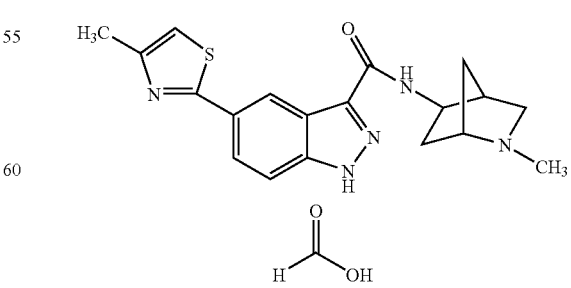

Prepared by Procedure A in 46% yield. LC/MS (EI) $t_R$ 4.02 min, m/z 368 (M$^+$+1).

Example 82

6-(3,6-Dihydro-2H-pyran-4-yl)-N-(2-methyl-2-azabicyclo[2.2.1]hept-5-yl)-1H-indazole-3-carboxamide hydroformate

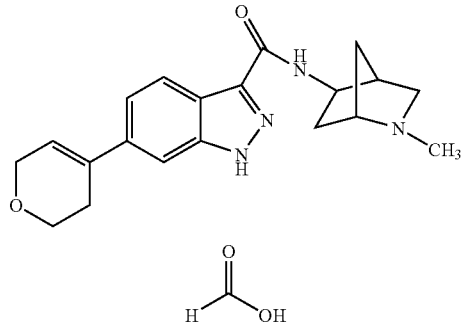

Prepared by Procedure A in 48% yield. LC/MS (EI) $t_R$ 2.79 min, m/z 353 (M$^+$+1).

Example 83

N-(2-Methyl-2-azabicyclo[2.2.1]hept-5-yl)-6-(5-methyl-1,3-thiazol-2-yl)-1H-indazole-3-carboxamide hydroformate

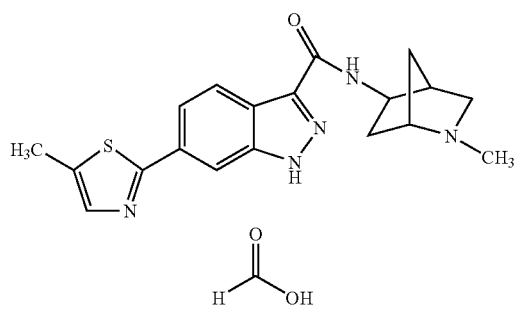

Prepared by Procedure A in 56% yield. LC/MS (EI) $t_R$ 4.31 min, m/z 368 (M$^+$+1).

Example 84

6-Difluoromethoxy-N-(2-methyl-2-azabicyclo[2.2.1]hept-5-yl)-1H-indazole-3-carboxamide hydroformate

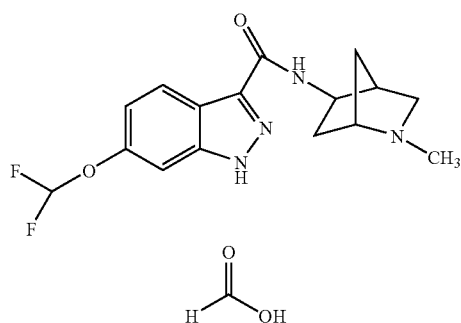

Prepared by Procedure A in 56% yield. LC/MS (EI) $t_R$ 2.97 min, m/z 337 (M$^+$+1).

Example 85

N-(2-Methyl-2-azabicyclo[2.2.1]hept-5-yl)-6-(1,3-thiazol-2-yl)-1H-indazole-3-carboxamide hydroformate

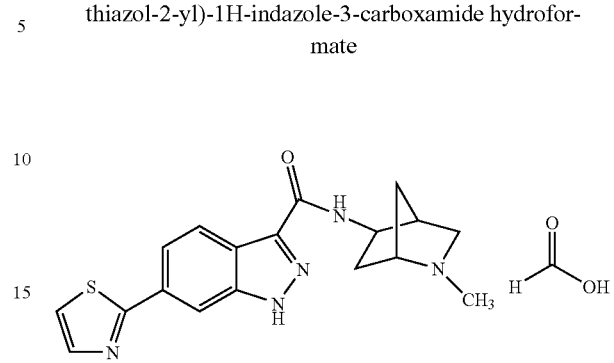

Prepared by Procedure A in 58% yield. LC/MS (EI) $t_R$ 3.13 min, m/z 354(M$^+$+1).

Example 86

N-(2-Methyl-2-azabicyclo[2.2.1]hept-5-yl)-5-(5-methyl-1,3-thiazol-2-yl)-1H-indazole-3-carboxamide hydroformate

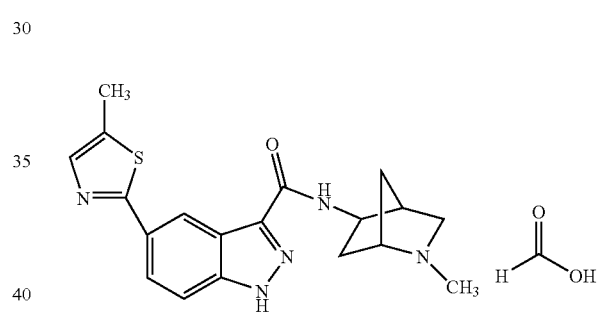

Prepared by Procedure A in 46% yield. LC/MS (EI) $t_R$ 3.66 min, m/z 368 (M$^+$+1).

Example 87

N-(2-Methyl-2-azabicyclo[2.2.1]hept-5-yl)-6-(trifluoromethoxy)-1H-indazole-3-carboxamide hydroformate

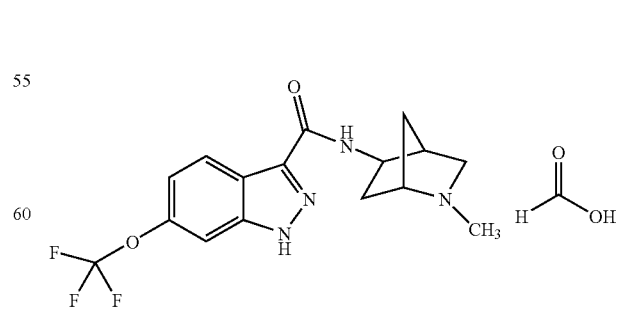

Prepared by Procedure A in 48% yield. LC/MS (EI) $t_R$ 4.64 min, m/z 355 (M$^+$+1).

Example 88

N-(endo-8-Methyl-8-azabicyclo[3.2.1]oct-3-yl)-5-(4-methyl-1,3-thiazol-2-yl)-1H-indazole-3-carboxamide hydroformate

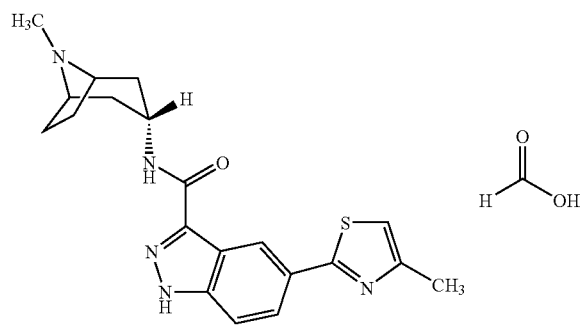

Prepared by Procedure A in 40% yield. LC/MS (EI) $t_R$ 4.23 min, m/z 382 (M$^+$+1).

Example 89

N-(2-Methyl-2-azabicyclo[2.2.1]hept-5-yl)-6-(2-thienyl)-1H-indazole-3-carboxamide hydroformate

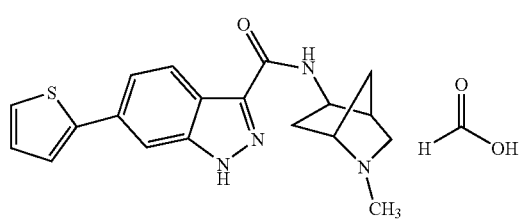

Prepared by Procedure A in 54% yield. LC/IS (EI) $t_R$ 4.85 min, m/z 353 (M$^+$+1).

Example 90

N-(2-Methyl-2-azabicyclo[2.2.1]hept-5-yl)-5-(1,3-oxazol-2-yl)-1H-indazole-3-carboxamide hydroformate

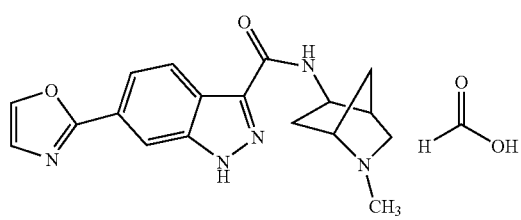

Prepared by Procedure A in 42% yield. LC/MS (EI) $t_R$ 2.46 min, m/z 338 (M$^+$+1).

Example 91

5-(3,6-Dihydro-2H-pyran-4-yl)-N-(2-methyl-2-azabicyclo[2.2.1]hept-5-yl)-1H-indazole-3-carboxamide hydroformate

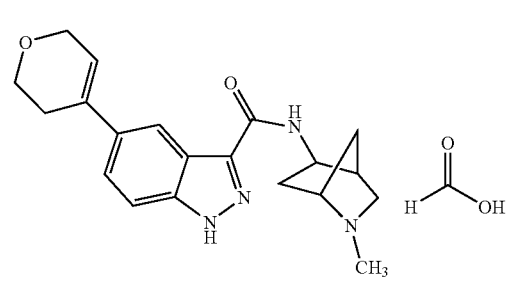

Prepared by Procedure A in 46% yield. LC/MS (EI) $t_R$ 2.83 min, m/z 353 (M$^+$+1).

Example 92

5-Methoxy-N-(2-methyl-2-azabicyclo[2.2.1]hept-5-yl)-1H-indazole-3-carboxamide hydroformate

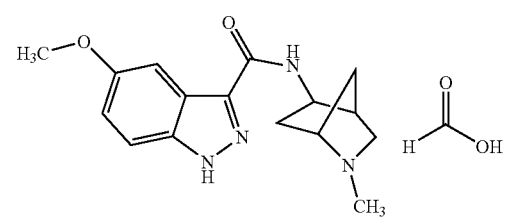

Prepared by Procedure A in 61% yield. LC/MS (EI) $t_R$ 2.41 min, m/z 301 (M$^+$+1).

Example 93

N-[(rel-1S,4S,5S)-2-Methyl-2-azabicyclo[2.2.1]hept-5-yl]-6-(4-methyl-1,3-thiazol-2-yl)-1H-indazole-3-carboxamide

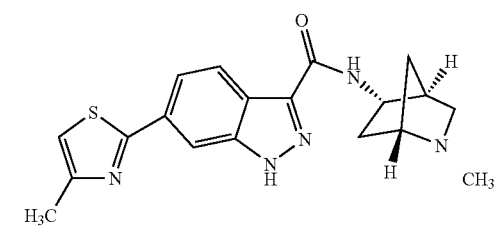

Prepared by Procedure A in 23% yield. LC/MS (EI) $t_R$ 4.04 min, m/z 368 (M$^+$+1).

Example 94

N-[(rel-1S,4S,5R)-2-Methyl-2-azabicyclo[2.2.1]hept-5-yl]-6-(4-methyl-1,3-thiazol-2-yl)-1H-indazole-3-carboxamide

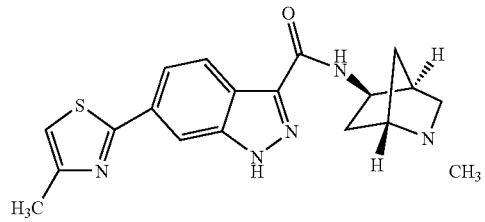

Prepared by Procedure A in 32% yield. LC/MS (EI) $t_R$ 4.04 min, m/z 368 (M$^+$+1).

Example 95

N-[(rel-1S,4S,5R)-2-Methyl-2-azabicyclo[2.2.1]hept-5-yl]-5-(trifluoromethoxy)-1H-indazole-3-carboxamide

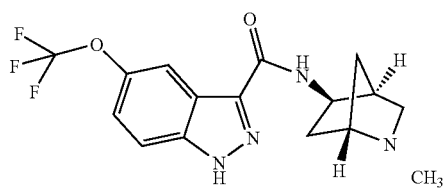

Prepared by Procedure A in 30% yield. LC/MS (EI) $t_R$ 4.68 min, m/z 355 (M$^+$+1).

Example 96

N-[(rel-1S,4S,5S)-2-Methyl-2-azabicyclo[2.2.1]hept-5-yl]-5-(trifluoromethoxy)-1H-indazole-3-carboxamide

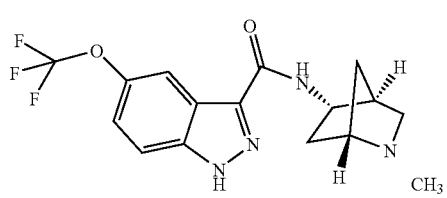

Prepared by Procedure A in 27% yield. LC/MS (EI) $t_R$ 4.68 min, m/z 355 (M$^+$+1).

Example 97

N-(2-Methyl-2-azabicyclo[2.2.1]hept-5-yl)-5-(1,3-thiazol-2-yl)-1H-indazole-3-carboxamide hydroformate

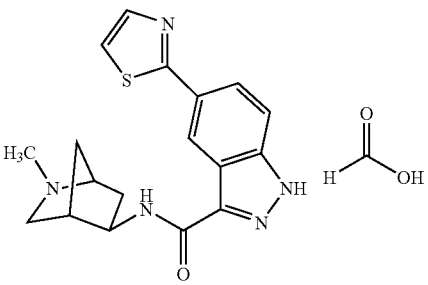

Prepared by Procedure A in 50% yield. LC/MS (EI) $t_R$ 4.47 min, m/z 354 (M$^+$+1).

Example 98

N-(endo-8-methyl-8-azabicyclo[3.2.1]oct-3-yl)-5-(1,3-oxazol-2-yl)-1H-indazole-3-carboxamide hydroformate

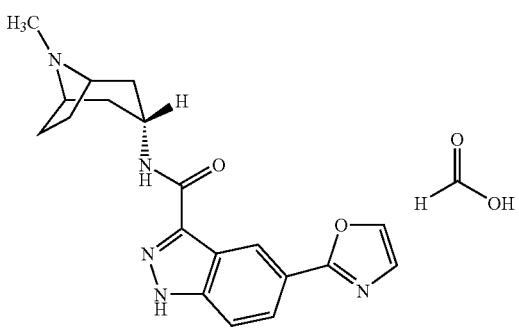

Prepared by Procedure A in 9% yield. LC/MS (EI) $t_R$ 2.98 min, m/z 352 (M$^+$+1).

Example 99

N-(2-Methyl-2-azabicyclo[2.2.1]hept-5-yl)-6-(5-methyl-1,3-thiazol-2-yl)-1H-indazole-3-carboxamide hydroformate

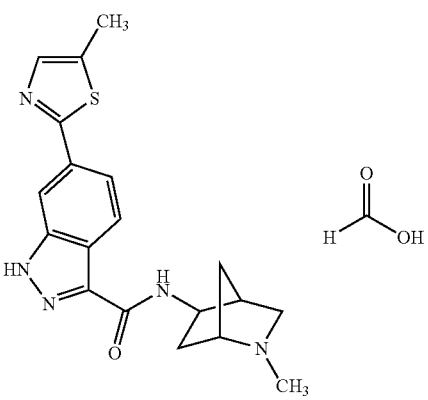

Prepared by Procedure A in 20% yield. LC/MS (EI) $t_R$ 4.37 min, m/z 368 (M$^+$+1).

Example 100

N-(2-Methyl-2-azabicyclo[2.2.1]hept-5-yl)-5-(trifluoromethoxy)-1H-indazole-3-carboxamide hydroformate

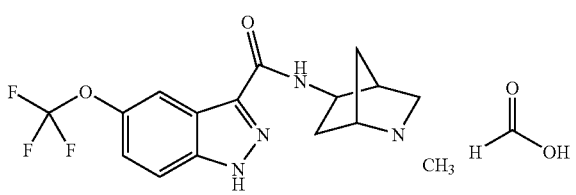

Prepared by Procedure A in 54% yield. LC/MS (EI) $t_R$ 4.68 min, m/z 355 (M$^+$+1).

Example 101

N-(2-Methyl-2-azabicyclo[2.2.1]hept-5-yl)-6-(4-methyl-1,3-thiazol-2-yl)-1H-indazole-3-carboxamide hydroformate

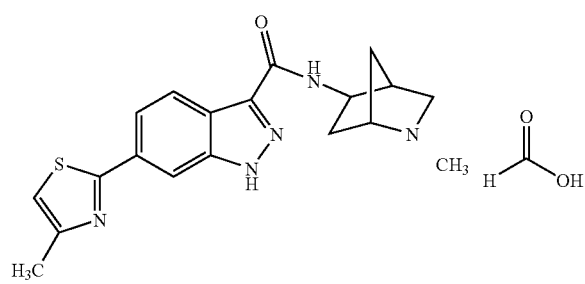

Prepared by Procedure A in 55% yield. LC/MS (EI) $t_R$ 4.04 min, m/z 368 (M$^+$+1).

Representative Procedure B.

Procedure B provides a method for the coupling between brominated bicyclobase carboxamides and boronic acids to form aryl-substituted derivatives.

Example 102

5-(3-Furyl)-N-(8-methyl-8-azabicyclo[3.2.1]oct-3-yl)-1H-indazole-3-carboxamide

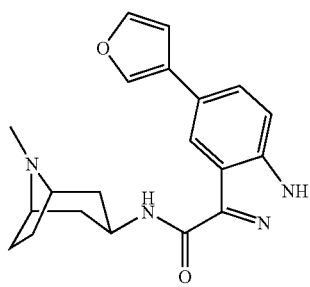

In a 5 mL microwave reaction vessel was added N-(8-methyl-8-azabicyclo[3.2.1]octan-3-yl)-5-bromo-1H-indazole-3-carboxamide (0.286 mmol), furan-3-boronic acid (0.588 mmol), tris(dibenzylideneacetone)dipalladium (0) (0.0289 mmol), tri-tert-butylphosphine tetrafluoroborate (0.0579 mmol), and potassium carbonate (0.810 mmol). The vessel was evacuated, back-filled with argon gas, and the contents diluted with N,N-dimethylformamide (5.0 mL). The vessel was sealed and subjected to microwave irradiation at 200° C. for 600 s. The contents of the reaction were filtered through Celite (methanol wash) and loaded on a 5 g SCX column. The column was washed with methanol (50 mL) and the product was eluted with 2 M ammonia in methanol and concentrated. The residue was purified by chromatography [1/1 to 0/1 ethyl acetate/(70/30/1 ethyl acetate/methanol/ammonium hydroxide)] followed by preparative HPLC, thus providing the product in 4% yield. $^1$H NMR (CD$_3$OD) δ 6 8.51 (s, 1 H), 8.35 (s, 1H), 7.93 (s, 1 H), 7.70-7.58 (m, 3 H), 6.87 (s, 1 H), 4.56-4.52 (m, 0.5 H), 4.28-4.26 (m, 0.5 H), 3.97-3.93 (m, 2 H), 2.84 (s, 3 H), 2.49-2.12 (m, 8 H); LC/MS (EI) $t_R$ 4.20 min, m/z 351 (M$^+$+1).

Using this general procedure the following compounds were prepared:

Example 103

(8-Methyl-8-azabicyclo[3.2.1]non-3-yl)-6-(2-thienyl)-1H-indazole-3-carboxamide hydroformate

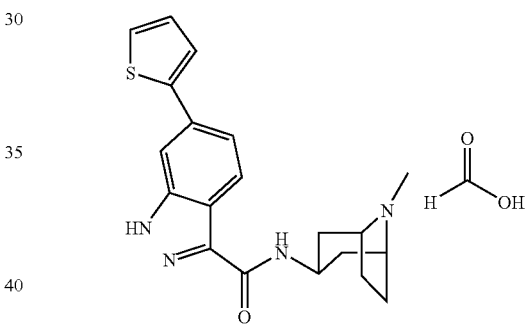

Prepared by Procedure B in 26% yield. LC/MS (EI) $t_R$ 4.50 min, m/z 367 (M$^+$+1).

Example 104

5-(1-Benzyl-1H-pyrazol-4-yl)-N-(endo-9-methyl-9-azabicyclo[3.3.1]non-3-yl)-1H-indazole-3-carboxamide hydroformate

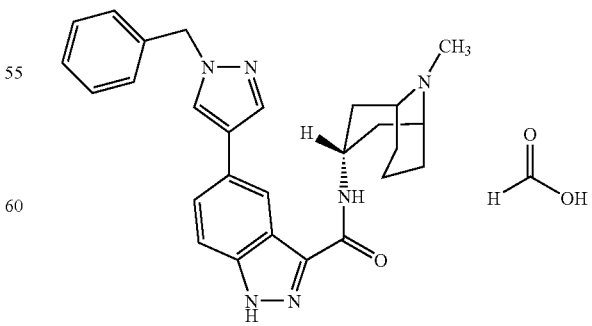

Prepared by Procedure B in 10% yield. LC/MS (EI) $t_R$ 5.39 min, m/z 455 (M$^+$+1).

Example 105

5-(2,3'-Bithien-5-yl)-N-(endo-9-methyl-9-azabicyclo[3.3.1]non-3-yl)-1H-indazole-3-carboxamide hydroformate

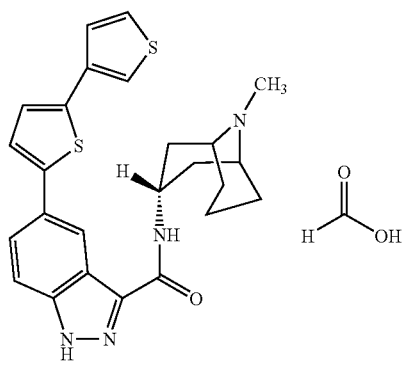

Prepared by Procedure B in 8% yield. LC/MS (EI) $t_R$ 5.43 min, m/z 463 (M$^+$+1).

Example 106

5-(2-Furyl)-N-(8-methyl-8-azabicyclo[3.2.1]oct-3-yl)-1H-indazole-3-carboxamide

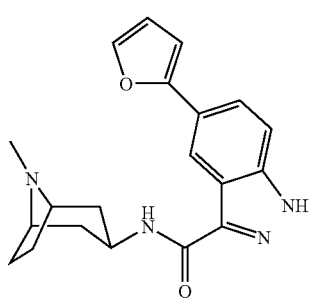

Prepared by Procedure B in 10% yield. LC/MS (EI) $t_R$ 4.30 min, m/z 351 (M$^+$+1).

Example 107

5-(3,5-Dimethylisoxazol-4-yl)-N-(8-methyl-8-azabicyclo[3.2.1]oct-3-yl)-1H-indazole-3-carboxamide hydroformate

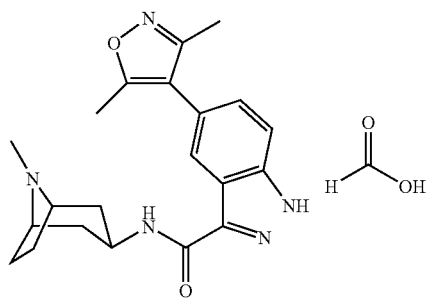

Prepared by Procedure B in 3% yield. LC/MS (EI) $t_R$ 4.49 min, m/z 380 (M$^+$+1).

Example 108

5-(3-Furyl)-N-(8-methyl-8-azabicyclo[3.2.1]oct-3-yl)-1H-indazole-3-carboxamide hydroformate

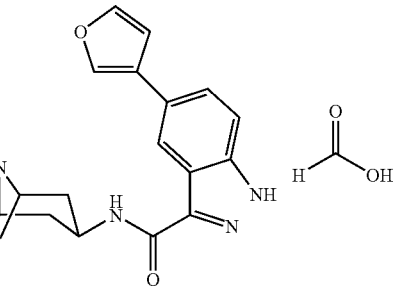

Prepared by Procedure B in 4% yield. LC/MS (EI) $t_R$ 4.12 min, m/z 351 (M$^+$+1).

Example 109

5-(3-Furyl)-N-(endo-9-methyl-9-azabicyclo[3.3.1]non-3-yl)-1H-indazole-3-carboxamide hydroformate

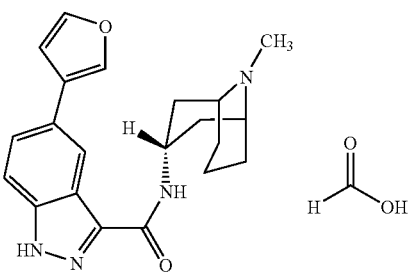

Prepared by Procedure B in 13% yield. LC/MS (EI) $t_R$ 4.40 min, m/z 365 (M$^+$+1).

Example 110

5-(4-Fluorophenyl)-N-(8-methyl-8-azabicyclo[3.2.1]oct-3-yl)-1H-indazole-3-carboxamide hydroformate

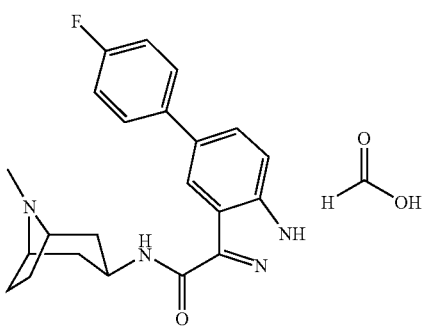

Prepared by Procedure B in 4% yield. LC/MS (EI) $t_R$ 4.60 min, m/z 379 (M$^+$+1).

Example 111

5-(4-Fluorophenyl)-N-(8-methyl-8-azabicyclo[3.2.1]oct-3-yl)-1H-indazole-3-carboxamide

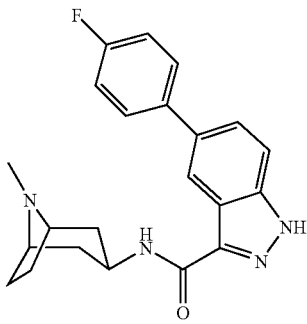

Prepared by Procedure B in 4% yield. LC/MS (EI) $t_R$ 4.60 min, m/z 379 (M$^+$+1).

Example 112

6-(2-Furyl)-N-(8-methyl-8-azabicyclo[3.2.1]oct-3-yl)-1H-indazole-3-carboxamide hydroformate

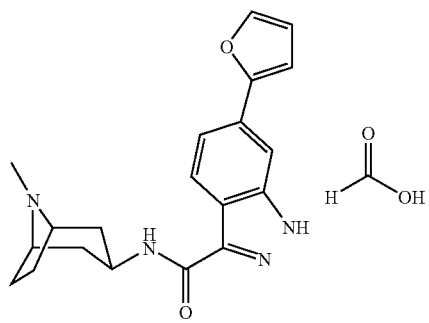

Prepared by Procedure B in 28% yield. LC/MS (EI) $t_R$ 5.18 min, m/z 351 (M$^+$+1).

Example 113

6-(3-Furyl)-N-(8-methyl-8-azabicyclo[3.2.1]oct-3-yl)-1H-indazole-3-carboxamide

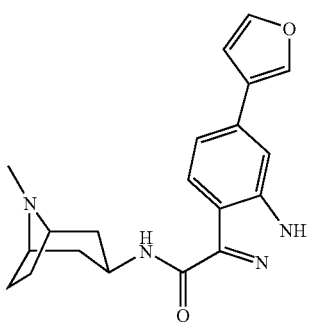

Prepared by Procedure B in 32% yield. LC/MS (EI) $t_R$ 5.00 min, m/z 351 (M$^+$+1).

Example 114

6-(4-Fluorophenyl)-N-(8-methyl-8-azabicyclo[3.2.1]oct-3-yl)-1H-indazole-3-carboxamide hydroformate

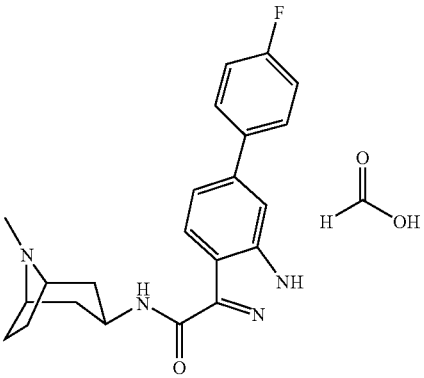

Prepared by Procedure B in 5% yield. LC/MS (EI) $t_R$ 4.68 min, m/z 379 (M$^+$+1).

Example 115

6-(4-Fluorophenyl)-N-(8-methyl-8-azabicyclo[3.2.1]oct-3-yl)-1H-indazole-3-carboxamide

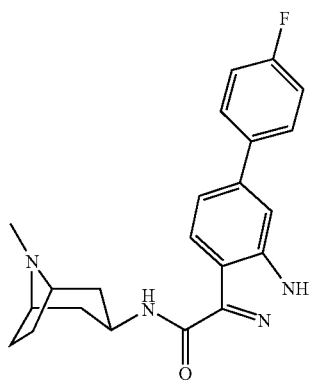

Prepared by Procedure B in 5% yield. LC/MS (EI) $t_R$ 4.70 min, m/z 379 (M$^+$+1).

Example 116

N-(8-Methyl-8-azabicyclo[3.2.1]oct-3-yl)-5-(2-thienyl)-1H-indazole-3-carboxamide

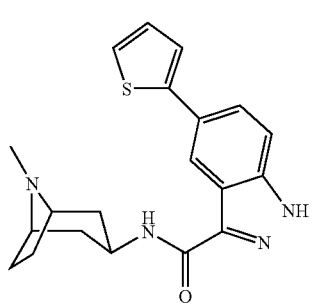

Prepared by Procedure B in 28% yield. LC/MS (EI) $t_R$ 5.30 min, m/z 367 (M$^+$+1).

Example 117

N-(8-Methyl-8-azabicyclo[3.2.1]oct-3-yl)-5-(3-thienyl)-1H-indazole-3-carboxamide hydroformate

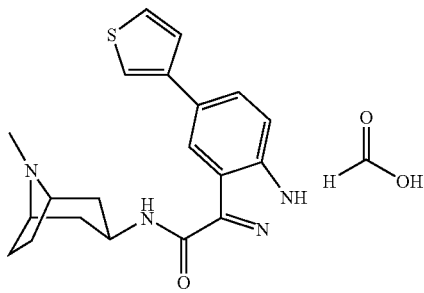

Prepared by Procedure B in 10% yield. LC/MS (EI) $t_R$ 4.39 min, m/z 367 (M$^+$+1).

Example 118

N-(8-Methyl-8-azabicyclo[3.2.1]oct-3-yl)-5-(3-thienyl)-1H-indazole-3-carboxamide

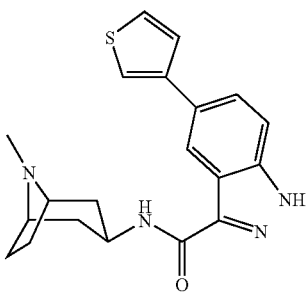

Prepared by Procedure B in 4% yield. LC/MS (EI) $t_R$ 4.40 min, m/z 367 (M$^+$+1).

Example 119

N-(8-Methyl-8-azabicyclo[3.2.1]oct-3-yl)-5-(5-methyl-2-thienyl)-1H-indazole-3-carboxamide hydroformate

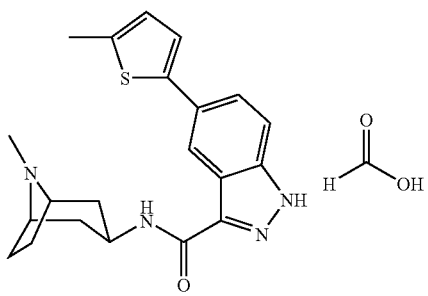

Prepared by Procedure B in 5% yield. LC/MS (EI) $t_R$ 4.74 min, m/z 381 (M$^+$+1).

Example 120

N-(8-Methyl-8-azabicyclo[3.2.1]oct-3-yl)-5-(5-methyl-2-thienyl)-1H-indazole-3-carboxamide

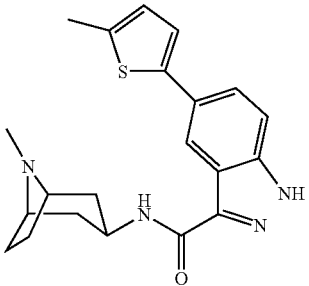

Prepared by Procedure B in 5% yield. LC/MS (EI) $t_R$ 4.70 min, m/z 381 (M$^+$+1).

Example 121

N-(8-Methyl-8-azabicyclo[3.2.1]oct-3-yl)-5-[(3-trifluoromethyl)phenyl]-1H-indazole-3-carboxamide hydroformate

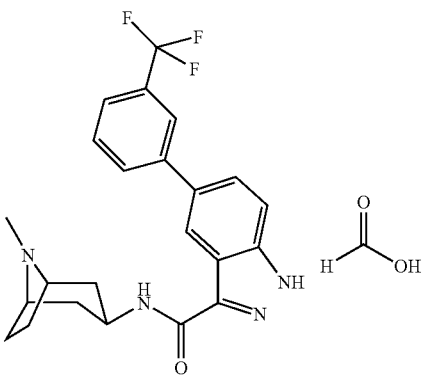

Prepared by Procedure B in 5% yield. LC/MS (EI) $t_R$ 5.01 min, m/z 429 (M$^+$+1).

Example 122

N-(8-Methyl-8-azabicyclo[3.2.1]oct-3-yl)-5-[(3-trifluoromethyl)phenyl]-1H-indazole-3-carboxamide

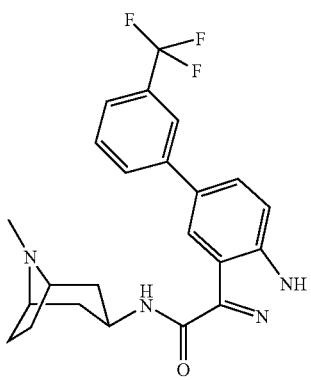

Prepared by Procedure B in 5% yield. LC/MS (EI) $t_R$ 5.00 min, m/z 429 (M$^+$+1).

Example 123

N-(8-Methyl-8-azabicyclo[3.2.1]oct-3-yl)-5-[(4-trifluoromethyl)phenyl]-1H-indazole-3-carboxamide hydroformate

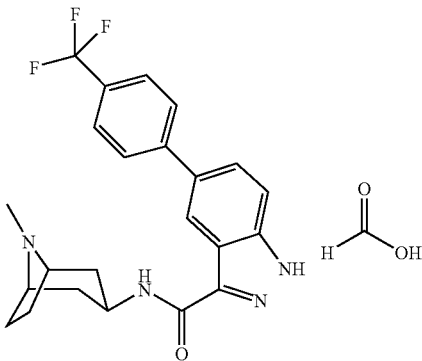

Prepared by Procedure B in 4% yield. LC/MS (EI) $t_R$ 5.06 min, m/z 429 (M$^+$+1).

Example 124

N-(8-Methyl-8-azabicyclo[3.2.1]oct-3-yl)-5-[(4-trifluoromethyl)phenyl]-1H-indazole-3-carboxamide

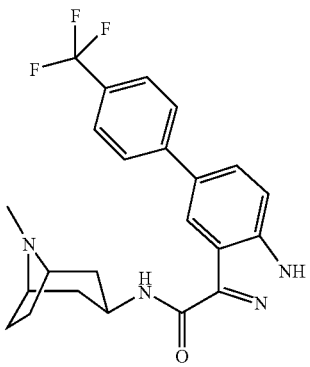

Prepared by Procedure B in 4% yield. LC/MS (EI) $t_R$ 5.00 min, m/z 429 (M$^+$+1).

Example 125

N-(8-Methyl-8-azabicyclo[3.2.1]oct-3-yl)-5-{5-[3-(trifluoromethyl)phenyl]-2-thienyl}-1H-indazole-3-carboxamide hydroformate

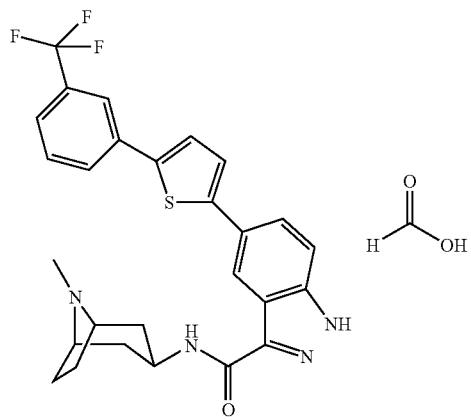

Prepared by Procedure B in 17% yield. LC/MS (EI) $t_R$ 5.34 min, m/z 512 (M$^+$+1)

Example 126

N-(8-Methyl-8-azabicyclo[3.2.1]oct-3-yl)-6-(3-thienyl)-1H-indazole-3-carboxamide

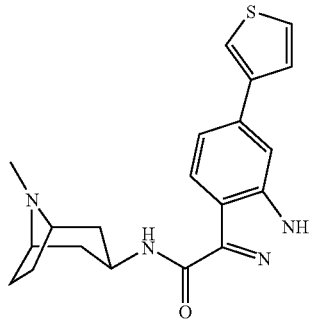

Prepared by Procedure B in 45% yield. LC/MS (EI) $t_R$ 4.50 min, m/z 367 (M$^+$+1).

Example 127

N-(8-Methyl-8-azabicyclo[3.2.1]oct-3-yl)-6-(5-methyl-2-thienyl)-1H-indazole-3-carboxamide hydroformate

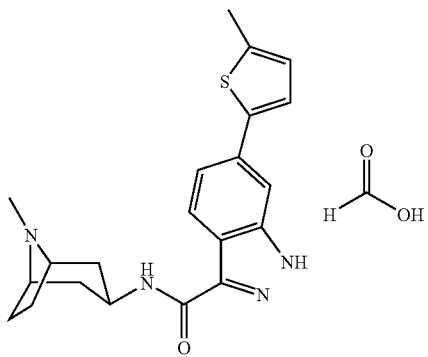

Prepared by Procedure B in 4% yield. LC/MS (EI) $t_R$ 5.54 min, m/z 381 (M$^+$+1).

Example 128

N-(8-Methyl-8-azabicyclo[3.2.1]oct-3-yl)-6-[(3-trifluoromethyl)phenyl]-1H-indazole-3-carboxamide hydroformate

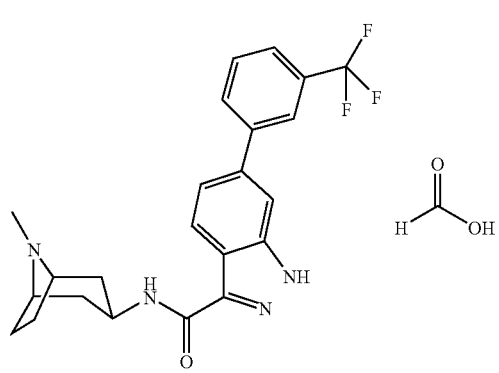

Prepared by Procedure B in 4% yield. LC/MS (EI) $t_R$ 5.10 min, m/z 429 (M$^+$+1).

Example 129

N-(8-Methyl-8-azabicyclo[3.2.1]oct-3-yl)-6-[(3-trifluoromethyl)phenyl]-1H-indazole-3-carboxamide

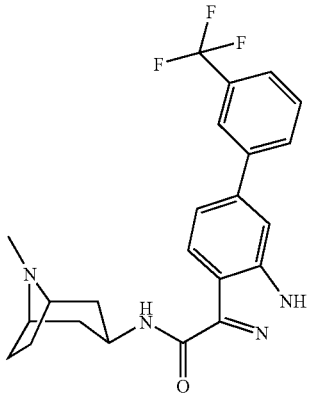

Prepared by Procedure B in 4% yield. LC/MS (EI) $t_R$ 5.00 min, m/z 429 (M$^+$+1).

Example 130

N-(8-Methyl-8-azabicyclo[3.2.1]oct-3-yl)-6-[(4-trifluoromethyl)phenyl]-1H-indazole-3-carboxamide hydroformate

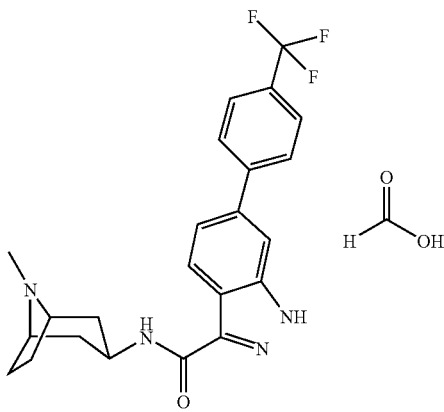

Prepared by Procedure B in 3% yield. LC/MS (EI) $t_R$ 5.08 min, m/z 429 (M$^+$+1).

Example 131

N-(8-Methyl-8-azabicyclo[3.2.1]oct-3-yl)-6-[(4-trifluoromethyl)phenyl]-1H-indazole-3-carboxamide

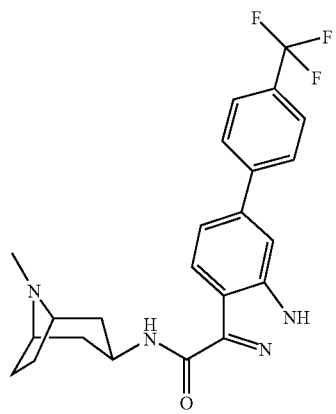

Prepared by Procedure B in 3% yield. LC/MS (EI) $t_R$ 5.10 min, m/z 429 (M$^+$+1).

Example 132

N-(endo-9-Methyl-9-azabicyclo[3.3.1]non-3-yl)-5-(3-thienyl)-1H-indazole-3-carboxamide hydroformate

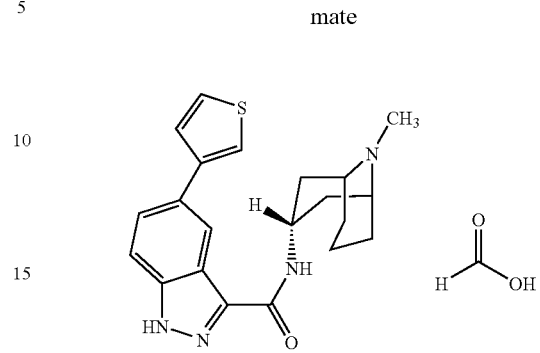

Prepared by Procedure B in 11% yield. LC/MS (EI) $t_R$ 4.60 min, m/z 381 (M$^+$+1).

Example 133

N-(endo-9-Methyl-9-azabicyclo[3.3.1]non-3-yl)-5-(4-methyl-2-thienyl)-1H-indazole-3-carboxamide hydroformate

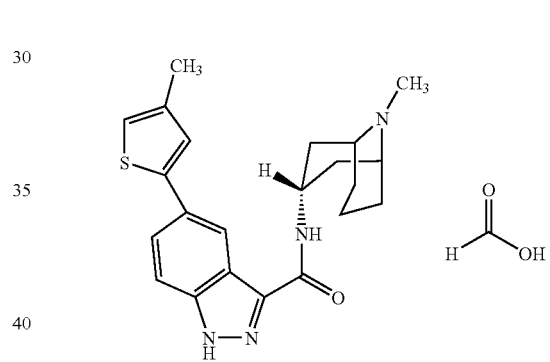

Prepared by Procedure B in 18% yield. LC/MS (EI) $t_R$ 5.62 min, m/z 395 (M$^+$+1).

Example 134

N-(endo-9-Methyl-9-azabicyclo[3.3.1]non-3-yl)-6-(2-thienyl)-1H-indazole-3-carboxamide hydroformate

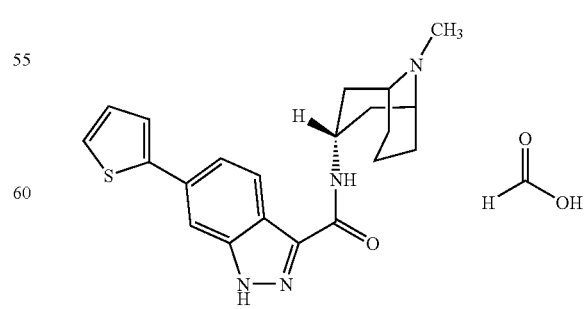

Prepared by Procedure B in 9% yield. LC/MS (EI) $t_R$ 4.02 min, m/z 381 (M$^+$+1).

Example 135

N-(endo-9-Methyl-9-azabicyclo[3.3.1]non-3-yl)-6-(4-methyl-2-thienyl)-1H-indazole-3-carboxamide hydroformate

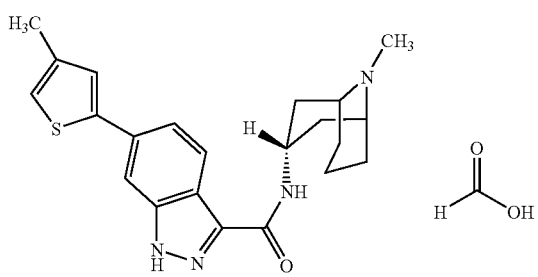

Prepared by Procedure B in 6% yield. LC/MS (EI) $t_R$ 5.66 min, m/z 395 (M$^+$+1).

Example 136

8-Methyl-N-{[5-(3-thienyl)-1H-indazol-3-yl]methyl}-8-azabicyclo[3.2.1]octan-3-amine hydroformate

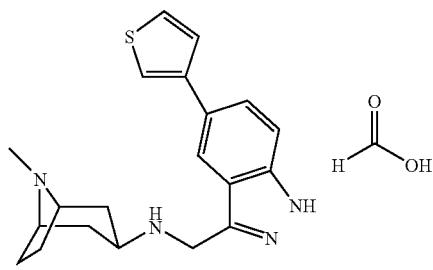

Prepared by Procedure B, followed by lithium aluminum hydride reduction, in 8% yield. LC/MS (EI) $t_R$ 2.55 min, m/z 353 (M$^+$+1).

Example 137

N-(8-Methyl-8-azabicyclo[3.2.1]oct-3-yl)-5-(3-thienyl)-1H-indazole-3-carbothioamide hydroformate

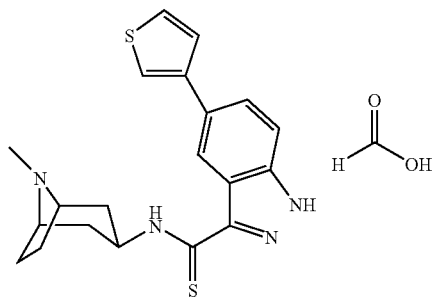

Prepared by Procedure B, followed by reaction with Lawesson's reagent, in 6% yield. LC/MS (EI) $t_R$ 5.75 min, m/z 383 (M$^+$+1).

Representative Procedure C.

Procedure C provides a method for the coupling between brominated bicyclobase carboxamides and zinc reagents to form aryl-substituted derivatives.

Example 138

N-(endo-9-Methyl-9-azabicyclo[3.3.1]non-3-yl)-5-(1,3-thiazol-2-yl)-1H-indazole-3-carboxamide hydroformate

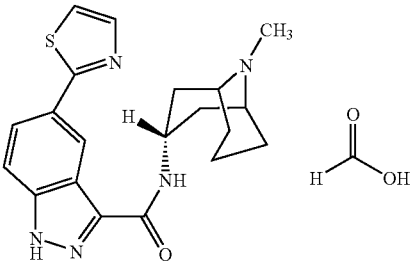

In a 10 mL microwave reaction vessel was added 5-bromo-N-(endo-9-methyl-9-azabicyclo[3.3.1]non-3-yl)-1H-indazole-3-carboxamide (0.8 mmol) and palladium tetrakistriphenylphosphine (0.16 mmol). The vessel was evacuated, backfilled with argon gas, and the contents diluted with a 0.5 M tetrahydrofuran solution of 2-thiazolylzinc bromide (6.4 mL). The vessel was sealed and subjected to microwave irradiation at 100° C. for 3600 s. The reaction was quenched with acetic acid (1 mL) and was loaded on a 10 g SCX column. The column was washed with methanol (50 mL) and the product was eluted with 2 M ammonia in methanol (50 mL) and concentrated. The residue was purified by chromatography [1/1 to 0/1 ethyl acetate/(70/30/1 ethyl acetate/methanol/triethylamine)] followed by preparative HPLC, thus providing the product in 6% yield. $^1$H NMR (CD$_3$OD) δ 8.8 (s, 1 H), 8.5 (s, 1 H), 8.1 (d, J=8.9, 1 H), 7.9 (d, J=2.8, 1 H), 7.7 (d, J=8.7, 1 H), 7.6 (d, J=2.8, 1 H), 4.6 (m, 1 H), 3.68 (app d, J=8.7, 1 H), 2.9 (s, 3 H), 2.7-2.5 (m, 2 H), 2.2 (m, 4 H), 2.0 (app t, J=24.8, 2 H), 1.7-1.6 (m, 2 H); LC/MS (EI) $t_R$ 4.82 min, m/z 382 (M$^+$+1).

Using this general procedure the following compounds were prepared:

Example 139

6-Cyclopropyl-N-(8-methyl-8-azabicyclo[3.2.1]oct-3-yl)-1,2-benzisothiazole-3-carboxamide hydroformate

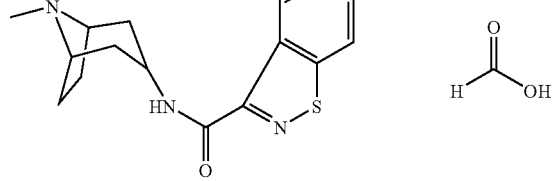

Prepared by Procedure C in 42% yield. LC/MS (EI) $t_R$ 4.18 min, m/z 342 (M$^+$+1).

Example 140

N-(8-Methyl-8-azabicyclo[3.2.1]oct-3-yl)-5-(1,3-thiazol-2-yl)-1H-indazole-3-carboxamide hydroformate

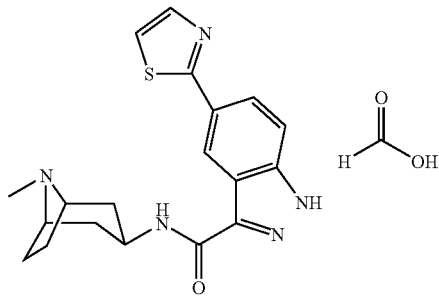

Prepared by Procedure C in 2% yield. LC/MS (EI) $t_R$ 4.05 min, m/z 368 (M$^+$+1).

Example 141

N-(8-Methyl-8-azabicyclo[3.2.1]oct-3-yl)-5-(1-methyl-1H-imidazol-2-yl)-1H-indazole-3-carboxamide hydroformate

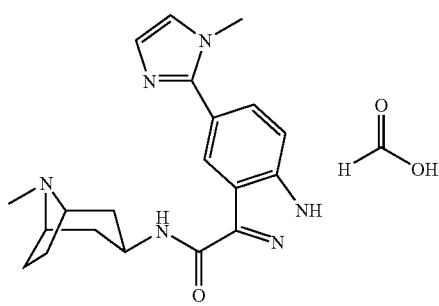

Prepared by Procedure C in 40% yield. LC/MS (EI) $t_R$ 1.19 min, m/z 365 (M$^+$+1).

Example 142

N-(8-Methyl-8-azabicyclo[3.2.1]oct-3-yl)-6-(1,3-oxazol-2-yl)-1H-indazole-3-carboxamide hydroformate

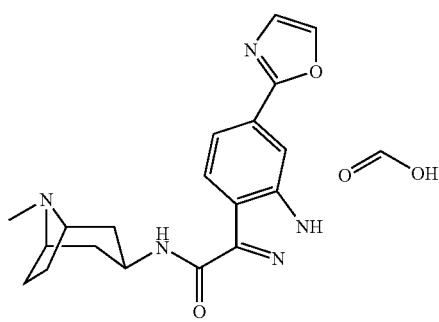

Prepared by Procedure C in 1% yield. LC/MS (EI) $t_R$ 3 min, m/z 352 (M$^+$+1).

Example 143

N-(8-Methyl-8-azabicyclo[3.2.1]oct-3-yl)-6-(1,3-thiazol-2-yl)-1H-indazole-3-carboxamide

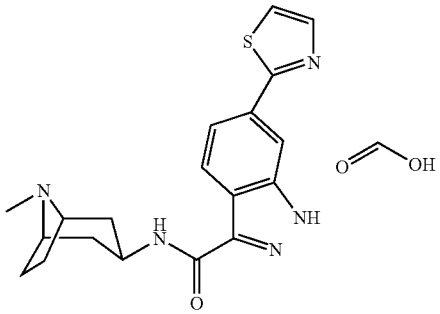

Prepared by Procedure C in 5% yield. LC/MS (EI) $t_R$ 3.76 min, m/z 368 (M$^+$+1).

Example 144

N-(8-Methyl-8-azabicyclo[3.2.1]oct-3-yl)-6-(1,3-thiazol-2-yl)-1H-indazole-3-carboxamide hydroformate

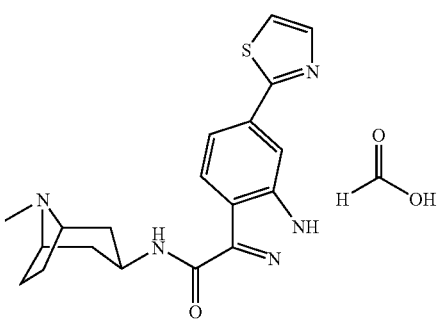

Prepared by Procedure C in 5% yield. LC/MS (EI) $t_R$ 3.67 min, m/z 368 (M$^+$+1).

Example 145

N-(8-Methyl-8-azabicyclo[3.2.1]oct-3-yl)-6-(1-methyl-1H-imidazol-2-yl)-1H-indazole-3-carboxamide dihydrochloride

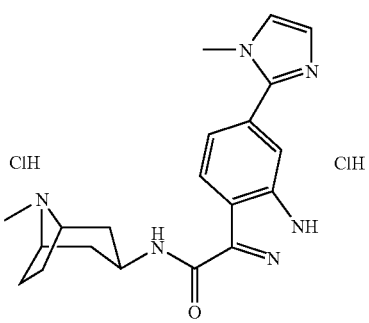

Prepared by Procedure C in 53% yield. LC/MS (EI) $t_R$ 1.41 min, m/z 365 (M$^+$+1).

Example 146

N-(8-Methyl-8-azabicyclo[3.2.1]oct-3-yl)-6-(4-methyl-1,3-thiazol-2-yl)-1H-indazole-3-carboxamide hydroformate

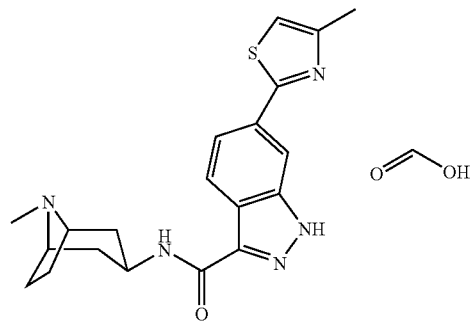

Prepared by Procedure C in 1% yield. LC/MS (EI) $t_R$ 4.74 min, m/z 382 (M$^+$+1).

Example 147

N-(8-Methyl-8-azabicyclo[3.2.1]oct-3-yl)-6-(5-methyl-1,3-thiazol-2-yl)-1H-indazole-3-carboxamide hydroformate

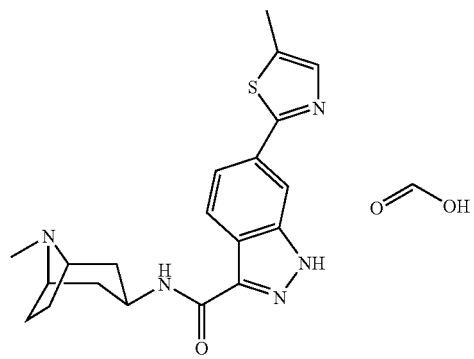

Prepared by Procedure C in 7% yield. LC/MS (EI) $t_R$ 4.48 min, m/z 382 (M$^+$+1).

Example 148

N-(endo-9-Methyl-9-azabicyclo[3.3.1]non-3-yl)-5-(1,3-oxazol-2-yl)-1H-indazole-3-carboxamide hydroformate

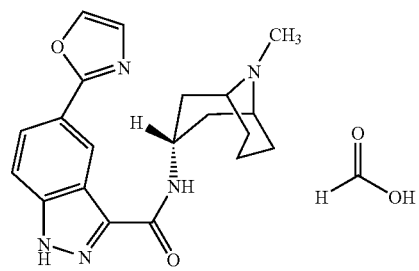

Prepared by Procedure C in 29% yield. LC/MS (EI) $t_R$ 4.21 min, m/z 366 (M$^+$+1).

Example 149

N-(endo-9-Methyl-9-azabicyclo[3.3.1]non-3-yl)-5-(1-methyl-1H-imidazol-2-yl)-1H-indazole-3-carboxamide dihydroformate

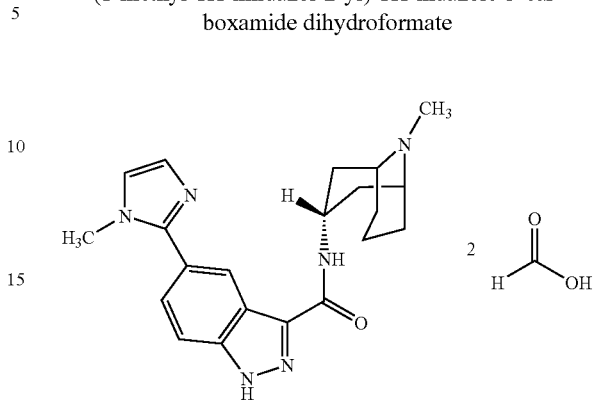

Prepared by Procedure C in 64% yield. LC/MS (EI) $t_R$ 1.18 min, m/z 379 (M$^+$+1).

Example 150

N-(endo-9-Methyl-9-azabicyclo[3.3.1]non-3-yl)-6-(1,3-thiazol-2-yl)-1H-indazole-3-carboxamide hydroformate

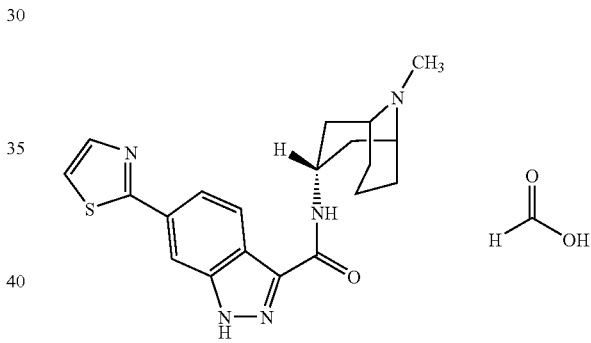

Prepared by Procedure C in 3% yield. LC/MS (EI) $t_R$ 4.86 min, m/z 382 (M$^+$+1).

Example 151

N-(endo-8-Methyl-8-azabicyclo[3.2.1]oct-3-yl)-5-(1,3-thiazol-2-yl)-1H-indazole-3-carboxamide hydroformate

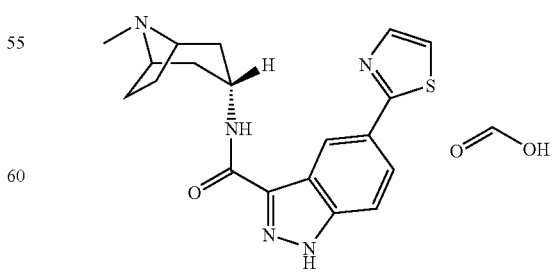

Prepared by Procedure C in 8% yield. LC/MS (EI) $t_R$ 4.39 min, m/z 368 (M$^+$+1).

Example 152

N-(endo-8-Methyl-8-azabicyclo[3.2.1]oct-3-yl)-6-(1,3-oxazol-2-yl)-1H-indazole-3-carboxamide hydroformate

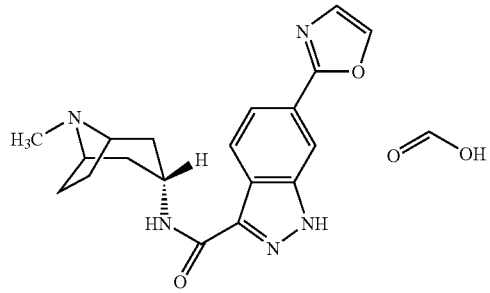

Prepared by Procedure C in 5% yield. LC/MS (EI) $t_R$ 2.54 min, m/z 352 (M$^+$+1).

Example 153

N-(endo-8-Methyl-8-azabicyclo[3.2.1]oct-3-yl)-6-(4-methyl-1,3-thiazol-2-yl)-1H-indazole-3-carboxamide hydroformate

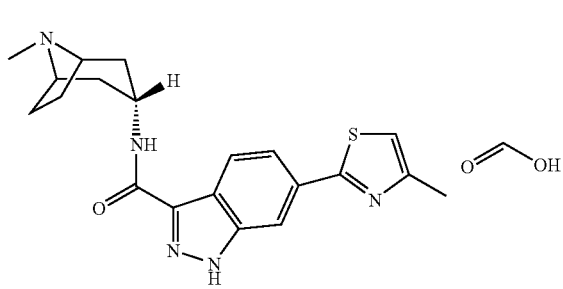

Prepared by Procedure C in 8% yield. LC/MS (EI) $t_R$ 5.03 min, m/z 382 (M$^+$+1).

Example 154

N-(endo-8-Methyl-8-azabicyclo[3.2.1]oct-3-yl)-6-(5-methyl-1,3-thiazol-2-yl)-1H-indazole-3-carboxamide hydroformate

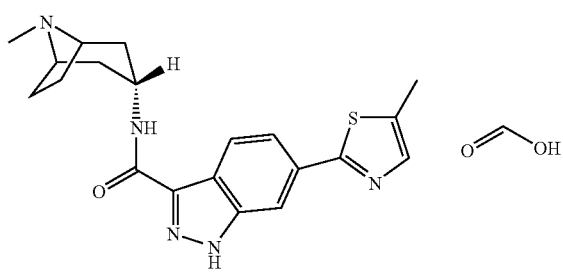

Prepared by Procedure C in 7% yield. LC/MS (EI) $t_R$ 4.66 min, m/z 382 (M$^+$+1).

Example 155

N-(exo-8-Methyl-8-azabicyclo[3.2.1]oct-3-yl)-5-(1,3-thiazol-2-yl)-1H-indazole-3-carboxamide hydroformate

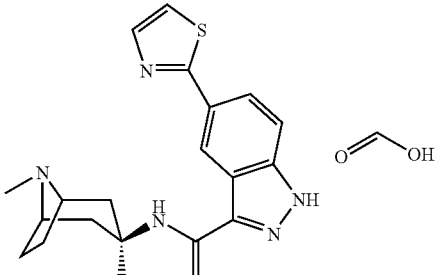

Prepared by Procedure C in 1% yield. LC/MS (ED $t_R$ 4.26 min, m/z 368 (M$^+$+1).

Example 156

N-(exo-8-Methyl-8-azabicyclo[3.2.1]oct-3-yl)-6-(1,3-oxazol-2-yl)-1H-indazole-3-carboxamide hydroformate

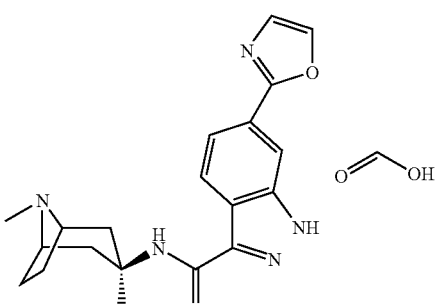

Prepared by Procedure C in 1% yield. LC/MS (EI) $t_R$ 2.9 min, m/z 352 (M$^+$+1).

Example 157

N-(exo-8-Methyl-8-azabicyclo[3.2.1]oct-3-yl)-6-(4-methyl-1,3-thiazol-2-yl)-1H-indazole-3-carboxamide hydroformate

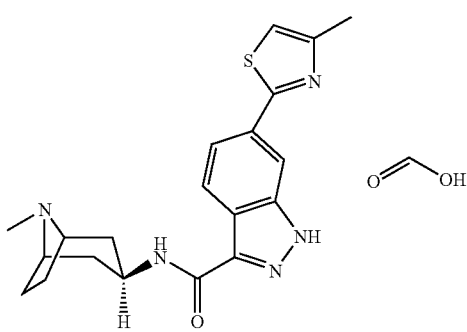

Prepared by Procedure C in 8% yield. LC/MS (EI) $t_R$ 5.05 min, m/z 382 (M$^+$+1).

Example 158

N-(exo-8-Methyl-8-azabicyclo[3.2.1]oct-3-yl)-6-(5-methyl-1,3-thiazol-2-yl)-1H-indazole-3-carboxamide hydroformate

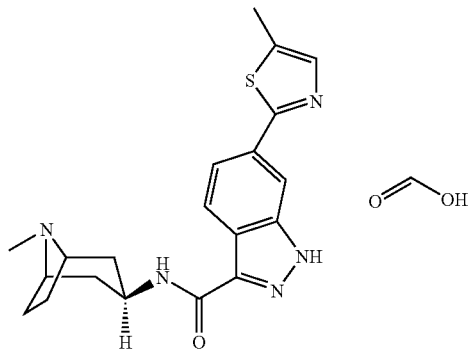

Prepared by Procedure C in 2% yield. LC/MS (EI) $t_R$ 4.54 min, m/z 382 (M$^+$+1).

Representative Procedure D.

Procedure D provides a method for the coupling between bicyclobase carboxamides and carboxaldehydes to form tertiary amine derivatives.

Example 159

N-(2-Cyclopropylmethyl-2-azabicyclo[2.2.1]hept-5-yl)-1H-indazole-3-carboxamide hydroformate

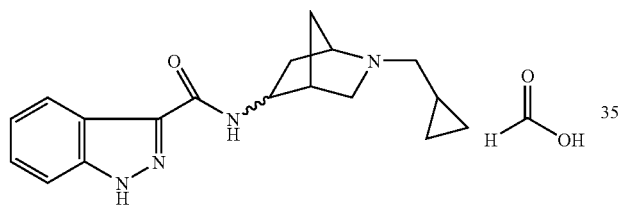

To the suspension of N-(2-azabicyclo[2.2.1]hept-5-yl)-1H-indazole-3-carboxamide hydrochloride (0.36 mmol), cyclopropylcarboxaldehyde (0.9 mmol), and N,N-diisopropylethylamine (1.08 mmol), acetic acid (0.43 mmol) was added sodium triacetoxyborohydride (0.61 mmol). The reaction mixture was maintained at rt for 2 h and was poured into water, extracted with 95/5 dichloromethane/methanol (2×30 mL), and the combined extracts were concentrated. The residue was purified by preparative HPLC, thus providing the product in 50% yield. $^1$H NMR (CD$_3$OD) δ 8.21 (m, 1 H), 7.59 (m, 1 H), 7.45 (m, 1 H), 7.26 (m, 1 H), 4.15 (m, 1 H), 3.83 (m, 1 H), 3.10 (m, 3 H), 2.02 (m, 4 H), 1.37 (m, 2 H), 0.74 (m, 2 H), 0.48 (m, 2 H); LC/MS (EI) $t_R$ 2.72 min, m/z 311 (M$^+$+1).

Using this general procedure the following compounds were prepared:

Example 160

N-(2-Ethyl-2-azabicyclo[2.2.1]hept-5-yl)-1H-indazole-3-carboxamide hydroformate

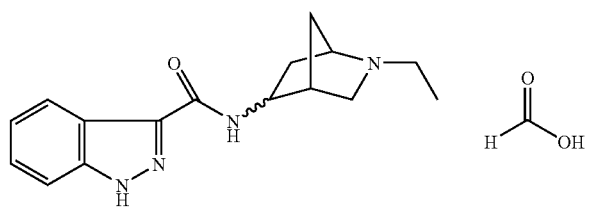

Prepared by Procedure D in 60% yield. LC/MS (EI) $t_R$ 2.76 min, m/z 285 (M$^+$+1).

Example 161

N-(2-Methyl-2-azabicyclo[2.2.1]hept-5-yl)-1H-indazole-3-carboxamide hydroformate

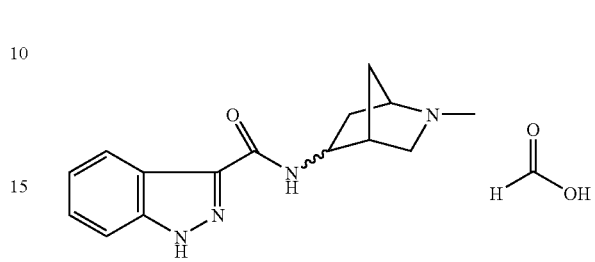

Prepared by Procedure D in 62% yield. LC/MS (EI) $t_R$ 2.67 min, m/z 271 (M$^+$+1).

Representative Procedure E.

Procedure E provides a method for the coupling between brominated bicyclobase carboxamides and acetylenes to form alkynyl-substituted derivatives.

Example 162

N-(8-Methyl-8-azabicyclo[3.2.1]oct-3-yl)-5-(2-trimethylsilylethynyl)-1H-indazole-3-carboxamide

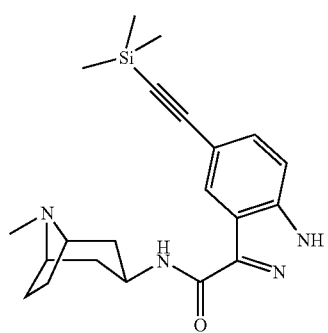

A 5 mL microwave reaction vessel was charged with bis(triphenylphosphine)palladium (II) chloride (0.0597 mmol), copper (I) iodide (0.0719 mmol), triphenylphosphine (0.124 mmol), and the bromide (0.578 mmol). The vessel was evacuated and back-filled with argon gas. The alkyne (0.71 mmol), diethylamine (3.5 mL), and N,N-dimethylformamide (1.5 mL) were added and the vessel was sealed and subjected to microwave irradiation at 120° C. for 1500 sec. The reaction was reduced under vacuum to ~1.5 mL and was transferred to a SCX column. The column was washed with methanol (50 mL) and the product was eluted with 2 M ammonia in methanol (50 mL) and concentrated. The residue was purified by chromatography [1/1 to 0/1 ethyl acetate/(70/30/1 ethyl acetate/methanol/ammonium hydroxide)] to provide the silylacetylene in 24% yield. LC/MS (EI) $t_R$ 5.46 min, m/z 381 (M$^+$+1).

Using this general procedure the following compounds were prepared:

Example 163

5-Ethynyl-N-(8-methyl-8-azabicyclo[3.2.1]oct-3-yl)-1H-indazole-3-carboxamide

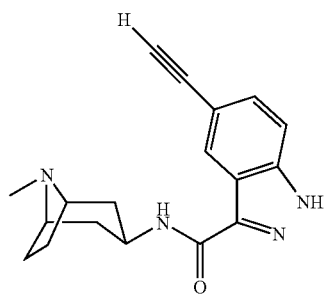

The silane (see example 163) was dissolved in tetrahydrofuran (2.5 mL) and was treated with tetrabutylammonium fluoride (0.6 mL of a 1 M solution in tetrahydrofuran). The reaction mixture was maintained for 11 h and was transferred to a SCX column. The column was washed with methanol (50 mL) and the product was eluted with 2 M ammonia in methanol (50 mL) and concentrated. The residue was purified by preparative HPLC, thus providing the product in 4% yield. $^1$H NMR (CD$_3$OD) δ 8.35 (s, 1 H), 7.58 (d, J=8.7, 1.5, 1 H), 7.49 (dd, J=8.7, 1 H), 4.21 (m, 1 H), 3.47 (m, 3 H), 2.51 (s, 3 H), 2.36-2.01 (m, 8 H); LC/MS (EI) $t_R$ 3.51 min, m/z 309 (M$^+$+1).

Example 164

N-(8-Methyl-8-azabicyclo[3.2.1]oct-3-yl)-6-(2-trimethylsilylethyn-1-yl)-1H-indazole-3-carboxamide hydroformate

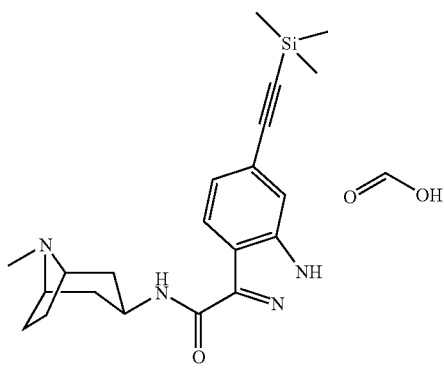

Prepared by Procedure E in 49% yield. LC/MS (EI) $t_R$ 5.45 min, m/z 381 (M$^+$+1).

Example 165

N-(endo-9-Methyl-9-azabicyclo[3.3.1]non-3-yl)-5-(2-trimethylsilylethyn-1-yl)-1H-indazole-3-carboxamide

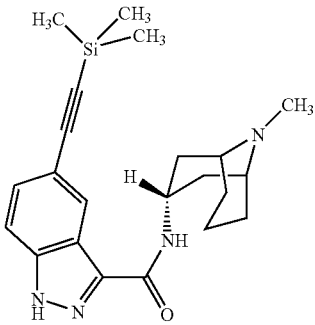

Prepared by Procedure E in 6% yield. LC/MS (EI) $t_R$ 5.53 min, m/z 395 (M$^+$+1).

Representative Procedure F.

Procedure F provides a method for the coupling between brominated bicyclobase carboxamides and nickel (II) cyanide to form cyano-substituted derivatives.

Example 166

5-Cyano-N-(8-methyl-8-azabicyclo[3.2.1]oct-3-yl)-1H-indazole-3-carboxamide hydroformate

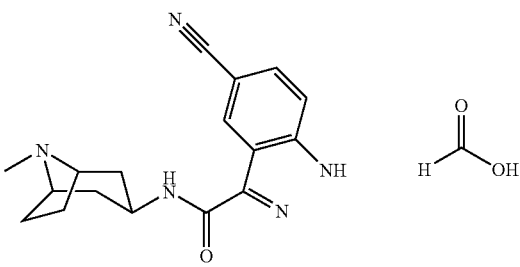

A 5 mL microwave reaction vessel was charged with nickel (II) cyanide (3.11 mmol) and the bromide (0.578 mmol). The vessel was evacuated, back-filled with argon gas, and diluted with N-methylpyrrolidinone (5.0 mL). The vessel was sealed and subjected to microwave irradiation at 200° C. for 2400 sec. The reaction was transferred to a SCX column and the column was washed with methanol (50 mL). The product was eluted with 2 M ammonia in methanol (50 mL) and concentrated. The residue was purified by preparative HPLC, thus providing the product in 4% yield. $^1$H NMR (CD$_3$OD) δ 8.65 (s, 1 H), 8.52 (s, 1 H), 7.80-7.69 (m, 2 H), 3.92 (s, 1 H), 2.83 (s, 3 H), 2.43-2.02 (m, 8 H); LC/MS (EI) $t_R$ 2.65 min, m/z 310 (M$^+$+1).

Using this general procedure the following compounds were prepared:

Example 167

6-Cyano-N-(8-methyl-8-azabicyclo[3.2.1]oct-3-yl)-1H-indazole-3-carboxamide hydroformate

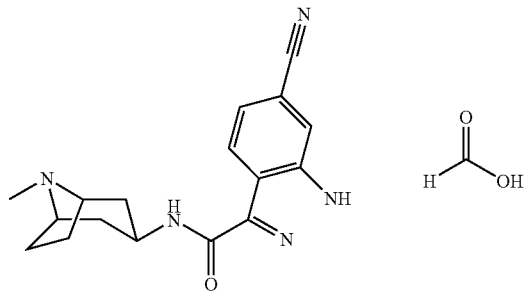

Prepared by Procedure F in 16% yield. LC/MS (EI) $t_R$ 2.63 min, m/z 310 (M$^+$+1).

Representative Procedure G.

Procedure G provides a method for the coupling between brominated bicyclobase carboxamides and cyclic, secondary amines to form amino-substituted derivatives.

Example 168

N-(8-Methyl-8-azabicyclo[3.2.1]oct-3-yl)-5-(pyrrolidin-1-yl)-1H-indazole-3-carboxamide hydroformate

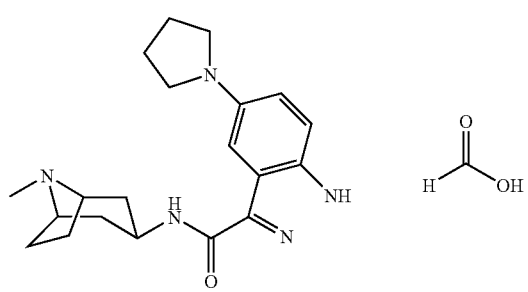

A 2.5 mL microwave reaction vessel was charged with tris(dibenzylideneacetone)dipalladium (0) (0.060 mmol), [2'-(dimethylamino)biphenyl-2-yl]dicyclohexylphosphine (0.060 mmol), and the bromide (0.550 mmol). The vessel was evacuated and back-filled with argon gas. The amine (0.66 mmol) and a 1 M solution of lithium hexamethyldisilazide in tetrahydrofuran (1.7 mmol) were added and the vessel was sealed and heated at 65° C. for 15 h. The reaction was transferred to a SCX column and the column was washed with methanol (50 mL). The product was eluted with 2 M ammonia in methanol (50 mL) and concentrated. The residue was purified by preparative HPLC, thus providing the product in 35% yield. $^1$H NMR (CD$_3$OD) δ 8.36 (s, 1 H), 7.46 (d, J=9.0, 1 H), 7.18 (d, J=1.8, 1 H), 7.01 (dd, J=9.0, 2.4, 1 H), 4.25 (s, 1 H), 3.94 (s, 2 H), 3.37-3.30 (m, 2 H), 2.84 (s, 3 H), 2.50-2.42 (m, 8 H), 2.08-2.04 (m, 4 H); LC/MS (EI) $t_R$ 2.42 min, m/z 354 (M$^+$+1).

Using this general procedure the following compounds were prepared:

Example 169

N-(8-Methyl-8-azabicyclo[3.2.1]oct-3-yl)-5-(morpholin-4-yl)-1H-indazole-3-carboxamide hydroformate

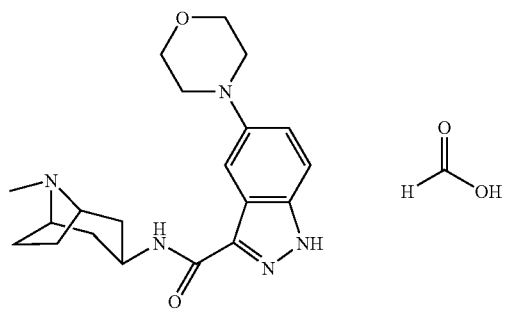

Prepared by Procedure G in 40% yield. LC/MS (EI) $t_R$ 2.39 min, m/z 370 (M$^+$+1).

Example 170

N-(8-Methyl-8-azabicyclo[3.2.1]oct-3-yl)-5-(thiomorpholin-4-yl)-1H-indazole-3-carboxamide hydroformate

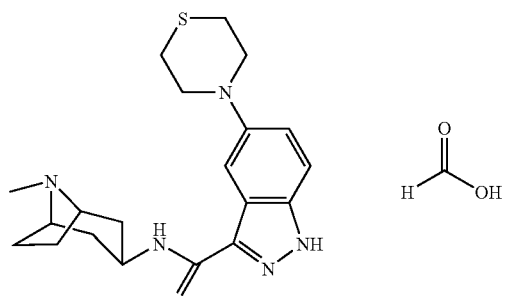

Prepared by Procedure G in 40% yield. LC/MS (EI) $t_R$ 2.40 min, m/z 386 (M$^+$+1).

Example 171

N-(endo-9-Methyl-9-azabicyclo[3.3.1]non-3-yl)-5-(morpholin-4-yl)-1H-indazole-3-carboxamide hydroformate

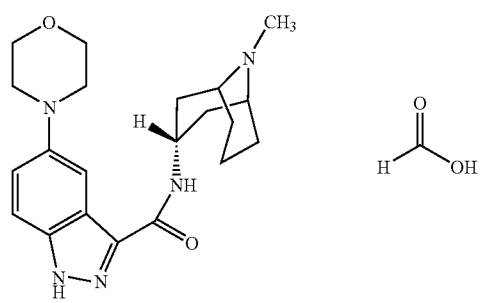

Prepared by Procedure G in 15% yield. LC/MS (EI) $t_R$ 2.36 min, m/z 384 (M$^+$+1).

Example 172

N-(endo-9-Methyl-9-azabicyclo[3.3.1]non-3-yl)-5-(pyrrolidin-1-yl)-1H-indazole-3-carboxamide hydroformate

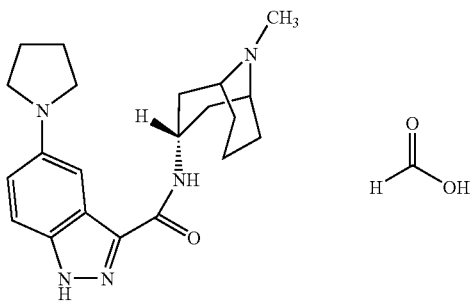

Prepared by Procedure G in 23% yield. LC/MS (EI) $t_R$ 2.40 min, m/z 368 (M$^+$+1).

Example 173

N-(endo-9-Methyl-9-azabicyclo[3.3.1]non-3-yl)-5-(thiomorpholin-4-yl)-1H-indazole-3-carboxamide hydroformate

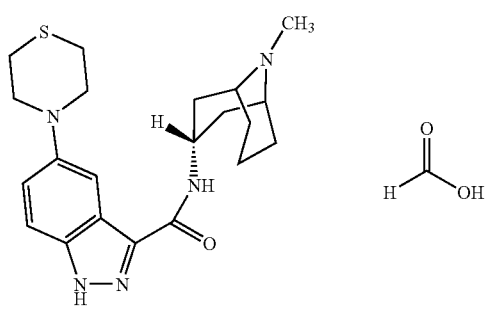

Prepared by Procedure G in 13% yield. LC/MS (EI) $t_R$ 2.37 min, m/z 400 (M$^+$+1).

Representative Procedure H.

Procedure H provides a method for the reduction of nitro bicyclobase carboxamides to form aniline derivatives.

Example 174

5-Amino-N-(8-methyl-8-azabicyclo[3.2.1]oct-3-yl)-1H-indazole-3-carboxamide hydroformate

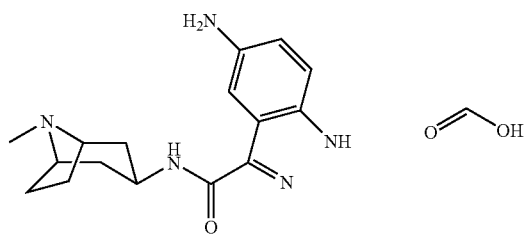

A mixture of the 5-nitro compound (11 mg, 0.03 mmol) and 10% palladium on carbon (11 mg) was diluted with methanol (300 mL). The reaction vessel was evacuated and the reaction mixture was maintained under an atmosphere of hydrogen gas for 12 h. The catalyst was removed by filtration through Celite and the organic layer was concentrated. The residue was purified by preparative HPLC, thus providing the product in 23% yield. The aniline was routinely used without purification in subsequent reactions. $^1$H NMR (CD$_3$OD) δ 7.52-7.31 (m, 2 H), 7.01-6.97 (m, 1 H), 4.53 (br s, 1 H), 4.25 (br s, 1 H), 3.93 (br s, 2 H), 2.82 (s, 3 H), 2.53-1.85 (m, 8 H); LC/MS (EI) $t_R$ 1.44 min, m/z 300 (M$^+$+1).

Using this general procedure the following compounds were prepared:

Example 175

5-Amino-N-(endo-9-methyl-9-azabicyclo[3.3.1]non-3-yl)-1H-indazole-3-carboxamide hydroformate

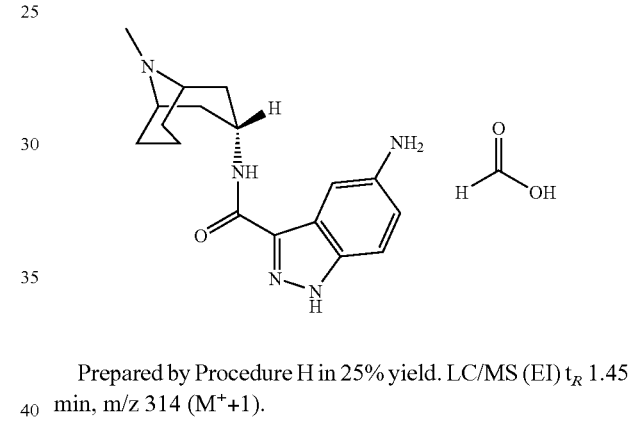

Prepared by Procedure H in 25% yield. LC/MS (EI) $t_R$ 1.45 min, m/z 314 (M$^+$+1).

Example 176

6-Amino-N-(2-methyl-2-azabicyclo[2.2.1]hept-5-yl)-1H-indazole-3-carboxamide

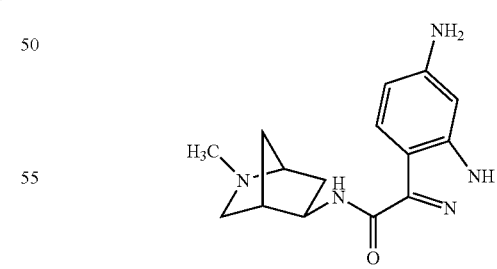

Prepared by Procedure H in 95% yield. LC/MS (EI) $t_R$ 1.55 min, m/z 286 (M$^+$+1).

Representative Procedure I.

Procedure I provides a method for the reaction of alkynyl bicyclobase carboxamides with azides to form triazole derivatives.

Example 177

N-(endo-8-Methyl-8-azabicyclo[3.2.1]oct-3-yl)-6-[1-(2-piperidin-1-ylethyl)-1H-1,2,3-triazol-4-yl]-1H-indazole-3-carboxamide trihydroformate

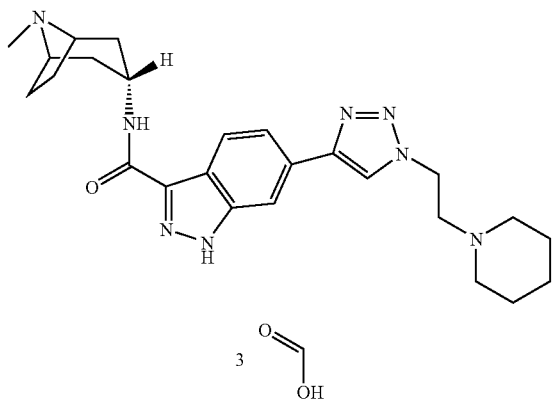

3-[(5-Ethynyl-1H-indazol-3-yl)carbonyl]amino-8-methyl-8-azabicyclo[3.2.1]octane hydroformate (50 mg, 0.10 mmol) and 2-(1-piperidinyl)ethylazide (20 mg, 0.10 mmol) were suspended in water (0.3 mL) and tert-butyl alcohol (0.3 mL). Sodium ascorbate (10 mg, 0.070 mmol) was added followed by a solution of copper(II) sulfate pentahydrate (4 mg, 0.01 mmol) in water (10 mL). The reaction mixture was stirred vigorously for 12 h, and was concentrated. The residue was purified by preparative HPLC, thus providing the product in 9% yield. $^1$H NMR (CD$_3$OD) δ 8.68 (s, 1 H), 8.45 (s, 1 H), 8.35 (s, 2 H), 7.96 (app d, J=8.7, 1 H), 7.70 (app d, J=8.7, 1 H), 4.57 (br s, 1 H), 3.85 (t, J=11.2, 1 H), 3.48 (br s, 4 H), 3.39-3.37 (m, 2 H), 3.07 (br s, 4 H), 2.66-1.62 (m, 13 H); LC/MS (EI) $t_R$ 4.15 min, m/z 485 (M$^+$+Na).

Using this general procedure the following compounds were prepared:

Example 178

Ethyl [4-(3-{[(8-methyl-8-azabicyclo[3.2.1]oct-3-yl)amino]carbonyl}-1H-indazol-6-yl)-1H-1,2,3-triazol-1-yl]acetate dihydroformate

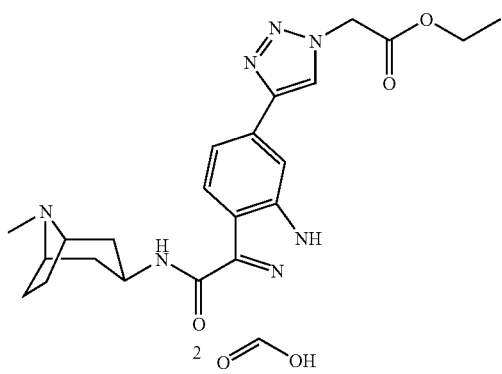

Prepared by Procedure I in 70% yield. LC/MS (EI) $t_R$ 3.57 min, m/z 438 (M$^+$+1).

Example 179

5-(1-Benzyl-1H-1,2,3-triazol-4-yl)-N-(8-methyl-8-azabicyclo[3.2.1]oct-3-yl)-1H-indazole-3-carboxamide dihydroformate

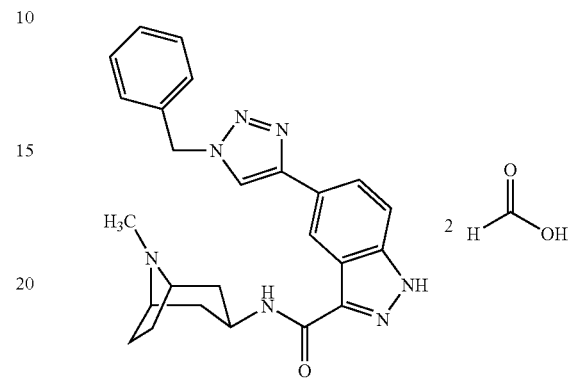

Prepared by Procedure I in 17% yield. LC/MS (EI) $t_R$ 5.76 min, m/z 442 (M$^+$+1).

Example 180

5-(1-Benzyl-1H-1,2,3-triazol-4-yl)-N-(endo-8-methyl-8-azabicyclo[3.2.1]oct-3-yl)-1H-indazole-3-carboxamide dihydroformate

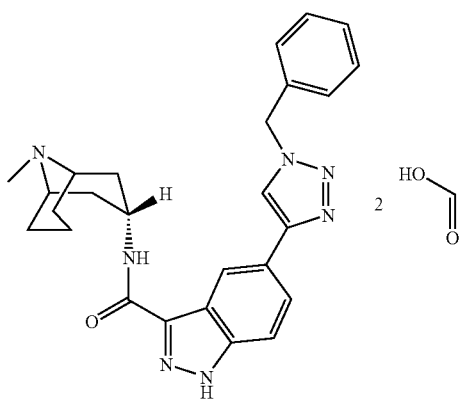

Prepared by Procedure I in 10% yield. LC/MS (EI) $t_R$ 5.76 min, m/z 442 (M$^+$+1).

Representative Procedure J.

Procedure J provides a method for the coupling between amino bicyclobase carboxamides and isocyanates to form urea derivatives.

Example 181

5-{[(Cyclopentylamino)carbonyl]amino}-N-(endo-8-methyl-8-azabicyclo[3.2.1]oct-3-yl)-1H-indazole-3-carboxamide hydroformate

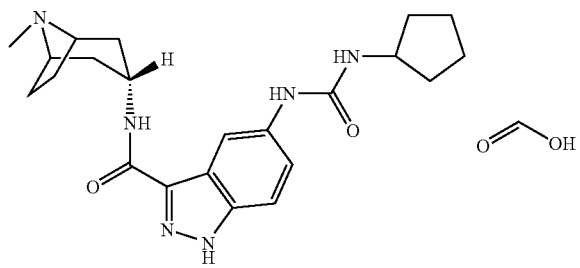

Cyclopentyl isocyanate (48 mg, 0.43 mmol) was added to a solution of 5-amino-N-(8-methyl-8-azabicyclo[3.2.1]oct-3-yl)-1H-indazole-3-carboxamide (100 mg, 0.30 mmol) in pyridine (3 mL) and N,N-dimethylformamide (2 mL). The reaction mixture was maintained for 16 h and was concentrated. The residue was purified by preparative HPLC, thus providing the product in 30% yield. $^1$H NMR (CD$_3$OD) δ 8.50 (s, 1 H), 8.13 (s, 1 H), 7.51 (s, 2 H), 4.62 (br s, 1 H), 4.24 (br s, 1 H), 4.07 (qt, J=13.2, 6.5, 1 H), 3.92 (s, 2 H), 2.83 (s, 3 H), 2.49-2.36 (m, 8 H), 2.01-1.45 (m, 8 H); LC/MS (EI) t$_R$ 4.53 min, m/z 411 (M$^+$+1).

Using this general procedure the following compounds were prepared:

Example 182

N-(endo-8-Methyl-8-azabicyclo[3.2.1]oct-3-yl)-5-{[(propylamino)carbonyl]amino}-1H-indazole-3-carboxamide hydroformate

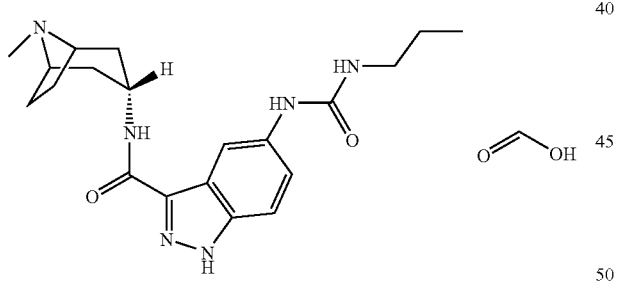

Prepared by Procedure J in 20% yield. LC/MS (EI) t$_R$ 2.54 min, m/z 385 (M$^+$+1).

Example 183

6-{[(Cyclopentylamino)carbonyl]amino}-N-(endo-8-methyl-8-azabicyclo[3.2.1]oct-3-yl)-1H-indazole-3-carboxamide hydroformate

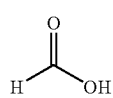

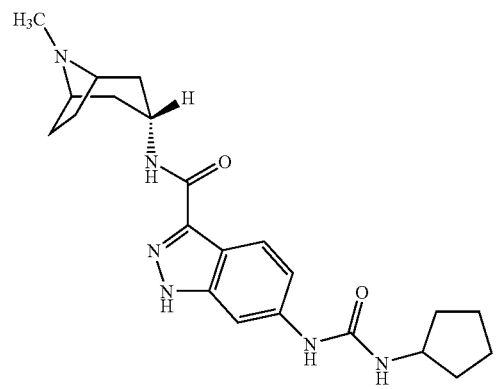

Prepared by Procedure J in 20% yield. LC/MS (EI) t$_R$ 4.84 min, m/z 411 (M$^+$+1).

Example 184

N-(endo-8-Methyl-8-azabicyclo[3.2.1]oct-3-yl)-6-{[(propylamino)carbonyl]amino}-1H-indazole-3-carboxamide hydroformate

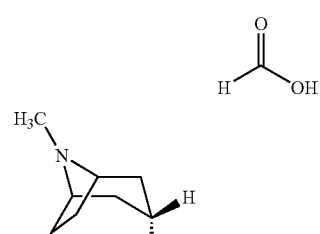

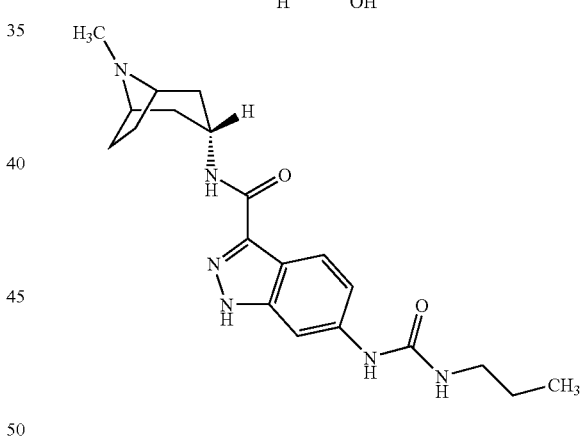

Prepared by Procedure J in 20% yield. LC/MS (EI) t$_R$ 2.81 min, m/z 385 (M$^+$+1).

Example 185

5-({[(4-Fluorophenyl)amino]carbonyl}amino)-N-(endo-8-methyl-8-azabicyclo[3.2.1]oct-3-yl)-1H-indazole-3-carboxamide hydroformate

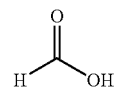

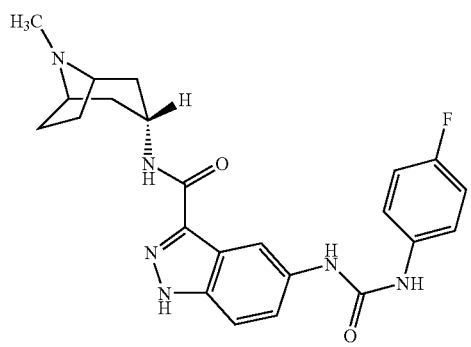

Prepared by Procedure J in 30% yield. LC/MS (EI) $t_R$ 4.07 min, m/z 437 (M$^+$+1).

Example 186

6-({[(4-Fluorobenzyl)amino]carbonyl}amino)-N-(endo-8-methyl-8-azabicyclo[3.2.1]oct-3-yl)-1H-indazole-3-carboxamide hydroformate

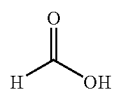

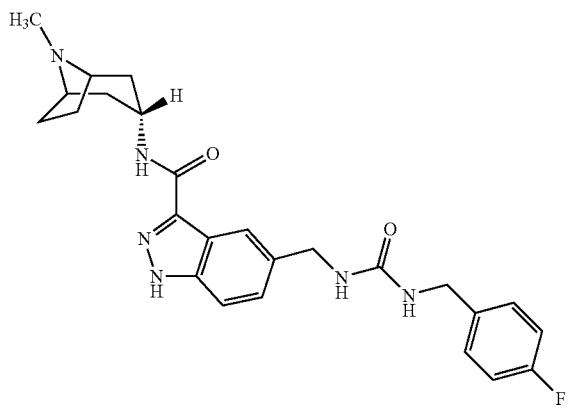

Prepared by Procedure J in 20% yield. LC/MS (EI) $t_R$ 4.8 min, m/z 451 (M$^+$+1).

Example 187

5-({[(3-Methoxyphenyl)amino]carbonyl}amino)-N-(endo-8-methyl-8-azabicyclo[3.2.1]oct-3-yl)-l1-indazole-3-carboxamide hydroformate

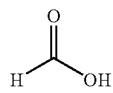

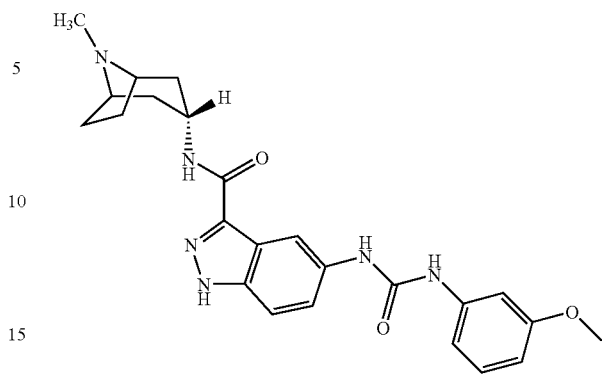

Prepared by Procedure J in 30% yield. LC/MS (EI) $t_R$ 4.25 min, m/z 449 (M$^+$+1).

Example 188

6({[(3-Methoxybenzyl)amino]carbonyl}amino)-N-(endo-8-methyl-8-azabicyclo[3.2.1]oct-3-yl)-1H-indazole-3-carboxamide hydroformate

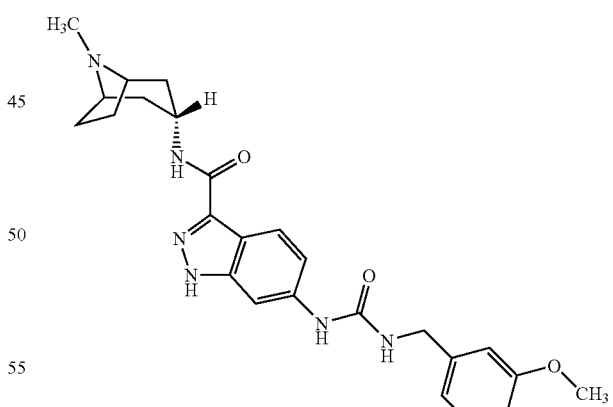

Prepared by Procedure J in 40% yield. LC/MS (EI) $t_R$ 4.7 min, m/z 463 (M$^+$+1).

Representative Procedure K.

Procedure K provides a method for the coupling between bromo bicyclobase carboxamides and thiolates and subsequent oxidation of the thio ether to form sulfone derivatives.

Example 189

N-(8-Methyl-8-azabicyclo[3.2.1]oct-3-yl)-5-(phenylthio)-1H-indazole-3-carboxamide hydroformate

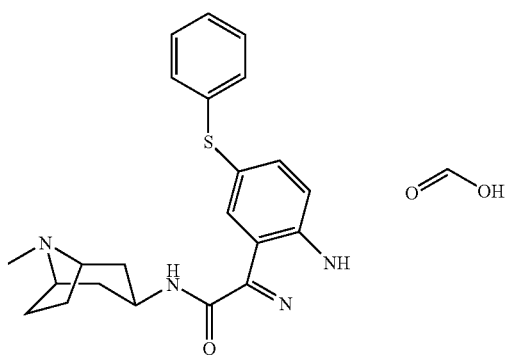

Sodium phenylthiolate (145 mg, 1.1 mmol) was added to a solution of the bromide (200 mg, 0.55 mmol) in N,N-dimethylformamide (1.7 mL). The reaction mixture was subjected to microwave irradiation at 200° C. for 1 h and was concentrated. The residue was purified by preparative HPLC to provide the phenylthio ether in 1% yield. $^1$H NMR (CD$_3$OD) δ 8.37 (br s, 1 H), 8.32 (s, 1 H), 7.61 (app d, J=8.7, 1 H), 7.46 (app dd, J=8.8, 1.6, 1 H), 7.32-7.21 (m, 5 H), 4.23 (br s, 1 H), 3.93 (s, 2H), 2.84 (s, 3 H), 2.49-2.38 (m, 8 H); LC/MS (EI) $t_R$ 4.53 min, m/z 393 (M$^+$+1).

Example 190

N-(8-Methyl-8-azabicyclo[3.2.1]oct-3-yl)-5-(phenylsulfonyl)-1H-indazole-3-carboxamide hydroformate

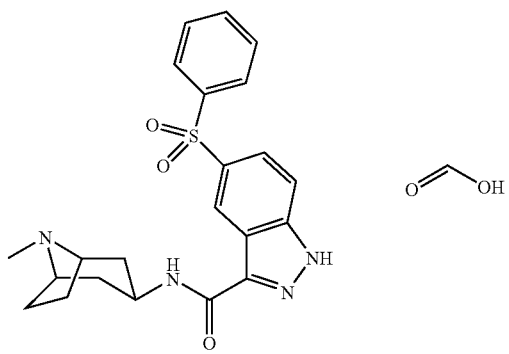

8-Methyl-3-([5-(phenylthio)-1H-indazol-3-yl]carbonylamino)-8-azabicyclo[3.2.1]octane hydroformate (example 151, 10 mg, 0.02 mmol) was diluted with a solution of oxone (40 mg, 0.07 mmol) in 1/1 methanol/water (200 mL) at 0° C. The reaction mixture was allowed to warm to rt and was maintained for 12 h. The reaction mixture was filtered and was concentrated. The residue was purified by preparative HPLC, thus providing the product in 10% yield and the N-oxide in 5% yield. $^1$H NMR (CD$_3$OD) δ 8.93 (s, 1 H), 8.55 (s, 1 H), 8.01-7.99 (m, 2 H), 7.92 (app dd, J=8.8, 1.8, 1 H), 7.8 (app d, J=8.9, 1 H), 7.63-7.55 (m, 3 H), 4.62 (br s, 1 H), 4.24 (br s, 1 H), 3.65-3.63 (m, 2 H), 2.66 (s, 3 H), 2.61 (br s, 2 H), 2.43-2.18 (m, 6 H); LC/MS (EI) $t_R$ 4.81 min, m/z 425 (M$^+$+1)

Representative Procedure L.

Procedure L provides a method for the coupling between amino bicyclobase carboxamides and isocyanates to form cyclic urea derivatives.

Example 191

N-(endo-8-methyl-8-azabicyclo[3.2.1]oct-3-yl)-5-(2-oxo-3-propylimidazolidin-1-yl)-1H-indazole-3-carboxamide hydroformate

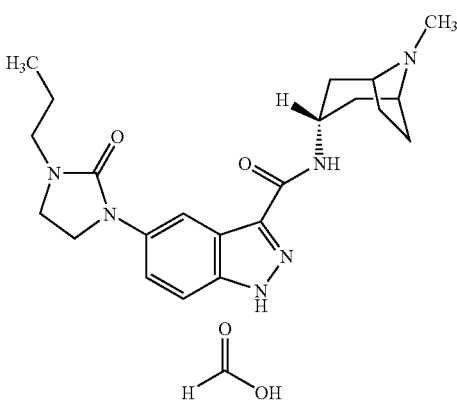

tert-Butyl (2-oxoethyl)propylcarbamate (0.140 mmol), acetic acid (0.1 mL), and sodium cyanoborohydride (0.200 mmol) was added to a solution of 5-amino-N-(8-methyl-8-azabicyclo[3.2.1]oct-3-yl)-1H-indazole-3-carboxamide (0.120 mmol) in methanol (2 mL) and the reaction mixture was maintained at rt for 16 h. The reaction was quenched with 6 M hydrogen chloride (8 mL), and the reaction mixture was stirred vigorously for 2 h and concentrated. The residue was purified by preparative HPLC to provide the amine in 65% yield as a red solid.

N,N-Carbonyldiimidazole (0.170 mmol) was added to a solution of N-(8-methyl-8-azabicyclo[3.2.1]oct-3-yl)-5-{[2-(propylamino)ethyl]amino}-1H-indazol-3-carboxamide hydroformate (0.100 mmol) in N,N-dimethylformamide (4 mL) and the reaction mixture was heated at 100° C. for 2 h. The reaction mixture was concentrated and the residue was purified by preparative HPLC to provide the cyclic urea in 60% yield as a red solid. $^1$H NMR (CD$_3$OD) 7.50-7.45 (m, 1 H), 7.24-7.19 (m, 2 H), 4.17 (s, 1.7 H), 4.04 (s, 0.3 H), 3.93 (br s, 1 H), 3.73-3.69 (m, 2 H), 3.66-3.35 (m, 4 H), 3.12 (s, 0.3 H), 3.02-2.94 (m, 3 H), 2.97 (s, 2.7 H), 2.84-2.70 (m, 1 H), 2.46-2.38 (m, 4 H), 1.77-1.70 (m, 2 H), 1.06-1.00 (m, 3 H); LC/MS (EI) $t_R$ 1.43 min, m/z 411 (M$^+$+1).

Example 192

[$^3$H] MLA Binding

Materials:
  Rat Brain: Pel-Freez Biologicals, CAT No. 56004-2
  Protease inhibitor cocktail tablet: Roche, CAT No. 1697498

Membrane Preparation

Rat brains in 20 vol (w/v) of ice-cold 0.32 M sucrose with protease inhibitors (one tablet per 50 ml,) were homogenized with a polytron for 10 sec at setting 11, then centrifuged 10 min at 1000 g, 4° C. The supernatant was centrifuged again for 20 min at 20,000 g, 4° C. The pellets were resuspended in binding buffer (200 mM TRIS-HCl, 20 mM HEPES, pH 7.5, 144 mM NaCl, 1.5 mM KCl, 1 mM MgSO$_4$, 2 mM CaCl$_2$, 0.1% (w/v) BSA) and stored membrane prep at −80° C.

For saturation assay, the 200 µl assay mixture in binding buffer contains 200 µg of membrane protein, 0.2 to 44 nM of [$^3$H] MLA. The nonspecific binding was defined using 1 µM MLA. Competition assay was carried out with 2 nM [$^3$H] MLA and a desirable range of compounds. The assay mixture was incubated at 22° C. for 2 hours, then harvested with GF/B filter presoaked with 0.3% PEI in binding buffer using Tomtec harvester. The filter was washed three time with binding buffer and the radioactivity was counted with Trilux.

Binding affinities of the preferred compounds of the invention are 292 µM to 34 nM, especially 2.5 µM to 34 nM.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention

We claim:
1. A compound according to Formula I:

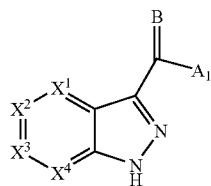

(I)

wherein
X$^1$ to X$^4$ are each, independently, CH or CR$^1$;

A$_1$ is

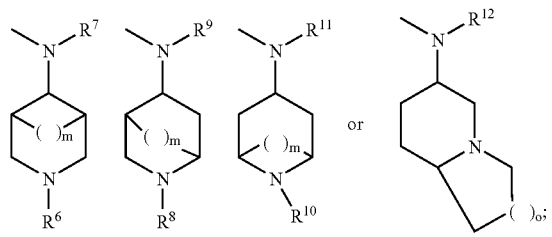

wherein when A$_1$ is of the following formula, m is 2 or 3, and B is O, then at least one of X$^1$ to X$^4$ is CR$^1$ in which R$^1$ is other than H, CH$_3$ or halogen, or R$^{10}$ is other than H, CH$_3$, or C$_2$H$_5$

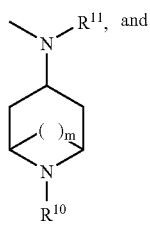

wherein when A$_1$ is of the following formula, m is 1 or 2, and B is O, then at least one of X$^1$ to X$^4$ is CR$^1$ in which R$^1$ is other than H or CH$_3$, or R$^8$ is other than H, CH$_3$, or C$_2$H$_5$

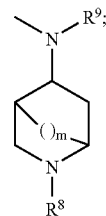

R$^1$ is
H,
C$_{1-6}$-alkyl which is unsubstituted or substituted one or more times by F, Cl, Br, I, CN, OH, alkoxy having 1 to 4 carbon atoms NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Ar, Het, or combinations thereof,
C$_{2-6}$-alkenyl which is unsubstituted or substituted one or more times by F, Cl, Br, I, CN, OH, alkoxy having 1 to 4 carbon atoms, NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Ar, Het, or combinations thereof,
C$_{2-6}$-alkynyl which is unsubstituted or substituted one or more times by F, Cl, Br, I, CN, OH, alkoxy having 1 to 4 carbon atoms, NR$^{13}$R$^{14}$, SH, SR$^{13}$, SOR$^{13}$, C$_{3-8}$-cycloalkyl, SO$_2$R$^{13}$, SO$_2$NR$^{13}$R$^{14}$, Si(R$^{15}$)$_3$, Ar, Het, or combinations thereof,
C$_{3-8}$-cycloalkyl which is unsubstituted or substituted one or more times by F, Cl, Br, I, CN, OH, alkoxy having 1 to 4 carbon atoms, NR$^{13}$R$^{14}$, SH, SR$^{13}$, SOR$^{13}$, unsubstituted C$_{3-8}$-cycloalkyl, SO$_2$R$^{13}$, SO$_2$NR$^{13}$R$^{14}$, Ar, Het, or combinations thereof,
halogen,
CN, NO$_2$, NR$^{13}$R$^{14}$, SH, SR$^{13}$, SOR$^{13}$, SO$_2$R$^{13}$, SO$_2$NR$^{13}$R$^{14}$, NR$^{13}$SO$_2$R$^{14}$, CONR$^{13}$R$^{14}$, CSNR$^{13}$R$^{14}$, COOR$^{13}$, NR$^{13}$COR$^{14}$, NR$^{13}$CSR$^{14}$, NR$^{13}$CONR$^{13}$R$^{14}$, NR$^{13}$CSNR$^{13}$R$^{14}$, NR$^{13}$COOR$^{14}$, NR$^{13}$CSOR$^{14}$, OCONR$^{13}$R$^{14}$, OCSNR$^{13}$R$^{14}$,
Ar,
Het, or
R$^{16}$O—;
R$^6$ to R$^{12}$ are each, independently,
H,
C$_{1-4}$-alkyl which is unsubstituted or substituted one or more times by F, Cl, Br, I, CN, alkoxy having 1 to 4 carbon atoms, Ar, or combinations thereof,
C$_{3-6}$-alkenyl which is unsubstituted or substituted one or more times by F, Cl, Br, I, CN, alkoxy having 1 to 4 carbon atoms, Ar, or combinations thereof,
C$_{3-6}$-alkynyl which is unsubstituted or substituted one or more times by F, Cl, Br, I, CN, alkoxy having 1 to 4 carbon atoms, Ar, or combinations thereof,
cycloalkyl having 3 to 10 carbon atoms, which is unsubstituted or substituted one or more times by halogen, hydroxy, oxo, cyano, alkyl having 1 to 4 carbon atoms, alkoxy having 1 to 4 carbon atoms, or combinations thereof,
cycloalkylalkyl having 4 to 16 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof,
Ar-alkyl, or
Het-alkyl;
$R^{13}$ and $R^{14}$ are each independently
H,
Ar,
Ar-alkyl,
Het,
$C_{1-4}$-alkyl which is unsubstituted or substituted one or more times by F, Cl, Br, I, CN, OH, alkoxy having 1 to 4 carbon atoms, monoalkylamino, dialkylamino, $C_{3-8}$-cycloalkyl, or combinations thereof,
cycloalkyl having 3 to 10 carbon atoms, which is unsubstituted or substituted one or more times by halogen, hydroxy, oxo, cyano, alkyl having 1 to 4 carbon atoms, alkoxy having 1 to 4 carbon atoms, or combinations thereof,
$C_{3-6}$-alkenyl which is unsubstituted or substituted one or more times by F, Cl, Br, I, CN, alkoxy having 1 to 4 carbon atoms, Ar, or combinations thereof, or
$C_{3-6}$-alkynyl which is unsubstituted or substituted one or more times by F, Cl, Br, I, CN, alkoxy having 1 to 4 carbon atoms, Ar or combinations thereof;
$R^{15}$ is $C_{1-6}$-alkyl;
$R^{16}$ is H,
$C_{1-6}$-alkyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof,
$C_{3-6}$-alkenyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof,
$C_{3-6}$-alkynyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof,
$C_{3-8}$-cycloalkyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof,
$C_{4-8}$-cycloalkylalkyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof,
Ar, or
Het;
m is 1, 2 or 3;
o is 1 or 2;
Ar is an aryl group containing 6 to 10 carbon atoms which is unsubstituted or substituted one or more times by
alkyl having 1 to 8 carbon atoms,
alkoxy having 1 to 8 carbon atoms,
halogen,
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkylaminocarbonyl,
acylamido,
acyloxy,
alkylthio having 1 to 8 carbon atoms,
alkylsulphinyl having 1 to 8 carbon atoms,
alkylsulphonyl having 1 to 8 carbon atoms,
sulfo,
sulfonylamino,
Het,
cycloalkylamino wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryloxy wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
arylthio wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
cycloalkyloxy wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, or
combinations thereof;
Ar-alkyl is an aryl-alkylene group wherein the alkylene portion contains 1 to 4 carbon atoms and is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio, and the aryl portion is Ar as defined above; and
Het is a heterocyclic group, which is fully saturated, partially saturated or fully unsaturated, having 5 to 10 ring atoms in which at least 1 ring atom is a N, O or S atom, which is unsubstituted or substituted one or more times by
alkyl having 1 to 8 carbon atoms,
alkoxy having 1 to 8 carbon atoms,
halogen,
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkoxycarbonylmethyl,
alkylaminocarbonyl,
acylamido,
acyloxy,
alkylthio having 1 to 8 carbon atoms,
alkylsulphinyl having 1 to 8 carbon atoms,
alkylsulphonyl having 1 to 8 carbon atoms,
sulfo,
oxo,
sulfonylamino,
cycloalkylamino wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryl containing 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryl-alkylene group wherein the aryl portion contains 6 to 10 carbon atoms and the alkylene portion contains 1 to 4 carbon atoms and is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
aryloxy wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
arylthio wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
cycloalkyloxy wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
heterocyclic group, which is fully saturated, partially saturated or fully unsaturated, having 5 to 10 ring atoms in which at least 1 ring atom is a N, O or S atom, which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
heterocyclic-alkyl group, in which the heterocylic portion is fully saturated, partially saturated or fully unsaturated, having 5 to 10 ring atoms in which at least 1 ring atom is a N, O or S atom, and the alkyl portion is an alkylene group containing 1-4 carbon atoms, wherein said heterocyclic-alkyl group is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, thio, or combinations thereof; and
Het-alkyl is a Het-alkylene group wherein the alkylene portion contains 1 to 4 carbon atoms, and the Het portion is Het as defined above; or
a pharmaceutically acceptable salts thereof.

2. A compound according to claim 1, wherein said compound is selected from:
(a) compounds wherein
$A_1$ is

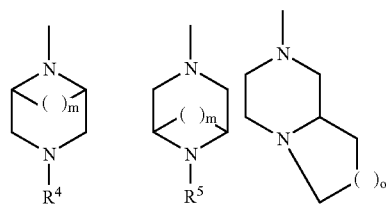

-continued

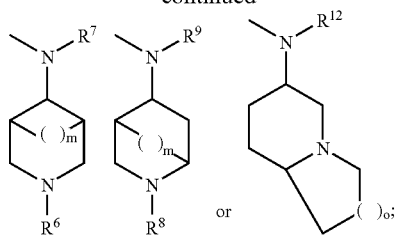

(b) compounds wherein
$A_1$ is

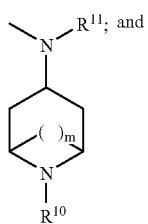

m is 1; and
and pharmaceutically acceptable salts thereof;
(c) compounds wherein
$A_1$ is

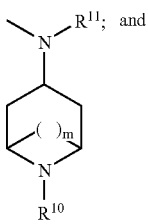

$R^1$ is $C_{2-6}$-alkyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkenyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkynyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, $Si(R^{15})_3$, Ar, Het, or combinations thereof, $C_{3-8}$-cycloalkyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof, CN, $NO_2$, $NR^{13}R^{14}$, SH, $SR^{13}$, $SOR^{13}$, $SO_2R^{13}$, $SO_2NR^{13}R^4$, $NR^{13}SO_2R^{14}$, $CONR^{13}R^{14}$, $CSNR^{13}R^{14}$, $COOR^{13}$, $NR^{13}COR^{14}$, $NR^{13}CSR^{14}$, $NR^{13}CONR^{13}R^{14}$, $NR^{13}CSNR^{13}R^{14}$, $NR^{13}COOR^{14}$, $NR^{13}CSOR^{14}$, $OCONR^{13}R^{14}$, $OCSNR^{13}R^{14}$, Ar,
Het, or
$R^{16}O$—; and
pharmaceutically acceptable salts thereof;
(d) compounds wherein
$A_1$ is

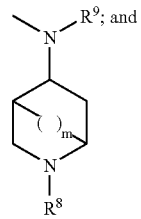

m is 3; and
pharmaceutically acceptable salts thereof;
(e): compounds wherein
$A_1$ is

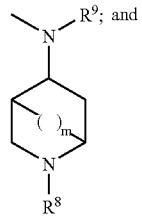

$R^1$ is $C_{2-6}$-alkyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkenyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, Ar, Het, or combinations thereof, $C_{2-6}$-alkynyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, $C_{3-8}$-cycloalkyl, $SO_2R^{13}$, $SO_2NR^{13}R^{14}$, $Si(R^{15})_3$, Ar, Het, or combinations thereof, $C_{3-8}$-cycloalkyl which is unsubstituted or substituted one or more times by F, Cl, Br, I, CN, OH, alkoxy having 1 to 4 carbon atoms, $NR^{13}R^{14}$, SH, $SR^{13}$, $SOR^{13}$, unsubstituted $C_{3-8}$-cycloalkyl, $SO_2R^{13}$, $SO_2NR^{13}R^{14}$, Ar, Het, or combinations thereof, halogen,
CN, $NO_2$, $NR^{13}R^{14}$, SH, $SR^{13}$, $SOR^{13}$, $SO_2R^{13}$, $SO_2NR^{13}R^{14}$, $NR^{13}SO_2R^{14}$, $CONR^{13}R^{14}$, $CSNR^{13}R^{14}$, $COOR^{13}$, $NR^{13}COR^{14}$, $NR^{13}CSR^{14}$, $NR^{13}CONR^{13}R^{14}$, $NR^{13}CSNR^{13}R^{14}$, $NR^{13}COOR^{14}$, $NR^{13}CSOR^{14}$, $OCONR^{13}R^{14}$, $OCSNR^{13}R^{14}$, Ar,
Het, or
$R^{16}O$—; and
pharmaceutically acceptable salts thereof;
(f) compounds wherein
B is S; and
pharmaceutically acceptable salts thereof; and
(g) compounds wherein
B is $H_2$; and
pharmaceutically acceptable salts thereof.

3. A compound according to claim 1, wherein R$^{13}$ and R$^{14}$ are each independently

H,

Ar,

Het,

C$_{1-4}$-alkyl which is unsubstituted or substituted one or more times by F, Cl, Br, I, CN, OH, alkoxy having 1 to 4 carbon atoms, monoalkylamino, dialkylamino, C$_{3-8}$-cycloalkyl, or combinations thereof, cycloalkyl having 3 to 10 carbon atoms, which is unsubstituted or substituted one or more times by halogen, hydroxy, oxo, cyano, alkyl having 1 to 4 carbon atoms, alkoxy having 1 to 4 carbon atoms, or combinations thereof, C$_{3-6}$-alkenyl which is unsubstituted or substituted one or more times by F, Cl, Br, I, CN, alkoxy having 1 to 4 carbon atoms, Ar, or combinations thereof, or C$_{3-6}$-alkynyl which is unsubstituted or substituted one or more times by F, Cl, Br, I, CN, alkoxy having 1 to 4 carbon atoms, Ar or combinations thereof; and Het is a heterocyclic group, which is fully saturated, partially saturated or fully unsaturated, having 5 to 10 ring atoms in which at least 1 ring atom is a N, O or S atom, which is unsubstituted or substituted one or more times by alkyl having 1 to 8 carbon atoms, alkoxy having 1 to 8 carbon atoms, halogen, amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, monoalkylamino having 1 to 8 carbon atoms, dialkylamino wherein the alkyl portions each have 1 to 8 carbon atoms, carboxy, alkoxycarbonyl, alkoxycarbonylmethyl, alkylaminocarbonyl, acylamido, acyloxy, alkylthio having 1 to 8 carbon atoms, alkylsulphinyl having 1 to 8 carbon atoms, alkylsulphonyl having 1 to 8 carbon atoms, sulfo, sulfonylamino, cycloalkylamino wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylaamino wherein the alkyl portions each have 1 to 8 carbon atoms, COR$^{16}$, CSR$^{16}$, cyano, hydroxyl, nitro, oxo, or thio, aryl containing 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR$^{16}$, CSR$^{16}$, cyano, hydroxyl, nitro, oxo, or thio, aryl-alkylene group wherein the aryl portion contains 6 to 10 carbon atoms and the alkylene portion contains 1 to 4 carbon atoms and is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylaamino wherein the alkyl portions each have 1 to 8 carbon atoms, COR$^{16}$, CSR$^{16}$, cyano, hydroxyl, nitro, oxo, or thio, aryloxy wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR$^{16}$, CSR$^{16}$, cyano, hydroxyl, nitro, oxo, or thio, arylthio wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR$^{16}$, CSR$^{16}$, cyano, hydroxyl, nitro, oxo, or thio, cycloalkyloxy wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR$^{16}$, CSR$^{16}$, cyano, hydroxyl, nitro, oxo, or thio, heterocyclic group, which is fully saturated, partially saturated or fully unsaturated, having 5 to 10 ring atoms in which at least 1 ring atom is a N, O or S atom, which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR$^{16}$, CSR$^{16}$, cyano, hydroxyl, nitro, oxo, or thio, heterocyclic-alkyl group, in which the heterocylic portion is fully saturated, partially saturated or fully unsaturated, having 5 to 10 ring atoms in which at least 1 ring atom is a N, O or S atom, and the alkyl portion is an alkylene group containing 1-4 carbon atoms, wherein said heterocyclic-alkyl group is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR$^{16}$, CSR$^{16}$, cyano, hydroxyl, nitro, oxo, or thio, or combinations thereof.

4. A compound according claim 3, wherein Het is a heterocyclic group, which is fully saturated, partially saturated or fully unsaturated, having 5 to 10 ring atoms in which at least 1 ring atom is a N, O or S atom, which is unsubstituted or substituted one or more times by
- alkyl having 1 to 8 carbon atoms,
- alkoxy having 1 to 8 carbon atoms,
- halogen,
- amino,
- cyano,
- hydroxyl,
- nitro,
- halogenated alkyl having 1 to 8 carbon atoms,
- halogenated alkoxy having 1 to 8 carbon atoms,
- hydroxyalkyl having 1 to 8 carbon atoms,
- hydroxyalkoxy having 2 to 8 carbon atoms,
- alkenyloxy having 3 to 8 carbon atoms,
- monoalkylamino having 1 to 8 carbon atoms,
- dialkylamino wherein the alkyl portions each have 1 to 8 carbon atoms,
- carboxy,
- alkoxycarbonyl,
- alkylaminocarbonyl,
- acylamido,
- acyloxy,
- alkylthio having 1 to 8 carbon atoms,
- alkylsulphinyl having 1 to 8 carbon atoms,
- alkylsulphonyl having 1 to 8 carbon atoms,
- sulfo,
- sulfonylamino,
- cycloalkylamino wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
- aryl containing 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
- aryl-alkylene group wherein the aryl portion contains 6 to 10 carbon atoms and the alkylene portion contains 1 to 4 carbon atoms and is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 C carbon atoms, $COR^{16}$, $CSR^{16}$, cyano, hydroxyl, nitro, oxo, or thio,
- aryloxy wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
- arylthio wherein the aryl portion contains 6 to 10 carbon atoms and is optionally substituted by halogen, alkyl having 1 to 8 carbon atoms, halogenated alkyl having 1 to 8 C atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
- cycloalkyloxy wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{16}$, $CSR^{16}$, cyano, hydroxyl, nitro, oxo, or thio,
- heterocyclic group, which is fully saturated, partially saturated or fully unsaturated, having 5 to 10 ring atoms in which at least 1 ring atom is a N, O or S atom, which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 C atoms, $COR^{16}$, $CSR^{16}$, cyano, hydroxyl, nitro, oxo, or thio, or combinations thereof.

5. A compound according to claim 1, wherein $R^1$ is H, alkyl, halogenated alkyl, $OR^{16}$, halogen, Ar, or Het.

6. A compound according to claim 5, wherein Het is in each case substituted or unsubstituted thienyl, substituted or unsubstituted furyl, substituted or unsubstituted pyrazolyl, substituted or unsubstituted thiazolyl, substituted or unsubstituted dihydropyranyl, substituted or unsubstituted oxazolyl, substituted or unsubstituted triazolyl, substituted or unsubstituted imidazolyl, or substituted or unsubstituted isoxazolyl.

7. A compound according to claim 5, wherein Het is is each case 2-thienyl, 3-thienyl, 2-(4-methyl)thienyl, 2-(5-methyl)thienyl), 2-oxazolyl, (trifluoromethylphenyl)thienyl, 2-(4-methyl)thiazolyl, (3,6-dihydro-2H-pyran-4-yl), (1-benzyl-1H-1,2,3-triazol-4-yl), 2-oxo-3-propylimidazolidin-1-yl), dimethylisoxazolyl, 1-benzyl-1H-pyrazol-4-yl, 2-furyl, 3-furyl, or 2-(5-methyl)furyl).

8. A compound according to claim 1, wherein $X^1$ is CH.

9. A compound according to claim 1, wherein $X^4$ is CH or $CR^1$, in which $R^1$ is alkyl, halogenated alkyl, alkoxy, halogenated alkoxy, or halogen.

10. A compound according to claim 1, wherein $X^2$ and $X^3$ are CH or $CR^1$, in which $R^1$ is alkyl, halogenated alkyl, alkoxy, halogenated alkoxy, halogen, cyano, alkynyl, cycloalkyl, cycloalkyloxy, cycloalkylalkoxy, Ar or Het.

11. A compound according to claim 1, wherein $R^7$, $R^9$, $R^{11}$, and $R^{12}$ are in each case H or alkyl.

12. A compound according to claim 1, wherein $R^6$, $R^8$, and $R^{10}$ are in each case H, alkyl, cycloalkylalkyl or Ar-alkyl.

13. A compound according to claim 1, wherein said compound is of formula I,
$A_1$ is 2-azabicyclo[2.2.1]heptan-5-amino, 2-methyl-2-azabicyclo[2.2.1]heptan-5-amino, 2-azabicyclo[2.2.2]octan-5-amino, or 2-methyl-2-azabicyclo[2.2.2]octan-5-amino,
B is O.

14. A compound according to claim 1, wherein said compound is selected from:
(a) compounds wherein $X^1$, $X^2$, and $X^3$ are CH, $X^4$ is $CR^1$, and B is O,
(b) compounds wherein $X^1$, $X^2$, and $X^4$ are CH, $X^3$ is $CR^1$, and B is O, and (c) compounds wherein $X^1$, $X^3$, and $X^4$ are CH, $X^2$ is $CR^1$, and B is O.

15. A compound according to claim 1, wherein said compound is selected from:

7-Methoxy-N-(endo-9-methyl-9-azabicyclo[3.3.1]non-3-yl)-1H-indazole-3-carboxamide,
N-(2-Methyl-2-azabicyclo[2.2.1]hept-5-yl)-5-(trifluoromethoxy)-1H-indazole-3-carboxamide,
6-Methoxy-N-(2-methyl-2-azabicyclo[2.2.1]hept-5-yl)-1H-indazole-3-carboxamide,
N-(2-Methyl-2-azabicyclo[2.2.1]hept-5-yl)-6-(4-methyl-1,3-thiazol-2-yl)-1H-indazole-3-carboxamide,
5-Difluoromethoxy-N-(endo-8-methyl-8-azabicyclo[3.2.1]oct-3-yl)-1H-indazole-3-carboxamide,
5-Difluoromethoxy-N-(exo-8-methyl-8-azabicyclo[3.2.1]oct-3-yl)-1H-indazole-3-carboxamide,
5-Difluoromethoxy-N-(8-methyl-8-azabicyclo[3.2.1]oct-3-yl)-1H-indazole-3-carboxamide
6-Difluoromethoxy-N-(endo-8-methyl-8-azabicyclo[3.2.1]oct-3-yl)-1H-indazole-3-carboxamide,
6-Difluoromethoxy-N-(8-methyl-8-azabicyclo[3.2.1]oct-3-yl)-1H-indazole-3-carboxamide,
N-(8-Methyl-8-azabicyclo[3.2.1]oct-3-yl)-5-(4-methyl-1,3-thiazol-2-yl)-1H-indazole-3-carboxamide,
N-(exo-8-Methyl-8-azabicyclo[3.2.1]oct-3-yl)-5-(4-methyl-1,3-thiazol-2-yl)-1H-indazole-3-carboxamide,
N-(2-Methyl-2-azabicyclo[2.2.1]hept-5-yl)-5-(4-methyl-1,3-thiazol-2-yl)-1H-indazole-3-carboxamide,
6-(3,6-Dihydro-2H-pyran-4-yl)-N-(2-methyl-2-azabicyclo[2.2.1]hept-5-yl)-1H-indazole-3-carboxamide,
N-(2-Methyl-2-azabicyclo[2.2.1]hept-5-yl)-6-(5-methyl-1,3-thiazol-2-yl)-1H-indazole-3-carboxamide,
6-Difluoromethoxy-N-(2-methyl-2-azabicyclo[2.2.1]hept-5-yl)-1H-indazole-3-carboxamide,
N-(2-Methyl-2-azabicyclo[2.2.1]hept-5-yl)-6-(1,3-thiazol-2-yl)-1H-indazole-3-carboxamide,
N-(2-Methyl-2-azabicyclo[2.2.1]hept-5-yl)-5-(5-methyl-1,3-thiazol-2-yl)-1H-indazole-3-carboxamide,
N-(2-Methyl-2-azabicyclo[2.2.1]hept-5-yl)-6-(trifluoromethoxy)-1H-indazole-3-carboxamide,
N-(endo-8-Methyl-8-azabicyclo[3.2.1]oct-3-yl)-5-(4-methyl-1,3-thiazol-2-yl)-1H-indazole-3-carboxamide,
N-(2-Methyl-2-azabicyclo[2.2.1]hept-5-yl)-6-(2-thienyl)-1H-indazole-3-carboxamide,
N-(2-Methyl-2-azabicyclo[2.2.1]hept-5-yl)-5-(1,3-oxazol-2-yl)-1H-indazole-3-carboxamide,
5-(3,6-Dihydro-2H-pyran-4-yl)-N-(2-methyl-2-azabicyclo[2.2.1]hept-5-yl)-1H-indazole-3-carboxamide,
5-Methoxy-N-(2-methyl-2-azabicyclo[2.2.1]hept-5-yl)-1H-indazole-3-carboxamide,
N-[(rel-1S,4S,5S)-2-Methyl-2-azabicyclo[2.2.1]hept-5-yl]-6-(4-methyl-1,3-thiazol-2-yl)-1H-indazole-3-carboxamide,
N-[(rel-1S,4S,5R)-2-Methyl-2-azabicyclo[2.2.1]hept-5-yl]-6-(4-methyl-1,3-thiazol-2-yl)-1H-indazole-3-carboxamide,
N-[(rel-1S,4S,5R)-2-Methyl-2-azabicyclo[2.2.1]hept-5-yl]-5-(trifluoromethoxy)-1H-indazole-3-carboxamide,
N-[(rel-1S,4S,5S)-2-Methyl-2-azabicyclo[2.2.1]hept-5-yl]-5-(trifluoromethoxy)-1H-indazole-3-carboxamide,
N-(2-Methyl-2-azabicyclo[2.2.1]hept-5-yl)-5-(1,3-thiazol-2-yl)-1H-indazole-3-carboxamide,
N-(endo-8-methyl-8-azabicyclo[3.2.1]oct-3-yl)-5-(1,3-oxazol-2-yl)-1H-indazole-3-carboxamide,
N-(2-Methyl-2-azabicyclo[2.2.1]hept-5-yl)-6-(5-methyl-1,3-thiazol-2-yl)-1H-indazole-3-carboxamide,
N-(2-Methyl-2-azabicyclo[2.2.1]hept-5-yl)-5-(trifluoromethoxy)-1H-indazole-3-carboxamide,
N-(2-Methyl-2-azabicyclo[2.2.1]hept-5-yl)-6-(4-methyl-1,3-thiazol-2-yl)-1H-indazole-3-carboxamide,
6-Amino-N-(2-methyl-2-azabicyclo[2.2.1]hept-5-yl)-1H-indazole-3-carboxamide,
5-(1-Benzyl-1H-1,2,3-triazol-4-yl)-N-(8-methyl-8-azabicyclo[3.2.1]oct-3-yl)-1H-indazole-3-carboxamide,
6-{[(Cyclopentylamino)carbonyl]amino}-N-(endo-8-methyl-8-azabicyclo[3.2.1]oct-3-yl)-1H-indazole-3-carboxamide,
N-(endo-8-Methyl-8-azabicyclo[3.2.1]oct-3-yl)-6-{[(propylamino)carbonyl]amino}-1H-indazole-3-carboxamide,
5-({[(4-Fluorophenyl)amino]carbonyl}amino)-N-(endo-8-methyl-8-azabicyclo[3.2.1]oct-3-yl)-1H-indazole-3-carboxamide,
6-({[(4-Fluorobenzyl)amino]carbonyl}amino)-N-(endo-8-methyl-8-azabicyclo[3.2.1]oct-3-yl)-1H-indazole-3-carboxamide,
5-({[(3-Methoxyphenyl)amino]carbonyl}amino)-N-(endo-8-methyl-8-azabicyclo[3.2.1]oct-3-yl)-1H-indazole-3-carboxamide,
6-({[(3-Methoxybenzyl)amino]carbonyl}amino)-N-(endo-8-methyl-8-azabicyclo[3.2.1]oct-3-yl)-1H-indazole-3-carboxamide,
N-(8-methyl-8-azabicyclo[3.2.1]oct-3-yl)-5-(2-oxo-3-propylimidazolidin-1-yl)-1H-indazole-3-carboxamide,
and pharmaceutically acceptable salts thereof.

16. A pharmaceutical composition comprising a compound according to claim 1 and a pharmaceutically acceptable carrier.

17. A compound according to claim 15, wherein said compound is in the form of a hydroformate or a hydrochloride salt.

18. A compound according to claim 17, wherein said compound is selected from:

7-Methoxy-N-(endo-9-methyl-9-azabicyclo[3.3.1]non-3-yl)-1H-indazole-3-carboxamide hydroformate,
N-(2-Methyl-2-azabicyclo[2.2.1]hept-5-yl)-5-(trifluoromethoxy)-1H-indazole-3-carboxamide hydroformate,
6-Methoxy-N-(2-methyl-2-azabicyclo[2.2.1]hept-5-yl)-1H-indazole-3-carboxamide hydroformate,
N-(2-Methyl-2-azabicyclo[2.2.1]hept-5-yl)-6-(4-methyl-1,3-thiazol-2-yl)-1H-indazole carboxamide hydroformate,
5-Difluoromethoxy-N-(endo-8-methyl-8-azabicyclo[3.2.1]oct-3-yl)-1H-indazole-3-carboxamide hydroformate,
5-Difluoromethoxy-N-(exo-8-methyl-8-azabicyclo[3.2.1]oct-3-yl)-1H-indazole-3-carboxamide hydroformate,
5-Difluoromethoxy-N-(8-methyl-8-azabicyclo[3.2.1]oct-3-yl)-1H-indazole-3-carboxamide hydroformate,
6-Difluoromethoxy-N-(endo-8-methyl-8-azabicyclo[3.2.1]oct-3-yl)-1H-indazole-3-carboxamide hydroformate,
6-Difluoromethoxy-N-(8-methyl-8-azabicyclo[3.2.1]oct-3-yl)-1H-indazole-3-carboxamide hydroformate,
N-(exo-8-Methyl-8-azabicyclo[3.2.1]oct-3-yl)-5-(4-methyl-i ,3-thiazol-2-yl)-1H-indazole-3-carboxamide hydroformate,
N-(2-Methyl-2-azabicyclo[2.2.1]hept-5-yl)-5-(4-methyl-1,3-thiazol-2-yl)-1H-indazole-3-carboxamide hydroformate,
6-(3,6-Dihydro-2H-pyran-4-yl)-N-(2-methyl-2-azabicyclo[2.2.1]hept-5-yl)-1H-indazole-3-carboxamide hydroformate, N-(2-Methyl-2-azabicyclo[2.2.1]hept-5-yl)-6-(5-methyl-1,3-thiazol-2-yl)-1H-indazol-3-carboxamide hydroformate, 6-Difluoromethoxy-N-(2-methyl-2-azabicyclo[2.2.1]hept-5-yl)-1H-indazole-3-carboxamide hydroformate, N-(2-Methyl-2-azabicyclo[2.2.1]hept-5-yl)-6-(1,3-thiazol-2-yl)-1H-indazole-3-carboxamide hydroformate, N-(2-Methyl-2-azabicyclo[2.2.1]hept-5-yl)-5-(5-methyl-1,3-thiazol-2-yl)-1H-indazole-3-carboxamide hydroformate, N-(2-Methyl-2-azabicyclo[2.2.1]hept-5-yl)-6-(trifluoromethoxy)-1H-indazole-3-carboxamide hydroformate, N-(endo-8-Methyl-8-azabicyclo[3.2.1]oct-3-yl)-5-(4-methyl-1,3-thiazol-2-yl)-1H-indazole-3-carboxamide hydroformate, N-(2-Methyl-2-azabicyclo[2.2.1]hept-5-yl)-6-(2-thienyl)-1H-indazole-3-carboxamide hydroformate, N-(2-Methyl-2-azabicyclo[2.2.1]hept-5-yl)-5-(1,3-oxazol-2-yl)-1H-indazole-3-carboxamide hydroformate, 5-(3,6-Dihydro-2H-pyran-4-yl)-N-(2-methyl-2-azabicyclo[2.2.1]hept-5-yl)-1H-indazole-3-carboxamide hydroformate, 5-Methoxy-N-(2-methyl-2-azabicyclo[2.2.1]hept-5-yl)-1H-indazole-3-carboxamide hydroformate, N-(2-Methyl-2-azabicyclo[2.2.1]hept-5-yl)-5-(1,3-thiazol-2-yl)-1H-indazole-3-carboxamide hydroformate, N-(endo-8-methyl-8-azabicyclo[3.2.1]oct-3-yl)-5-(1,3-oxazol-2-yl)-1H-indazole-3-carboxamide hydroformate, N-(2-Methyl-2-azabicyclo[2.2.1]hept-5-yl)-6-(5-methyl-1,3-thiazol-2-yl)-1H-indazole-3-carboxamide hydroformate, N-(2-Methyl-2-azabicyclo[2.2.1]hept-5-yl)-5-(trifluoromethoxy)-1H-indazole-3-carboxamide hydroformate, N-(2-Methyl-2-azabicyclo[2.2.1]hept-5-yl)-6-(4-methyl-1,3-thiazol-2-yl)-1H-indazole-3-carboxamide hydroformate, 5-(1-Benzyl-1H-1,2,3-triazol-4-yl)-N-(8-methyl-8-azabicyclo[3 .2.1]oct-3-yl)-1H-indazole-3-carboxamide dihydroformate, 6-{[(Cyclopentylamino)carbonyl]amino}-N-(endo-8-methyl-8-azabicyclo[3.2.1]oct-3-yl)-1H-indazole-3-carboxamide hydroformate, N-(endo-8-Methyl-8-azabicyclo[3.2.1]oct-3-yl)-6-{[(propylamino)carbonyl]amino }-1H-indazole-3-carboxamide hydroformate, 5-({[(4-Fluorophenyl)amino]carbonyl}amino)-N-(endo-8-methyl-8-azabicyclo[3.2.1]oct-3-yl)-1H-indazole-3-carboxamide hydroformate, 6-({[(4-Fluorobenzyl)amino]carbonyl}amino)-N-(endo-8-methyl-8-azabicyclo[3.2.1]oct-3-yl)-1H-indazole-3-carboxamide hydroformate, 5-({[(3-Methoxyphenyl)amino]carbonyl}amino)-N-(endo-8-methyl-8-azabicyclo[3.2.1]oct-3-yl)-1H-indazole-3-carboxamide hydroformate, 6-({[(3-Methoxybenzyl)amino]carbonyl}amino)-N-(endo-8-methyl-8-azabicyclo[3.2.1]oct-3-yl)-1H-indazole-3-carboxamide hydroformate, and N-(8-methyl-8-azabicyclo[3.2.1]oct-3-yl)-5-(2-oxo-3-propylimidazolidin-1-yl)-1H-indazole-3-carboxamide hydroformate.

19. A compound according to claim 1, wherein said compound is of formula I in which $X^1$ to $X^4$ each CH or $CR^1$;

$A_1$ is endo or exo 8-azabicyclo[3.2.1]octan-3-amino, 8-methyl-8-azabicyclo[3.2.1]octan-3-amino, 9-azabicyclo[3.3.1]nonan-3-amino, or endo or exo 9-methyl-9-azabicyclo[3.3.1]non-3-amino;

B is O;

$R^{11}$ is H or $CH_3$; and $R^1$ is $CF_3$, $CH_3O$, $CF_3O$, cyclopropyl, cyano, ethynyl which is substituted or unsubstituted, phenyl which is substituted or unsubstituted, furyl which is substituted or unsubstituted, thienyl which is substituted or unsubstituted, bithienyl which is substituted or unsubstituted, pyrazolyl which is substituted or unsubstituted, thiazolyl which is substituted or unsubstituted, imidazolyl which is substituted or unsubstituted, pyrrolidinyl which is substituted or unsubstituted, morpholinyl which is substituted or unsubstituted, or thiomorpholinyl which is substituted or unsubstituted.

20. A compound according to claim 1, wherein said compound is of formula I in which $A_1$ is endo or exo 8-methyl-8-azabicyclo[3.2.1]octan-3-amino, octahydropyrrolo[1,2-a]pyrazinyl, 3-methyl-3,8-diazabicyclo[3.2.1]octan-8-amino, 8-methyl-3,8-diazabicyclo[3.2.1]oct-3-yl, endo or exo 9-methyl-9-azabicyclo[3.3.1]nonan-3-amino, 2-methyl-2-azabicyclo[2.2.2]octan-5-amino, 2-azabicyclo[2.2.1]heptan-5-amino, or 8-azabicyclo[3.2.1]octan-3-amino; and $X^1$ to $X^4$ are each CH or $CR^1$; and $X^2$ and $X^3$ are each CH or $CR^1$ in which $R^1$ is alkyl, halogenated alkyl, alkoxy, halogenated alkoxy, halogen, cyano, alkynyl, cycloalkyl, cycloalkyloxy, cycloalkylalkoxy, Ar or Het.

\* \* \* \* \*

UNITED STATES PATENT AND TRADEMARK OFFICE
CERTIFICATE OF CORRECTION

PATENT NO. : 7,488,737 B2  Page 1 of 1
APPLICATION NO. : 11/111958
DATED : February 10, 2009
INVENTOR(S) : Wenge Xie et al.

It is certified that error appears in the above-identified patent and that said Letters Patent is hereby corrected as shown below:

On the title page item (75), Inventors: line 1, reads "Mahwag, NJ" should read -- Mahwah, NJ --
Column 135, line 54, reads "one of $X^1$" should read -- one of $X^1$ --
Column 136, line 20, reads "4 carbon atoms $NR^{13}R^{14}$," should read -- 4 carbon atoms, $NR^{13}R^{14}$, --
Column 138, line 65, reads "defined above; and" should read -- defined above; --
Column 141, delete the middle of the three compounds at the top of the column
Column 141, line 29, reads "and pharmaceutically" should read -- pharmaceutically --
Column 143, line 58, reads "dialkylaamino" should read -- dialkylamino --
Column 144, line 10, reads "dialkylaamino" should read -- dialkylamino --
Column 145, line 53, reads "C carbon" should read -- carbon --
Column 145, line 63, decrease indent at the beginning of the line
Column 146, line 36, reads "thienyl)," should read -- thienyl, --
Column 146, line 40, reads "2-(5-methyl)furyl)." should read -- 2-(5-methyl)furyl. --
Column 147, line 18, reads "...3-carboxamide" should read -- ...3-carboxamide, --
Column 148, line 59-60, reads "...methyl-i,3-thiazol..." should read -- ...methyl-1,3-thiazol... --
Column 150, line 6, begin new line after "hydroformate," and before "6-({[(3-Methoxy..."
Column 150, line 16, reads "$X^1$ to $X^4$ each" should read -- $X^1$ to $X^4$ are each --
Column 150, line 30, reads "pyffolidinyl" should read -- pyrrolidinyl --

Signed and Sealed this

Twenty-ninth Day of September, 2009

David J. Kappos
*Director of the United States Patent and Trademark Office*